United States Patent [19]

Dziegiel et al.

[11] Patent Number: 5,231,168
[45] Date of Patent: Jul. 27, 1993

[54] MALARIA ANTIGEN

[75] Inventors: Morten Dziegiel, Roskilde; Martin Borre, Copenhagen, both of Denmark; Søren Jepsen, Overisse, Belgium; Jens Vuust, Dragør, Denmark; Klaus Rieneck, Copenhagen, Denmark; Annette Wind, Farum, Denmark; Palle H. Jakobsen, Køge, Denmark

[73] Assignee: Statens Seruminstitut, Copenhagen, Denmark

[21] Appl. No.: 409,658

[22] Filed: Sep. 18, 1989

Related U.S. Application Data

[63] Continuation-in-part of Ser. No. 318,885, Mar. 3, 1989, abandoned.

[30] Foreign Application Priority Data

Sep. 16, 1988 [DK] Denmark ............................ 5191/88

[51] Int. Cl.⁵ ...................... C07K 13/00; C07K 7/00; A61K 37/02
[52] U.S. Cl. .................................... 530/350; 530/300
[58] Field of Search ................ 530/350, 402, 300; 435/69.1, 71.1, 69.1

[56] References Cited

U.S. PATENT DOCUMENTS

| | | | |
|---|---|---|---|
| 4,707,357 | 11/1987 | Dame et al. | 424/88 |
| 4,735,799 | 7/1988 | Patarroyo | 424/88 |
| 4,767,622 | 8/1988 | Ristic et al. | 424/88 |

FOREIGN PATENT DOCUMENTS

| | | |
|---|---|---|
| 112784 | 4/1984 | European Pat. Off. . |
| 136215 | 3/1985 | European Pat. Off. . |
| 136932 | 4/1985 | European Pat. Off. . |
| 209643 | 4/1986 | European Pat. Off. . |
| 223665 | 5/1987 | European Pat. Off. . |
| 252588 | 1/1988 | European Pat. Off. . |
| WO84/02471 | 7/1984 | PCT Int'l Appl. . |
| WO84/02472 | 7/1984 | PCT Int'l Appl. . |
| WO84/02917 | 8/1984 | PCT Int'l Appl. . |
| WO85/00975 | 3/1985 | PCT Int'l Appl. . |
| WO85/03724 | 8/1985 | PCT Int'l Appl. . |
| WO85/03725 | 8/1985 | PCT Int'l Appl. . |
| WO86/00620 | 1/1986 | PCT Int'l Appl. . |
| WO88/00595 | 1/1988 | PCT Int'l Appl. . |
| WO88/00597 | 1/1988 | PCT Int'l Appl. . |
| 2099300 | 12/1982 | United Kingdom . |
| 2199140 | 6/1988 | United Kingdom . |

OTHER PUBLICATIONS

Chulay (Abst.) Primary Structure of a Lysine & Glutanine Rich P. falcipun anhgta located at the Meirozoite Surface & in the Parasitophorons Vaeuole. 1988.

Jendonki et al. J of Imm 134:194-45 Characterization of One Polypeptide Antigen Potentially Related to Protective Immunity Against the Blood Infector by P. falciparum in the Squirrel Monkey.

Geysen et al. PNAS 81: 3998-4002, 1984.

Matsudana J of Biol Chem 262: 10035-38, 1987.

(List continued on next page.)

Primary Examiner—Christine M. Nucker
Assistant Examiner—H. Sidberry
Attorney, Agent, or Firm—Iver P. Cooper

[57] ABSTRACT

The present invention relates to a polypeptide comprising a characteristic amino acid sequence derived from the Plasmodium falciparum antigen GLURP, a polypeptide which is recognized by an antibody raised against or reactive with a polypeptide comprising said characteristic amino acid sequence and/or an antibody reactive with native GLURP, a nucleic acid molecule (DNA-fragment) encoding said polypeptide, an expression vector carrying the nucleic acid molecule, an organism expressing said nucleic acid molecule so as to produce said polypeptide, a monoclonal antibody directed against said polypeptide, a diagnostic agent comprising said antibody or said polypeptide for use in assaying Plasmodium falciparum infection and thus diagnosing malaria, and the use of said antibody or said polypeptide for therapeutic purposes, e.g. as a component in a vaccine.

7 Claims, 21 Drawing Sheets

OTHER PUBLICATIONS

Kemp et al (1) UCLA Symposia pp. 229-238, 1984, Mol. Biol. of Host-Parasite Interations.

Kemp et al. (2) PNAS 80: 3787-3791 1983, Merrifield et al.

Jepsen, S. et al. Immunoadsorbent Isolation of Antigens from the Culture Medium of In Vitro Cultivated *Plasmodium falciparum*, Acta Path. Microbiol. Scand. Sect. C, 89:99-103 (1981).

Jakobsen, P. H. et al. Demonstration of Soluble *Plasmodium falciparum* Antigens Reactive with Limulus Amoebocyte Lysate and Polymyxin B, Parasite Immunology 10:593-606 (1988).

Jepsen, S. Antigens and Antibodies in Plasmodium falciparum Malaria Studied by Immunoelectrophoretic Methods Acta Path. Microbiol. Scand. Sect. C. 88:263-270 (1980).

da Silva, L. R. et al. *Plasmodium falciparum* Polypeptides Released During In Vitro Cultivation, Bulletin of the World Health Organization, 61(1):105-112 (1983).

Bygbjerg, I. C. et al. Specific Proliferative Response of Human Lymphocytes to Purified Soluble Antigens From *Plasmodium falciparum* in vitro cultures and to Antigens from Malaria Patients' Sera, Clin. Exp. Immunol. 59:421-426(1985).

Scherf, A. et al. The 11-1 Gene of *Plasmodium falciparum* Codes for Distinct Fast Evolving Repeats, the EMBO Journal vol. 7.4 pp. 1129-1137 (1988).

Jepsen, S. Inhibition of In Vitro Growth of *Plasmodium falciparum* by Purified Antimalarial Human IgG Antibodies Scand. J. Immunol. 18:567-571 (1983).

Jakobsen, P. H. et al. Soluble *Plasmodium falciparum* Antigens Contain Carbohydrate Moieties Important for Immune Reactivity, Journal of Clinical Microbiology, 25:2075-2079 (1987).

Triglia, T. et al., Structure of a *Plasmodium falciparum* Gene that Encodes a Glutamic Acid-Rich Protein (GARP), Molecular and Biochemical Parasitology, 31:199-202 (1988).

Perler, F. B. et al., Cloning and Characterization of an Abundant *Plasmodium knowlesi* Antigen which Cross Reacts with Gambian Sera, Molecular and Biochemical Parasitology 25:185-193 (1987).

Jakobsen, P. H. et al. Inhibitory Monoclonal Antibodies to Soluble *Plasmodium falciparum* Antigens, Parasitol Res. 73:518-523 (1987).

Anders, et al.; Antigens with repeated amino acid sequences from the asexual blood stages of *Plasmodium falciparum;* Prog. Allergy, 41:148-172 (1988).

Hyde, et al.; Anomalous dinucleotide frequencies in both coding and non-coding regions from the genome of the human malarial parasite *Plasmodium falciparum* (1987) Gene: 61:177-187.

S. Jepsen et al.: *Antigens and Antibodies in Plasmodium falciparum Malaria Studied by Immunoelectrophoretic Methods,* Acta path. microbiol. scand. Sect. C., 88:263-270 1980.

S. Jepsen et al.: *Immunoadsorbent Isolation of Antigens from the Culture Medium of In Vitro Cultivated Plasmodium falciparum,* Acta path. microbiol. scand. Sect. C., 89:9-103, 1981.

P. H. Jakobsen et al.: *Demonstration of soluble Plasmodium falciparum antigens reactive with Limulus amoebocyte Lysate and polymyx in B,* Parasite Immunology, 10: 593-606, 1988.

I. C. Bygbjerg et al.: *Specific proliferative response of human Lynphocytes to purified soluble antigens from Plasmodium falciparum in vitro cultures and to antigens from malaria patients' sera,* Clin. exp. Immunol., 59: 421-426, 1985.

S. Jepsen: *Inhibition of in Vitro Growth of Plasmodium falciparum by Purified Antimalarial Human IgG Antibodies,* Scand. J. Immunol., 18: 567-571, 1983.

P. H. Jakobsen et al.: *Inhibitory monoclonal antibodies to soluble Plasmodium falciparum antigens,* Parasitol. Res., 73: 518-523, 1987.

P. H. Jakobsen et al.: *Soluble Plasmodium falciparum Antigens Contain Carbohydrate Moieties Important for Immune Reactivity,* Journal of Clinical Microbiology, 2075-2079, Nov. 1987.

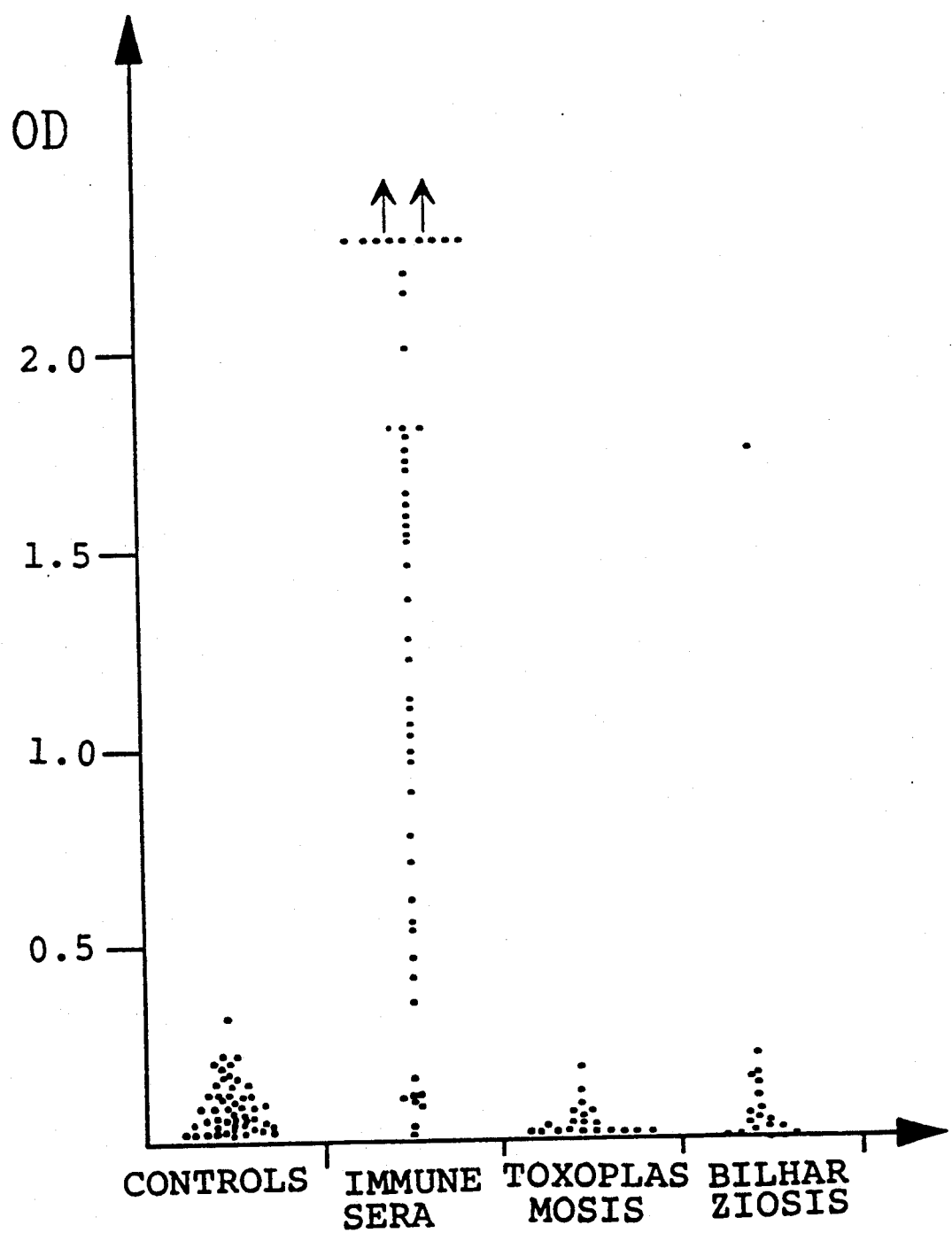
Fig. 6 : Fusion protein ELISA
Antigen amount 0,16μg/well

FIG. 7a

```
   1 GAATTCGTTG AATCGGAAAA AAGCGAGCAT GAAGCAGCTG AAAATGAAGA AAGTAGTCTT
  61 GAAGAAGGCC ATCATGAAGA AATTGTACCT GAACAAAATA ATGAAGAATC AGGTGAAAGT
 121 AAATTAGTTG ATAATGATGA AGGTGGTTTT GAAGAAGCTC ATCATGAAAA TTTTTCATCT
 181 GAAGTAAGTA ACTCTGAATT AAATGAAAAT GAATTGTTTG AATCTGACAA AAGTGTAACT
 241 GAACCTGCTG AACATGAAGA AGTTGTATCT GAAGAAAGCA ACCCTGAACC AGCTGAAAAT
 301 GAAGAAAGTA GTATAGAAGA AGCTCATCAG GAAGAAATTG TACCTGAACA AAATGATGAA
 361 GAATCAGGTG AAAGTGGATT AGTTGATAAT GAAGAAGGTG ATTTTGAAGA ACCTAATCAT
 421 GAAGAATTTG AACCTGATCA AAATGACTCT GAATTAAGTG AAAATGAATT AGTTGAATCA
 481 GAAAAAGTG TATCTGAACC AGCTGAACAT GTAGAAATTG TATCAGAAAA AGTGTATCT
 541 GAACCAGCTG AACACGTAGA AATTGTATCT GAAAAAGTA CATCCGAACC AGCTGAACAT
 601 GTAGAAAGTG TATCTGAACA AAGTAATAAC GAACCATCCG AAAAGAAAGA TGGACCAGTT
 661 CCTTCAAAAC CATTTGAAGA AATTGAAAAA GTGGATGTTC AACCTAAAAT TGTAGACCTT
 721 CAAATAATTG AACCTAATTT TGTTGACTCA CAACCAAATC CACAAGAACC AGTTGAACCA
 781 TCATTGTCA AATTGAAAA AGTTCCTTCT GAAGAAAATA AACATGCAAG TGTTGATCCT
 841 GAAGTAAAG AAAAGAAAA TGTATCTGAAG AAAAACAAAA TTCACAAGAA
 901 TCAGTTGAAG AAATTCCAGT AAATGAGGAT GAATTGAAG ATGTTCACAC TGAACAATTA
 961 GATTAGATC ATAAAACAGT ATAGTAGAAG TTGAAGAAAT TCCTTCAGAA
1021 CTACATGAAA ATGAAGTGGC TCATCCAGAA ATTGTTGAAA TTGAGGAAGT TTTTCCTGAA
```

FIG. 7b

```
1081  CCAAATCAAA ATAACGAATT TCAAGAAATT AATGAAGATG ATAAAAGTGC ACATATTCAG
1141  CATGAAATAG TAGAAGTAGA AGAAATACTT CCAGAAGATG ATAAAAATGA AAAAGTTGAA
1201  CATGAAATAG TAGAAGTTGA AGAAATTCTA CCAGAAGATA AAAATGAAAA AGGTCAACAT
1261  GAAATAGTAG AGGTTGAAGA AATTCTACCA GAAGATGATA AAAATGAAAA AGTTGAACAT
1321  GAAATAGTAG AAGTTGAAGA AATTCTACCA GAAGATAAAA ATGAAAAAGG TCAACATGAA
1381  ATAGTAGAGG TTGAAGAAAT TCTACCAGAA GATAAAAATG AAAAAGTTGA ACATGAAATA
1441  GTAGAAGTTG AAGAAATTCT ACCAGAAGAT AAAAATGAAA AAGGTCAACA TGAAATAGTA
1501  GAGGTTGAAG AAATTCTACC AGAAGATAAA AATGAAAAAG TTCAACATGA AATAGTAGAA
1561  GTTGAAGAAA TTCTACCAGA AGATAAAAAT GAAAAAGGTC AACATGAAAT AGTAGAGGTT
1621  GAAGAAATTC TACCAGAAGA TAAAAATGAA AAAGGTCAAC ATGAAATAGT AGAGGTTGAA
1681  GAAGAAATTC TACCAGAAGA TAAAAATGAA AAGTTCAACA TGAAATAGTA GAGGTTGAA
1741  GAAATTCTAC CAGAAGATAA AATGAAAAAG TTCAACATGA ATGAAATAGT AGAGGTTGAA
1801  ATTCTTCCAG AATTGTTGA AATTGAAGAA GTTCAACATG AATAGTAGA GGTTGAAGAA
1861  ATTGAAACTA TAAACCAGA AGAAAAAAG AATGAATTTA GTGTTGAAGA CAATGAAAT
1921  CCACAAGAAC CCGTGGTACC TACATTAAAT GAAATGAAA AGTTACTCC AAAGCAATT
1981  GAAGGTGAAT CCACTAAACC AGATATAGTT CAATTAAAA TAGTACAAGA CAAACCATCT
2041  AATAAAAAGG AACACCAGT AGTAGATGGT CCAAAACATG TAGAACAAA TATACAAGAA
```

FIG. 7c

```
2101 GATGATAATG ATGAAGAGGA TGATGATGAT ATAGATTTTG AGGATTATC AAGAAAGAT
2161 GATGAAAAGG ATTCATCAAA TAAAATAAA AAGAAATCAT CTTTATAAC ATATATCT
2221 ACAAAGAAAT TTAAAAAGT ATCTCAAACT ATTGTAAGTG TTATGATTAA TGCATATGAT
2281 GGTGTTATTC AAGTTGTAAG TACAATTAAA GGAATAGCAA AGGATATAGT AATATTTTC
2341 CAAAACATTT AAATAATTAA CAAAAAAAAA AAAAAAAA AAAAAAAA ATATTAAATA
2401 AATTTTTT TCTTATTATA TGTAACTAAT ATTATTATT AATAAATATA TATATTATAT
2461 AAAGAATAC TAGGATTCT GTATATATAG AAATAAATTC ATTGTATATT ATTATAGAAA
2521 AAAATAAAAA TAAATAATTT CTTTTCTTAG TTGTATTAAT ATCTAAAAA TATAATAAAT
2581 AAAATATAGA AACATTTACA GTATATTTA TAATCTGAAA GTATACATGT AATAAAAAAA
2641 TTTTCTGGCT TTATAATAAT AAATAAGAAA ATTATTATTT TATGTATTAT TTTAAGAAAT
2701 ATTATATATA ATGATAATAA ATGAAAGAAA GAAAAAAAA ATTTTTTAT TATCATTTT
2761 TTCATAAATA TATATAAATA TTATTATATA TAAATACTGG ATAAATATT ATGTATATAT
2821 TTATATATAT ACCATGTTGC CTTTTGGCAT AATGCAATA AAAATATGAA ACAATAAATC
2881 TAIGTTCTGA TTTATATTCT TAGGTAATAA AATTCATATA TATTTTTT AATTTAAAT
2941 ATTTTAAAAC AATGATATA ATTAAAATTA ATTAAAATAA AATAAGAAAA AGTAAGATTT TATAATGTCC
3001 ATAAATTTT TTTTTTTT AGTAGAATAT ATTTAAATAA ATATATATTA TTAAGTTATA
3061 TTATAGTAC TTATTAGTA TAAATAGAGG AATTC
```

Fig. 8

```
  1  EFVESEKSEH EAAENEESSL EEGHHEEIVP EQNNEESGES KLVDNDEGGF EEAHHENFSS
 61  EVSNSELNEN EFVESDKSVT EPAEHEEVVS EESNPEPAEN EESSIEEAHQ EEIVPEQNDE
121  ESGESGLVDN EEGDFEEPNH EEFEPDQNDS ELSENELVES EKSVSEPAEH VEIVSEKSVS
181  EPAEHVEIVS EKSTSEPAEH VESVSEQSNN EPSEKKDGPV PSKPFEEIEK VDVQPKIVDL
241  QIIEPNFVDS QPNPQEPVEP SFVKIEKVPS EENKHASVDP EVKEKENVSE VVEEKQNSQE
301  SVEEIPVNED EFEDVHTEQL DLDHKTVDPE IVEVEEIPSE LHENEVAHPE IVEIEEVFPE
361  PNQNNEFQEI NEDDKSAHIQ HEIVEVEEIL PEDDKNEKVE HEIVEVEEIL PEDKNEKGQH
421  EIVEVEEILP EDDKNEKVEH EIVEVEEILP EDKNEKGQHE IVEVEEILPE DKNEKVEHEI
481  VEVEEILPED KNEKGQHEIV EVEEILPEDK NEKVQHEIVE VEEILPEDKN EKGQHEIVEV
541  EEILPEEDKN EKGQHEIVEV EEILPEDKNE KVQHEIVEVE EILPEDKNEK VQHEIVEVEE
601  ILPEIVEIEE VPSQTNNNEN IETIKPEEKK NEFSVEEKAI PQEPVVPTLN ENENVTPKPS
661  EGESTKPDIV QIKIVQENKP NKKETPVVDG PKHVEQNIQE DDNDEEDDDD IDFEGLSRKD
721  DEKDSSNKNK KKSSFITYIS TKKFKKVSQT IVSVMINAYD GVIQVVSTIK GIAKDIVIFF
781  QNI
```

POOLED - CONCENTRATED

POOLED - CONCENTRATED

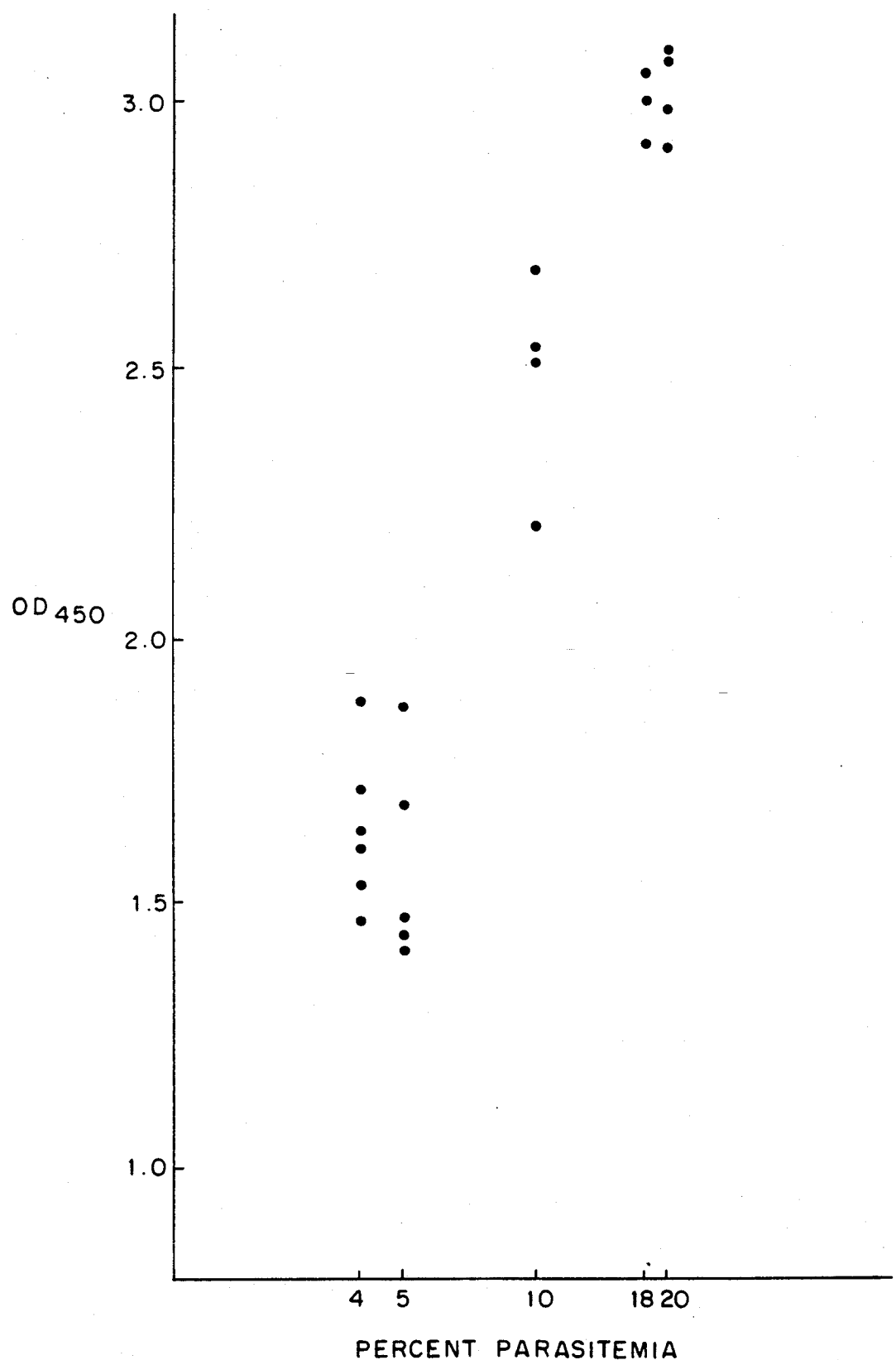

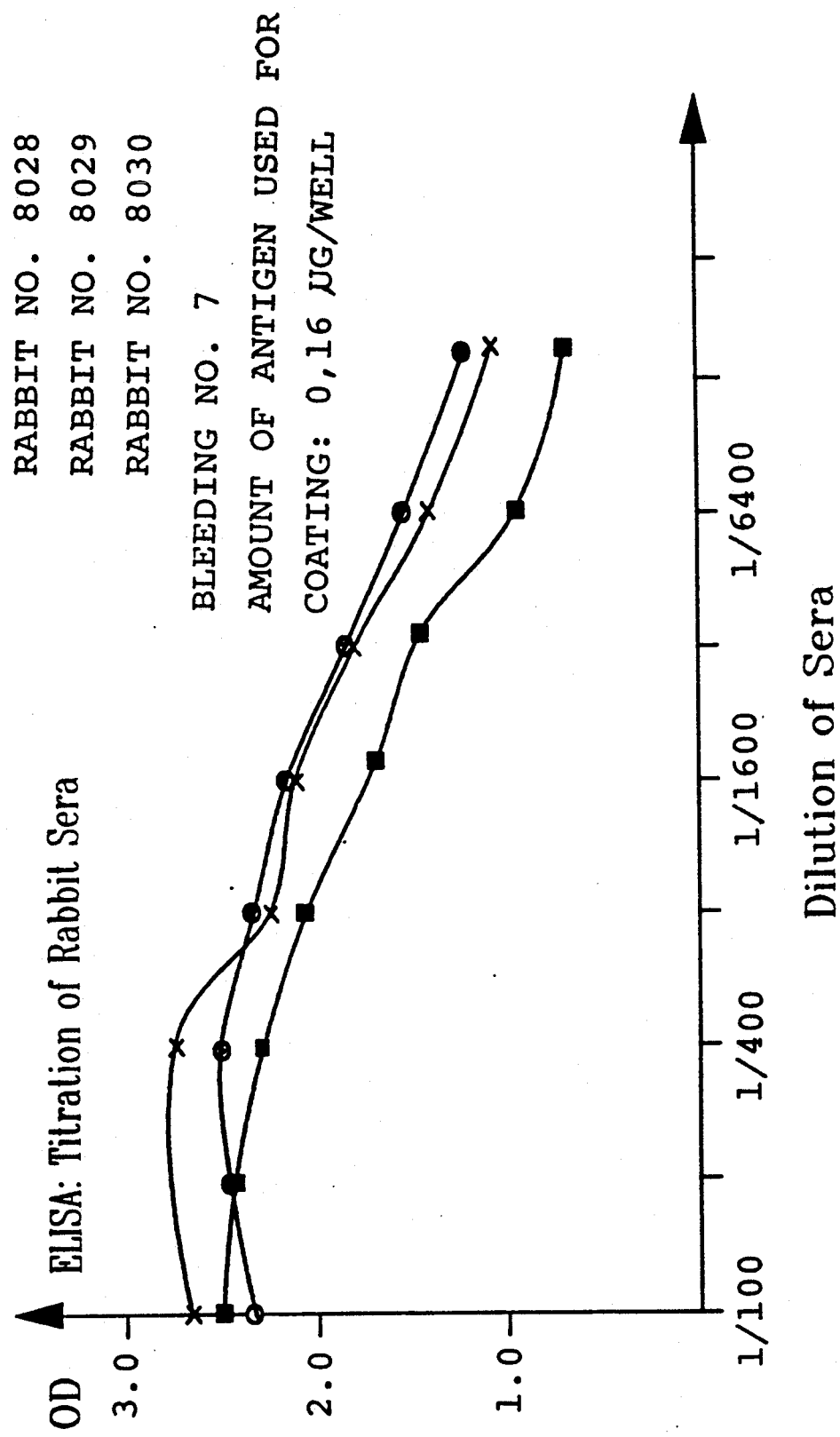

RECIPROCAL DILUTION OF SERUM

RECIPROCAL DILUTION OF SERUM

MALARIA ANTIGEN

This application is continuation-in-part of Ser. No. 07/318,885, field Mar. 3, 1989, now abandoned.

FIELD OF INVENTION

The present invention relates to a polypeptide comprising a characteristic amino acid sequence derived from the *Plasmodium falciparum* antigen GLURP, a polypeptide which is recognized by an antibody raised against or reactive with a polypeptide comprising said characteristic amino acid sequence and/or an antibody reactive with native GLURP, a nucleic acid molecule encoding said polypeptide, an expression vector carrying the nucleic acid molecule an organism expressing said nucleic acid molecule so as to produce said polypeptide, methods of producing and isolating said polypeptide, use of said polypeptide, a monoclonal antibody directed against said polypeptide, a diagnostic agent comprising said antibody or said polypeptide, and the use of said antibody or said polypeptide for diagnostic and therapeutic purposes.

TECHNICAL BACKGROUND

Malaria remains one of the most serious parasitic diseases in the third world despite the efforts to control the disease and reduce its prevalence and continued geographic spread by vector eradication and drug treatment and each year, several hundreds of millions of human beings are affected by the disease. The increasing environmental changes and the failure of classic control programmes have stimulated the search for a vaccine for the control of malaria. Naturally, one of these approaches is immunologic, and for a long time it has been hoped that immunology will provide effective vaccines for malaria. Human malaria is caused by four species of the protozoan genus, Plasmodium. The species *Plasmodium falciparum* is the most dangerous and malignant malaria parasite, causing acute severe infections that are often fatal, especially in young children and immigrants entering endemic areas. Thus, it is very desirable that a vaccine against *P. falciparum* is developed. The life cycle of *P. falciparum* includes different stages; in the first stage, the sporozoite stage, the parasite is brought into the blood stream by the Anopheles mosquito. The sporozoites are carried in the blood stream to the liver where they invade the hepatocytes and develop into merozoites in the course of 5-7 days. Merozoites released from infected cells start a new cycle by invading the erythrocytes. In the erythrocyte, the parasite shows an asexual multiplication which involve a maturation of the parasite through different parasite stages, the ring, the trophozoite and the schizont stage (the stage that undergoes nuclear division). When the schizont infected erythrocyte bursts, new merozoites are released. It is the disintegration of the erythrocyte which gives rise to the clinical disease.

Some merozoites, however, differentiate into gametocytes (microgametocytes and macrogametocytes), the sexual form of the parasite. Contrary to the asexual infected erythrocytes, these sexual parasite stages are able to continue the life cycle, when the infected cells, the erythrocytes, are ingested by mosquitoes during a blood meal. By fertilization in the mosquito gut, the gametocytes develop into a mobile ookinete stage. The ookinete pass through the epithel and matures into a oocyst. In the oocyst, the new sporozoites develop. These sporozoites are released and move to the salivary gland and are then ready to be injected into a new host. The parasites are haploid in most of the life cyclus as they perform a meiotic cell division shortly after fertilization.

The Anopheles mosquito is the primary vector of malaria, but the disease may also be seen after blood transfusion, i.v. injections which contaminated equipment and after transfer from an infected mother to the newborn child through the placenta.

Generally, it has proven difficult or impossible by vaccination to obtain a sufficient immunity against parasitic diseases as such due to the fact that after invasion, many parasites are capable of "cheating" the immune system of an individual by changing the appearance of the antigens or by producing substances which elicit an immune response against other components than the parasites themselves, thereby rendering the immunity obtained by the vaccination insufficient with respect to combating the development of the parasitic infection. Immunization against malaria infections has also been difficult due to the wide variety of existing different malaria parasites.

Parasites of the Plasmodium species, especially *P. falciparum*, are the malaria parasites which have been most intensively investigated. A number of soluble surface proteins and antigens from *P. falciparum*, especially in the schizont stage, have been found in sera from infected individuals (1, 3, 4, 5, 6, 7), and plasma fractions containing these antigens have been isolated and described by Jepsen and Axelsen. Typically, the antigens constitute a heterogeneous group of proteins and glycoproteins. A mixture of soluble *P. falciparum* antigen (antigen 1 and antigen 2) have been isolated form in vitro grown *P. falciparum* (2). None of the antigens 1-7 mentioned in reference 1-7 have, however, separated been isolated and purified, and the antigens have only been characterized by reference to molecular weight, glycosylation and antigenicity, their amino acid composition and possible content of epitopes as well as the nucleic acid molecules encoding the antigens have not been mentioned or indicated.

Nucleic acid sequences encoding polypeptides of various Plasmodium species have been isolated and analysed (8, 9, 10), but none of these nucleic acid sequences encode a polypeptide having a characteristic sequence GLURP and they have all been obtained following a strategy difference from the one used for isolating the DNA-sequence encoding said characteristic amino acid sequence. This will be explained in detailed in the following:

Examples of other works involving *P. falciparum* are described in the following patent publications:

WO 88/00597 (Kara et al.), WO 88/00595 (Epping et al.), WO 86/00620 (Koenen et al.), WO 85/03724 (Hope et al.), WO 85/00975 (Ristic et al.), WO 84/02917 (Kemp et al.), WO 84/02471 (Dubois et al.), WO 84/02472 (Dubois et al.), EP 0 252 588 Smithkline Beckman Corporation), EP 0 209 643 (Eniricerche S.p.A), EP 0 112 784 (Institut Pasteur) GB 21 99 140 (Eniricerche S.p.A.), U.S. Pat. No. 4,735,799 (Patarroyo), U.S. Pat. No. 4,707,357 (Dame et al.) and WO 85/03725 (Mach et al.), GB 2099300 (Freeman et al.), EP 0 223 665 (Vernes et al.), EP 0 136 932 (Chilbert) and EP 0 136 215 (Ristic et al.).

BRIEF DISCLOSURE OF THE INVENTION

In one aspect the present invention relates to a polypeptide comprising a characteristic amino acid sequence derived from the *Plasmodium falciparum* antigen GLURP, which comprises the following sequence:

| | | | | | | |
|---|---|---|---|---|---|---|
| 1 | EFVESEKSEM | EAAENEESSL | EEGHHEEIVP | EQNNEESGES | KLVDNDEGGF | EEAHHENFSS |
| 61 | EVSNSELNEN | EFVESDKSVT | EPAEHEEVVS | EESNPEPAEN | EESSIEEAHQ | EEIVPEQNDE |
| 121 | ESGESGLVDN | EEGDFEEPNH | EEFEPDQNDS | ELSENELVES | EKSVSEPAEH | VEIVSEKSVS |
| 181 | EPAEHVEIVS | EKSTSEPAEH | VESVSEQSNN | EPSEKKDGPV | PSKPFEEIEK | VDVQPKIVDL |
| 241 | QIIEPNFVDS | QPNPQEPVEP | SFVKIEKVPS | EENKHASVDP | EVKEKENVSE | VVEEKQNSQE |
| 301 | SVEEIPVNED | EFEDVHTEQL | DLDHKTVDPE | IVEVEEIPSE | LHENEVAHPE | IVEIEEVFPE |
| 361 | PNQNNEFQEI | NEDDKSAHIQ | HEIVEVEEIL | PEDDKNEKVE | HEIVEVEEIL | PEDKNEKGQH |
| 421 | EIVEVEEILP | EDDKNEKVEH | EIVEVEEILP | EDKNEKGQHE | IVEVEEILPE | DKNEKVEHEI |
| 481 | VEVEEILPED | KNEKGQHEIV | EVEEILPEDK | NEKVQHEIVE | VEEILPEDKN | EKGQHEIVEV |
| 541 | EEILPEEDKN | EKGQHEIVEV | EEILPEDKNE | KVQHEIVEVE | EILPEDKNEK | VQHEIVEVEE |
| 601 | ELPEIVEIEE | VPSQTNNNEN | IETIKPEEKK | NEFSVEEKAI | PQEPVVPTLN | ENENVTPKPS |
| 661 | EGESTKPDIV | QIKIVQENKP | NKKETPVVDG | PKHVEQNIQE | DDNDEEDDDD | IDFEGLSRKD |
| 721 | DEKDSSNKNK | KKSSFITYIS | TKKFKKVSQT | IVSVMINAYD | GVIQVVSTIK | GIAKDIVIFF |
| 781 | QNI | | | | | | or an analogue thereof.

The abbreviations of the amino acids used herein are the following:

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In the present context, the term "characteristic amino acid sequence derived from the *Plasmodium falciparum* antigen GLURP" is intended to mean an amino acid sequence, such as an epitope, which comprises amino acids constituting a substantially consecutive stretch (in terms of linear or spatial conformation) in GLURP, or amino acids found in a more or less non-consecutive conformation in GLURP, which amino acids constitute a secondary or tertiary conformation having interesting and useful properties, e.g. as immunogens. Thus, amino acids present at different positions in GLURP but held together e.g. by chemical or physical bonds, e.g., by disulphide bridges, and thereby forming interesting tertiary configurations are to be understood as "characteristic amino acid sequences". The characteristic amino acid sequence may comprise a consecutive subsequence of the amino acid sequence of GLURP of greater or smaller length or a combination of two or more parts of such subsequences which may be separated by one or more amino acid sequences not related to GLURP. Alternatively, the characteristic amino acid sequences may be directly bonded to each other.

In the present context, the term "epitope" refers to a sequence or subsequence of the polypeptides of the invention or a derivative or an analogue thereof capable of stimulating or interacting with immunocompetent cells, especially epitopes against which antibodies showing desirable properties with regard to diagnosis, prophylaxis or treatment can be raised.

The term "analogue" is used in the present context to indicate a protein or polypeptide of a similar amino acid composition or sequence as the characteristic amino acid sequence derived from the *P. falciparum* antigen GLURP, allowing for minor variations which do not have an adverse effect on the immunogenicity of the analogue. The analogous polypeptide or protein may be derived from a microorganism of another species than *P. Falciparum* or may be partially or completely of synthetic origin. The term is further intended to mean any immunogenic subsequence, functional equivalent or derivative of the characteristic amino acid sequence.

The term "immunogenic subsequence" is intended to indicate an amino acid sequence comprising at least one epitope reactive with an anti-GLURP antibody found in the serum of malaria-immune patients and/or eliciting antibodies which are reactive with native GLURP.

The term "functional equivalent" is intended to include all immunogenically active substances with the ability to evoke an immune response in an animal, including a human being, to which a vaccine containing the equivalent has been administered which is similar to the immune response evoked by the characteristic amino acid sequence of GLURP, e.g. an anti-ideotypic antibody, in that it is able to confer immunity to diseases caused by plasmodial parasites. The functional equivalent may be derived form a microorganism of another species than *P. falciparum* or may partially or completely be of synthetic origin. It should be understood that the similarities between the characteristic amino acid sequence from GLURP and the functional equivalent ar qualitative rather than quantitative, relating to the nature rather than the level of activity of the functional equivalent.

The present invention also relates to a naturally or non-naturally occuring polypeptide which comprises a least one epitope reactive with an antibody which recognizes the *P. falciparum* antigen GLURP. In a such polypeptide said epitope can be a subsequence of the amino acid sequence of GLURP. In another embodiment, the polypeptide and the epitope can have an amino acid sequence substantially homologous with but not identical to the amino acid sequence of GLURP provided that said epitope is reactive with an antibody which recognizes the *P,. falciparum* antigen GLURP.

The antibody used for the recognition of the polypeptide of the invention may be a monoclonal or polyclonal antibody, which have been raised specifically against the polypeptide comprising the amino acid sequence outlined above. Monoclonal or polyclonal antibodies useful for the recognition of the polypeptide of the invention as well as methods of their production are described below. Alternatively, the antibody is obtained form serum obtained from malaria-immune patients, e.g. from the malaria-immune serum pool available from Statens Seruminstitut, Copenhagen, Denmark. The antibody may be obtained from the serum by use of conventional methods, e.g. as described in Material and Methods below.

By the term "recognized" is meant that a reaction between the polypeptide of the invention and the antibodies is observed, when the polypeptide and the antibody is allowed to react under circumstances which allow for such an observation. The reaction may be in the form of a precipitation. An analysis based on the principle of crossed immunoelectrophoresis has been found to be useful in this respect. The crossed immunoelectrophoresis may be carried out substantially as described in (1) and as illustrated in the following examples. Results obtained when subjecting a polypeptide of the invention to crossed immunoelectrophoresis are shown in FIG. 1B.

In another aspect, the invention relates to a nucleic acid molecule comprising a nucleotide sequence encoding the polypeptide described above. The nucleic acid molecule may be used in a method of preparing the polypeptide by recombinant DNA techniques or as a diagnostic agent (i.e. a DNA probe). The use of a nucleic acid molecule of the invention in the production of a recombinant polypeptide (e.g. by inserting the fragment in a suitable vector, transforming the vector into a suitable host microorganism, cultivating the microorganism so as to produce the polypeptide and subsequently recovering the polypeptide form the microorganisms) includes a number of advantages. It is possible to provide large amounts of the polypeptide or any fragment thereof and the polypeptide produced may be isolated in a substantially pure form, free from contaminating substances related to P. falciparum parasites or serum from infected individuals. The nucleic acid molecule of the invention may also be used in a diagnostic agent for the detection of P. falciparum nucleic acid molecule in a sample, which diagnostic agent comprises a labelled nucleic acid molecule which is substantially homologous with a nucleic acid molecule coding for at least part of said polypeptide.

In still another aspect, the present invention relates to a vaccine for immunizing an animal, including a human being, against diseases caused by a plasmodial parasite, which vaccine comprises an immunologically effective and physiologically acceptable amount of a polypeptide as defined above together with a physiologically compatible carrier. The vaccine should be made so as to allow an optimal stimulation of the relevant parts of the immune system, i.e. to present the immunogenic polypeptide for a period of time and in a form being optimal with respect to the recognition, the uptake or any other interaction or processing necessary for the stimulation.

The polypeptide of the invention may be used in the preparation of a monoclonal antibody which is reactive with non-carbohydrate moieties of the polypeptide. The polypeptide of the antibody may be used for the identification and/or quantification of at least part of the above described polypeptide present in a sample thus making it possible to diagnose Plasmodium species-induced diseases. The sample may be any part of a living organism such as a human or an animal containing Plasmodium species molecules, or a specimen obtained from said living organism. The sample may e.g. be a body fluid or tissue part containing the polypeptide, e.g. a tissue sample such as a biopsy, e.g. a liver biopsy, a bone marrow tissue sample, a blood sample, a urine sample, a sample of cerebrospinal fluid, serum, plasma or any product prepared from blood or lymph, secretions or any sample obtained from a human or animal cavity containing Plasmodium species molecules. The sample may also be water, such as tap water, or foodstuffs, such as meat, or may be a vaccine or diagnostic agent in which it is desirable to determine the presence and/or quantity of Plasmodium species molecules. The Plasmodium species molecules to be identified or quantified may be Plasmodium species molecules present on or being a pat of surfaces of cells or within the cells present in the sample.

The term "Plasmodium species molecules" designates any molecule, e.g. a polypeptide present on cell surfaces or being part of cell surfaces of the Plasmodium species as well as any molecules present in the cells such as in the cytoplasm or in the nucleus. Further, Plasmodium species molecules designates molecules being "detached from" or "secreted by" Plasmodium species containing cells, especially form the surface of the cells, and into the extracellular surroundings.

The various aspects of the invention appear from the appended claims. In the following, these aspects are explained in greater details with reference to the claims.

DETAILED DISCLOSURE OF THE INVENTION

The polypeptide of the invention is as mentioned above related to the *P. falciparum* antigen GLURP. The amino acid sequence outlined above constitutes GLURP and is deduced form a nucleic acid sequence which was isolated form a genomic library by screening clones of the library with human malaria-immune sera and with antibodies which had been affinity purified on native antigen 1, a *P. falciparum* protein found in serum of malaria-immune patients.

The antibodies, which were used for the screening, where shown to interact with precipitates representing antigen 1 in a crossed immuno-electrophoresis, and where therefore believed to be mono-specific for antigen 1. Clones in the library reacting with these antibodies were therefore presumed to contain DNA inserts encoding antigen 1 or a part thereof.

The fusion protein which was purified form one of the clones was used for affinity purification of human antibodies specific for the fusion protein. The source of antibodies was an immune Liberian individual possessing high antibody titre against several of the soluble antigens of *P. falciparum*, including antigen 1. Antibodies purified using the fusion protein column were tested in crossed immunoelectrophoresis. It was found that they interacted with all of the precipitates representing antigen 1.

Purified fusion protein was used to immunize rabbits and the resulting rabbit antibodies showed, however, no interaction with precipitates representing antigen 1, but interacted strongly with antigen 3, another *P. falciparum* antigen. By a closer analysis of the antibodies purified on the fusion protein column and their reactivity in a crossed immuno-electrophoresis it was revealed that the antibodies interacted with a precipitate different form antigen 1, which precipitate has now been identified as antigen 3. The reason why this other precipitate was not observed initially is presumed to be due to the fact that the morphology and localization of the precipitate of antigen 3 in this study was very similar to parts of antigen 1. Additionally, the malaria-immune serum used for the second dimension electrophoresis probably did not contain a sufficient amount of antibodies directed against GLURP to produce a visible precipitate by itself, only a deposition of affinity purified antibodies in the intermediate gel caused a precipitation of GLURP. Furthermore, the presence of antibodies directed against antigen 1 in the eluate from the fusion protein column was probably caused by unspecific absorption (see FIG. 1).

By the experiments outlined above, it was indicated that the fusion protein was not partly identical to antigen 1. Later on a partial identify of the fusion protein and antigen 3 was shown by an experiment with crossed immuno-electrophoresis. A more highly purified fusion protein than was initially available (run 3 times on a 900 mm S400HR gel filtration column) was put in the intermediate gel of a crossed immuno-electrophoresis with purified antigens from P. falciparum culture separated in the first dimension and human immune serum in the second dimension gel. Comparison with another crossed immuno-electrophoresis with isotonic saline in the intermediate gel showed that the precipitate designated antigen 3 was incorporated into the precipitate representing the fusion protein, and corresponding to the previous location of antigen 3 in the first dimension resulted in an elevation of the fusion protein precipitate. This last experiment is a direct indication of epitopes shared by antigen 3 and the fusion protein encoded by the DNA insert of the clone. In one embodiment of the invention the polypeptide is cross-reactive with an antibody recognizing Antigen 3 of P. falciparum.

Antigen 1 has not been isolated and purified from the malaria-immune serum and it was not possible to compare the polypeptide of the invention with antigen 1 on the amino acid level or compare the isolated polypeptide with an isolated antigen 1.

Polypeptides of the type described above comprising a considerable amount of hydrophilic and/or acidic amino acids have been found to be of particular interest, especially with regard to their immunogenic properties. It is believed that the hydrophilic and acidic nature of the amino acids is responsible for the establishment of a conformational structure, e.g. a tertiary structure, which is advantageous in exposing the antigenic determinants of the polypeptide and thereby the binding of the polypeptide to a suitable substance, e.g. an antibody, when the polypeptide comprises an antigenic determinant. The considerable amount of hydrophilic and/or acidic amino acids may also be advantageous in the recognition of suitable substances, e.g. antibodies, by the polypeptide.

Preferably, the polypeptide of the invention is substantially pure.

In the present context, the term "substantially pure" is understood to mean that the polypeptide in question is substantially free from other components, e.g. other immunologically active components, which may result from the production and/or recovery of the polypeptide or otherwise be found together with the polypeptide. The high purity of the polypeptide of the invention is advantageous when the polypeptide is to be used for immunization purposes, e.g. as a vaccine constituent, as unwanted and adverse immune reactions resulting from the presence of other immunogenic components are avoided. Also due to its high purity, the substantially pure polypeptide may be used in a lower amount than a polypeptide of a conventional lower purity for most purposes. Further, the immunogenic concentration and/or composition (constituted of the polypeptide of the invention) which is used for a given immunization purpose, e.g. in the form of a vaccine, can be precisely determined. The purity of the polypeptide of the invention can be determined by Western Blot analysis and visualization of the polypeptide by Coomasie brilliant blue staining which will be dealt with in further details in the following.

The sequence of GLURP outlined above is constituted of 783 amino acid residues, which correspond to a molecular weight of 90 kD. The amount of hydrophilic amino acids as well as acidic amino acids is high. The high content of the amino acid glutamate is, however, not a unique feature of a malaria protein. "GLURP" is an abbreviation for glutamate rich protein. In the present context the terminology of the topic DNA and protein is as follows: The DNA-insert from the original λ-phage-clone is termed glurp and the protein encoded hereof is termed GLURP. The fusion protein encoded by the plasmid pRD15, consisting of the N-terminal part of the λCro-protein, the N-terminal part of β-galactosidase and GLURP, is termed β-gal::GLURP (see FIG. 2). The protein from the malaria parasite of which GLURP is believed to be the C-terminal part is called native GLURP.

GLURP has the following amino acid composition:

|   | number | % of the total number of amino acids |
|---|---|---|
| A | 15 | 1.9 |
| C | 0 | 0.0 |
| D | 48 | 6.1 |
| E | 204 | 26.0 |
| F | 18 | 2.2 |
| G | 18 | 2.2 |
| H | 30 | 3.8 |
| I | 61 | 7.7 |
| K | 64 | 8.1 |
| L | 24 | 3.0 |
| M | 1 | 0.1 |
| N | 55 | 7.0 |
| P | 51 | 6.5 |
| Q | 32 | 4.0 |
| R | 1 | 0.1 |
| S | 56 | 7.1 |
| T | 14 | 1.7 |
| V | 89 | 11.3 |
| W | 0 | 0.0 |
| Y | 2 | 0.2 |

The hydropathy of GLURP has been analyzed using the indexes of Kyte and Doolittle (Kyte and Doolittle. J. Mol. Biol. 157:105–132,1982). This shows, that the protein consists of a major predominantly hydrophilic amino terminal part (approximately residue 1–734) and a minor predominantly hydrophobic carboxy terminal part (approximately residue 734–783). The hydropathy is illustrated in FIG. 3.

The net charge of segments of 50 amino acids of the GLURP has been calculated. This shows that the carboxy terminal part starting with residue 732 has a positive charge while the remaining part of the protein has a net negative charge. The net charge of the protein is illustrated in FIG. 4. The predicted hydrophilicity is in agreement with experimental results.

An estimation of the antigenicity of GLURP, based on the principles of Hopp and Woods (Hopp, T. P. and K. R. Woods. Proc Natl Acad Sci USA, 78:3824-3828;1981), which in essence is a prediction of which areas are exposed to water, gives a prediction of good antigenicity of the major part of GLURP (amino acid 1-740). The antigenicity is illustrated in FIG. 5. This is in accordance with a frequent finding of antibodies against GLURP in Africans (as described in Example 4) and illustrated in FIG. 6.

GLURP has a unique primary structure consisting of 3 unique repeats and an interspersed non-repeated sequence. This is also evident from the DNA sequence encoding GLURP, which DNA sequence is illustrated in FIG. 7 and further described below.

The sequence of the first repeat comprises

AENEESSLEEGHNEEIVPEQNNEES-
GESKLVDNDEGGFEE-α, the second repeat comprises

SEKSVSEPAEHVEIV-β, and the third repeat is a 19 or 20 amino acid sequence of the composition EEILPE(E/D/empty)D-KNEK(V/G)(Q/E)HEIVEV-Γ, wherein the bracketed symbols represent different possibilities at the position in question.

Using the symbol Ÿ for a non repeated sequence, the structure of GLURP can be illustrated like this:

ŸαŸαŸββββŸΓΓΓΓΓΓΓΓΓΓΓŸ.

Four potential sites for glycosylation of the type Asn-X-Thr/Ser have been found by the present inventors. They are indicated by the italics and asterisks in the amino acid sequence:

Homology searches have released only limited similarity with other proteins. So far, a 6 amino acid sequence (Glu-Glu-Asn-Lys-His-Ala) (embraced by the symbols < > in the above sequence) common with the Glycophorin Binding Protein-130 has been found by the present inventors. In this protein, the 6 amino acid sequence is amino terminal to the 11 repeats presumed to be involved in the interaction with glycophorin on the surface of the red blood cell (Kochan J. Perkins M. and Parvetch J. V.: Cell, 44;689-696:1986).

In one embodiment of the polypeptide of the invention, the amino acid proline does not occupy position 3 of the substantially repeated subsequence. In another embodiment, the polypeptide of the invention is characterized by having a glutamic acid composition of at least 20% and at the most 1 methione residue and/or no cysteine residues.

The polypeptide of the invention is preferably capable of inducing a proliferative response in a T-lymphocyte. The term "proliferative response" is understood to mean that the T-lymphocyte response to an exposure to a polypeptide of the invention, e.g. antigenic determinant(s) presented by the polypeptide, by producing substances such as interferon and interleukin, which are capable of eliciting an antibody production in B-lymphocytes of the immune system. The proliferative response may be determined by detecting and optionally quantifying the interferon and interleukin produced upon the exposure or by allowing the interferon or interleukin produced to elicit the antibody production from B-lymphocyte and determining the presence and/or amount of the resulting antibodies. As it will be discussed below, a polypeptide (T-cell epitope) eliciting a proliferative response in T-lymphocytes may advantageously be used in combination with a polypeptide (B-cell epitope) being recognizing by antibodies produced by the B-lymphocytes for immunization purposes. The B-cell and T-cell epitopes are further explained below.

By the term "B-cell epitopes" is mean the structures

EFVESEKSEHEA AENEESSLEEGHHEEIVPEQNNEESGESKLVDNDEGGFEEAHHE*N*\*FSS

EVSNSELNENEFVESDKSVTEPAEHEEVVSEESNPEP AENEESSIEEAHQEEIVPEQNDE

ESGESGLVDNEEGDFEE PNHEEFEPDQ*N*\*DSELSENELVE SEKSVSEPAEHVEIV SEKSVS

EPAEHVEIV SEKSTSEPAEHVESVSEQSNNEPSEKKDGPVPSKPFEEIEKVDVQPKIVDL

QIIEPNFVDSQPNPQEPVEPSFVKIEKVPS<EENKHA>SVDPEVKEKE*N*\*VSEVVEEKQNSQE

SVEEIPVNEDEFEDVHTEQLDLDHKTVDPEIVEVEEIPSELHENEVAHPEIVEIEEVFPE

PNQNNEFQEINEDDKSAHIQHEIVEVEEILPEDDKNEKVE HEIVEVEEILPEDKNEKGQ H

EIVEVEEILPEDDKNEKVE HEIVEVEEILPEDKNEKGQ HEIVEVEEILPEDKNEKVE HEI

VEVEEILPEDKNEKGQ HEIVEVEEILPEDKNEKVQ HEIVEVEEILPEDKNEKGQ HEIVEV

EEILPEEDKNEKGQ HEIVEVEEILPEDKNEKVQ HEIVEVEEILPEDKNEKVQ HEIVEVEE

ILPE IVEIEEVPSQTNNNENIETIKPEEKKNEFSVEEKAIPQE PVVPTL NENE*N*\*VTPKPS

EGESTKPDIVQIKIVQENKPNKKETPVVDGPKHVEQNIOEDDNDEEDDDDIDFEGLSRKD

DEKDSSNKNKKKSSFITYISTKKFKKVSQ *TIVSVMI* NAYDG *VIQVV* STIKGIAKD *IVIFF*

QNI

In the above sequence, the fragments in italics indicate hydrophobic amino acids, whereas the bolded fragments indicate repeats.

in the polypeptide which interact specifically with the variable part of an immunoglobulin and thus, the B-cell epitopes are recognized by antibodies produced by the B-cells. The structure of the polypeptide constituting the B-cell epitope may be a stretch of amino acids in the primary sequence of the polypeptide or a group of amino acids which are brought spatially together from parts of the sequence which are not contiguous in the primary sequence, e.g. by means of the secondary or tertiary structure of the polypeptide. Usually, B-cell epitopes contain a rather small number of amino acids, e.g. comprising from about 3 to about 20 amino acids, more usually from about 4 to about 12 amino acids.

The term "T-cell epitopes" is to be understood as the structures in the polypeptide which are presented by antigen-presenting cells and which interact with the T-cell receptor. The interaction between the antigen-presenting cells (i.e. macrophages, B-cells, dendritic cells, interdigitating cells and Langerhans cells) and the T-cell receptor is supped to be mediated in the following manner: The antigen-representing cells internalize the antigens by endocytosis or pinocytosis and subsequent processing by proteolytic cleavage of the antigens to smaller fragments, which are subsequently transformed to the cell surface and presented to the T-cell whereby the interaction between the antigen-presenting cells and the T-cell receptor is established. The processing has been shown to include proteolytic cleavage of the primary structure which produces fragments of the 8-20 amino acids having e.g. an amphifilic α-helical structure. Other alternative ways of processing are evident as it has been shown that a T-cell epitope might be composed of non-contiguous amino acids of the primary structure of the polypeptide. The amphifilic α-helices are then presented on the external cell surface in relation to the molecules of the major histocompatibility complex (class II). The complex of the amphifilic α-helical peptide from the antigen and the histocompatibility molecule is then recognized by T-cells specific for this antigen and triggers the production of lymfokines, growth factors, differentiation factors and some of the corresponding receptors. These substances stimulate the B-cells to produce antibodies against B-cell epitopes related to the T-cell epitope and stimulates natural killer cells (NK cells), filler cells, macrophages and cytotoxic T-cell to engage targets presenting the antigen. Thus, the T-cell epitopes do not in themselves produce antibodies but elicit the antibody production from B-cells inter alia by producing interferon and interleukin which are involved in the stimulation of antibody production of the B-cells. Thus, the T-cell epitopes are not necessarily recognized by the antibodies raised against GLURP. The presence of T-cell epitopes may, however, be illustrated by their capability of inducing a proliferative response in T-cells, i.e. to induce production of interferon and interleukin.

The polypeptides of the invention may solely comprise T-cell epitopes or solely B-cell epitopes or a combination of these. Thus, the composition of the polypeptides of the invention may be tailored to their intended use, e.g. their use as a vaccine component. B-cell epitopes are advantageous for most applications as they are required for eliciting an antibody production. T-cell epitopes are extremely advantageous as they enhance and accelerate the immune response and the production of antibodies. Furthermore, (NB se gammelt koncept) the memory function of the immune system residues in the T-cells. By stimulating this part of the immune system, the antibody production is significant after approximately 5 days. If the memory function is not participating, e.g. in the non-immunized animal, or if the antigen used for immunization does not contain a T-cell epitope, the antibody production is significant after several weeks, consisting primarily of low avidity IgM antibodies and after several months consisting of IgC antibodies of higher avidity.

The amino acid sequences illustrated below are contemplated to constitute suitable T-cell epitopes of GLURP. The sequences have been found by computer analysis of the amino acid sequence illustrated above according to the AMPHI-program (Margalit, H. Spouge, J. L. Cornette, J. L., Cease, K. B. Delisi, C. and Berzofsky, J. A.: Prediction of immunodominant helper T cell antigenic sties from the primary sequence. J Immunol. 138:2213-2239;1987) as described in Example 10. The AMPHI-program predicts sequences having an amphifilic α-helical structure. Several potential sequences have been found. Among these, the following sequences are estimated to be the most interesting using manual construction of helical wheels:

(179-186) Val—Ser—Glu—Pro—Ala—Glu—His—Val;

(162-171) Lys—Ser—Val—Ser—Glu—Pro—Ala—Glu—His—Val;

(194-210) Thr—Ser—Glu—Pro—Ala—Glu—His—Val—Glu—Ser—Val—Ser—Glu—Gln—Ser—Asn—Asn;

(223-230) Lys—Pro—Phe—Glu—Glu—Ile—Glu—Lys;

(333-343) Glu—Val—Glu—Glu—Ile—Pro—Ser—Glu—Leu—His—Glu;

(600-613) Glu—Ile—Leu—Pro—Glu—Ile—Val—Glu—Ile—Glu—Glu—Val—Pro—Ser;

(690-696) Gly—Pro—Lys—His—Val—Glu—Gln.

(739-774) ISTKKFKKVSQTIVSVMINAYDGVIQVVSTIKGIAK

The numbers in brackets are the position in the polypeptide sequence illustrated above and in FIG. 8.

The polypeptide of the invention may be a fusion protein in which characteristic amino acid sequence(s) form GLURP is/are fused to a second amino acid sequence not derived from GLURP. The amino acid sequence to which the characteristic amino acid sequence(s) from GLURP is/are fused may be one which results in an increased expression of the protein by an organism when expressed in the organism, or facilitates or improves the purification and recovery of the fusion protein from said organism in terms of a more easy and economical recovery, e.g. by being easily detectable, e.g. by means of antibodies directed against the sequence or by means of a specific chemical or enzymatic reaction. Further, an amino acid sequence which modifies, e.g. increases the immunogenicity may advantageously be coupled to one or more characteristic amino acid sequences from GLURP so as to adapt the resulting fusion protein for vaccine components.

The fusion protein may comprise β-galactosidase or a part thereof, e.g. The cro-β-galactosidase. An example of a fusion protein according to the invention comprising cro-β-galactosidase is the fusion protein produced by the *E. coli* strain POP 2136 harboring the plasmid pRD15 encoding the fusion protein. This *E. coli* strain has been deposited with Deutsche Sammlung von Mikroorganismen, DSM, in accordance with the Budapest Treaty on Sep. 15, 1988 under the Accession No. DSM 4815. The construct of the plasmid harbored in the deposited strain is illustrated in FIG. 2. The production and characterization of the fusion protein are given in the following Examples and illustrated in the drawings.

In some cases, it may be advantageous to cleave the fusion protein so as to obtain a polypeptide which substantially solely comprises characteristic amino acid sequence(s) from GLURP is/are preferably fused to an amino acid sequence which may be specifically recognized by a cleaving agent, e.g. a chemical such as cyanogen bromide, hydroxylamine and 2-nitro-5-thiocyanobenzoate, or an enzyme, e.g. a peptidase, proteinase or protease, e.g. trypsin, chlostripain, and staphylococcal protease.

Further, the polypeptide of the invention may be coupled to a carbohydrate of a lipid moiety, e.g. a carrier, or modified in other ways, e.g. being acetylated. When produced in a microorganism, e.g. an *E. coli*, the polypeptide of the invention will normally not be acetylated if no special measures are taken. The acetylation may be advantageous as acetylated polypeptides may be more stable in cell, blood or body and tissue fluids. Furthermore, the acetylation may confer the polypeptide with a structure and conformation which mimics the structure and confirmation of the native *P. falciparum* antigen GLURP.

Earlier studies of the *P. falciparum* antigen 3 have revealed that it possibly contains a carbohydrate moiety (7), and that the presence of carbohydrate is important for the reactivity of antigen 3. As explained above, it is presumed that the polypeptide of the invention and antigen 3 share one or more epitopes and it may be advantageous that the polypeptide of the invention is coupled to a carbohydrate moiety in order to more closely mimic the native antigen 3. Several of the *P. falciparum* antigens are believed to be complexes of polypeptide, carbohydrate and lipid moities. Thus, in order to provide the polypeptide of the invention with a structure and conformation which mimics the native structure and conformation of *P. falciparum* antigens, it may be desirable to add lipid or carbohydrate moieties to the polypeptide.

In Example 12 it is demonstrated that the polypeptide of the invention can stimulate the immune system without being modified. In a present preferred embodiment the polypeptide of the invention is in a non-glycosylated form.

Normally, the polypeptide of the invention is derived from a Plasmodium species, preferably *P. falciparum*. Preferably, the Plasmodium species, from which the polypeptide is derived, is in the schizont stage.

The polypeptide of the invention is contemplated to be useful as a prophylactic or therapeutic agent, e.g. a vaccine, or in a diagnostic kit and may be used in the manufacture thereof. This will be explained below.

As mentioned above, one aspect of the present invention relates to a nucleic acid molecule encoding the polypeptide of the invention. In particular, the invention relates to a nucleic acid molecule comprising substantially the following nucleotide sequence:

| | | | | | | |
|---|---|---|---|---|---|---|
| 1 | GAATTCGTTG | AATCGGAAAA | AAGCGAGCAT | GAAGCAGCTG | AAAATGAAGA | AAGTAGTCTT |
| 61 | GAAGAAGCCC | ATCATGAAGA | AATTGTACCT | GAACAAAATA | ATGAAGAATC | AGGTGAAAGT |
| 121 | AAATTAGTTG | ATAATGATGA | AGGTGGTTTT | GAAGAAGCTC | ATCATGAAAA | TTTTTCATCT |
| 181 | GAAGTAAGTA | ACTCTGAATT | AAATGAAAAT | GAATTTGTTG | AATCTGACAA | AAGTGTAACT |
| 241 | GAACCTGCTG | AACATGAAGA | AGTTGTATCT | GAAGAAAGCA | ACCCTGAACC | AGCTGAAAAT |
| 301 | GAAGAAAGTA | GTATAGAAGA | AGCTCATCAG | GAAGAAATTG | TACCTGAACA | AAATGATGAA |
| 361 | GAATCAGGTG | AAAGTGGATT | AGTTGATAAT | GAAGAAGGTG | ATTTTGAAGA | ACCTAATCAT |
| 421 | GAAGAATTTG | AACCTGATCA | AAATGACTCT | GAATTAAGTG | AAAATGAATT | AGTTGAATCA |
| 481 | GAAAAAAGTG | TATCTGAACC | AGCTGAACAT | GTAGAAATTG | TATCAGAAAA | AAGTGTATCT |
| 541 | GAACCAGCTG | AACACGTAGA | AATTGTATCT | GAAAAAAGTA | CATCCGAACC | AGCTGAACAT |
| 601 | GTAGAAAGTG | TATCTGAACA | AAGTAATAAC | GAACCATCCG | AAAAGAAAGA | TGGACCAGTT |
| 661 | CCTTCAAAAC | CATTTGAAGA | AATTGAAAAA | GTGGATGTTC | AACCTAAAAT | TGTAGACCTT |
| 721 | CAAATAATTG | AACCTAATTT | TGTTGACTCA | CAACCAAATC | CACAAGAACC | AGTTGAACCA |
| 781 | TCATTTGTCA | AAATTGAAAA | AGTTCCTTCT | GAAGAAAATA | AACATGCAAG | TGTTGATCCT |
| 841 | GAAGTAAAAG | AAAAAGAAAA | TGTATCTGAA | GTTGTTGAAG | AAAAACAAAA | TTCACAAGAA |
| 901 | TCAGTTGAAG | AAATTCCAGT | AAATGAGGAT | GAATTTGAAG | ATGTTCACAC | TGAACAATTA |
| 961 | GATTTAGATC | ATAAAACAGT | TGATCCAGAA | ATAGTAGAAG | TTGAAGAAAT | TCCTTCAGAA |
| 1021 | CTACATGAAA | ATGAAGTGGC | TCATCCAGAA | ATTGTTGAAA | TTGAGGAAGT | TTTTCCTGAA |
| 1081 | CCAAATCAAA | ATAACGAATT | TCAAGAAATT | AATGAAGATG | ATAAAAGTGC | ACATATTCAG |
| 1141 | CATGAAATAG | TAGAAGTAGA | AGAAATACTT | CCAGAAGATC | ATAAAAATGA | AAAAGTTGAA |
| 1201 | CATGAAATAG | TAGAAGTTGA | AGAAATTCTA | CCAGAGGATA | AAAATGAAAA | AGGTCAACAT |
| 1261 | GAAATAGTAG | AGGTTGAAGA | AATTCTACCA | GAAGATGATA | AAAATGAAAA | AGTTGAACAT |
| 1321 | GAAATAGTAG | AAGTTGAAGA | AAT.CTACCA | GAAGATAAAA | ATGAAAAAGG | TCAACATGAA |
| 1381 | ATAGTAGAGG | TTGAAGAAAT | TCTACCAGAA | GATAAAAATG | AAAAAGTTGA | ACATGAAATA |
| 1441 | GTAGAAGTTG | AAGAAATTCT | ACCAGAAGAT | AAAAATGAAA | AAGGTCAACA | TGAAATAGTA |
| 1501 | GAGGTTGAAG | AAATTCTACC | AGAAGATAAA | AATGAAAAAG | TTGAACATGA | AATAGTAGAA |
| 1561 | GTTGAAGAAA | TTCTACCAGA | AGATAAAAAT | GAAAAAGGTC | AACATGAAAT | AGTAGAGGTT |
| 1621 | GAAGAAATTC | TACCAGAAGA | AGATAAAAAT | GAAAAAGGTC | AACATGAAAT | AGTAGAGGTT |
| 1681 | GAAGAAATTC | TACCAGAAGA | TAAAAATGAA | AAAGTTCAAC | ATGAAATAGT | AGAGGTTGAA |
| 1741 | GAAATTGTAC | CAGAAGATAA | AAATGAAAAA | GTTCAACATG | AAATAGTAGA | GGTTGAAGAA |
| 1801 | ATTCTTCCAG | AAATTGTTGA | AATTGAAGAA | GTACCATCAC | AAACAAATAA | CAATGAAAAT |
| 1861 | ATTGAAACTA | TAAAACCAGA | AGAAAAAAAG | AATGAATTTA | GTGTTGAAGA | AAAAGCAATT |
| 1921 | CCACAAGAAC | CCGTGGTACC | TACATTAAAT | GAAAATGAAA | ACGTTACTCC | CAAACCATGT |
| 1981 | GAAGGTGAAT | CCACTAAACC | AGATATAGTT | CAAATTAAAA | TAGTACAAGA | AAATAAACCA |
| 2041 | AATAAAAAGG | AAACACCAGT | AGTAGATGGT | CCAAAACATG | TAGAACAAAA | TATACAAGAA |
| 2101 | GATGATAATG | ATGAAGAGGA | TGATGATGAT | ATAGATTTTG | AAGGATTATC | AAGAAAAGAT |
| 2161 | GATGAAAAGG | ATTCATCAAA | TAAAAATAAA | AAGAAATCAT | CTTTTATAAC | ATATATATCT |

-continued

| | | | | | | |
|---|---|---|---|---|---|---|
| 2221 ACAAAGAAAT | TTAAAAAAGT | ATCTCAAACT | ATTGTAAGTG | TTATGATTAA | TGCATATGAT | |
| 2281 GGTGTTATTC | AACTTGTAAG | TACAATTAAA | GGAATAGCAA | AGGATATAGT | AATATTTTTC | |
| 2341 CAAAACATTT↓ | AAATAATTAA | CAAAAAAAAA | AAAAAAAAAA | AAAAAAAAAA | ATATTAAATA | |
| 2401 AAATTTTTTT | TCTTATTATA | TGTAACTAAT | ATTATTTATT | AATAAATATA | TATATTATAT | |
| 2461 AAAAGAATAC | TAGGATTTCT | GTATATATAG | AAATAAATTC | ATTGTATATT | ATTATAGAAA | |
| 2521 AAAATAAAAA | TAAATAATTT | CTTTTCTTAG | TTGTATTAAT | ATTCTAAAAA | TATAATAAAT | |
| 2581 AAAATATAGA | AACATTTACA | GTATATTTTA | TAATCTGAAA | GTATAGATGT | AATAAAAAAA | |
| 2641 TTTTCTGGCT | TTATAATAAT | AAATAAGAAA | ATTATTATTT | TATGTATTAT | TTTAAGAAAT | |
| 2701 ATTATATATA | ATGATAATAA | ATGAAAGAAA | GAAAAAAAAA | ATTTTTTTAT | TATCATTTTT | |
| 2761 TTCATAAATA | TTATAAATAA | TTATTATATA | TAAATACTGG | ATAAATATTT | ATGTATATAT | |
| 2821 TTATATATAT | ACCATGTTGC | CTTTTGGCAT | AAATGCAATA | AAAATATGAA | ACAATAAATC | |
| 2881 TATGTTCTGA | TTTATATTCT | TAGGTAATAA | AATTCATATA | TATTTTTTTT | AATTTTAAAT | |
| 2941 ATTTTAAAAC | AAATGATATA | ATTAAAATTA | AATAAGAAAA | AGTAAGATTT | TATAATGTCC | |
| 3001 ATAAATTTTT | TTTTTTTTTT | AGTAGAATAT | ATTTAAATAA | ATATATATTA | TTAAGTTATA | |
| 3061 TTTATAGTAC | TTATTTAGTA | TAAATAGAGG | AATTC | | | | or a subsequence thereof coding for a subsequence of the polypeptide of the invention.

Each of the nucleotides of the above sequence is represented by the abbreviations generally used, i.e.

A represents adenine
T represents thymidine
G represents guanine
C represents cytosine.

It is contemplated that this nucleotide sequence encodes the carboxylic terminal part of native GLURP, due to the fact that an open reading frame of 2349 basepairs extends from the 5'-terminal end of the insert to a "TAA" stop codon (indicated by an arrow in the table above). This is the longest open reading frame found in the nucleotide sequence. No start or initiation codon appears in the reading frame indicating that the above sequence is the 3'-part of the DNA-sequence encoding the carboxyl terminal end of the native GLURP.

The DNA-sequence shown above has been established as described in the following examples.

As it is described in Example 2, the form in which the protein encoded by the above nucleotide sequence was obtained, was as a fusion protein, containing most of the β-galactosidase peptide sequence at the amino terminal end. In the above nucleotide sequence, the nucleic acid sequence encoding GLURP is presumed to terminate at position 2349 where a stop codon is found (indicated by an arrow). The remaining part of the sequence is non-coding.

The fusion protein encoded by the above nucleotide sequence was tested with respect to its antigenic properties as described in Examples 3 and 4. The reactivity of the nucleic acid sequence product with the malaria-immune sera and the nonreactivity with the sera of Danish donors (not presumed to be malaria-immune) strongly suggest that the reading frame extending in phase with that of the lacZ of the pEX2 vector is the one used in vivo by *P. falciparum*.

The Southern Blot performed with different isolates of *P. falciparum* (Example 1) shows that the nucleic acid sequence is widely distributed (see FIG. 12). Although the present inventors generally observe a polymorphism of the restriction fragment lengths, there seems to be a certain conservation of the nucleic acid sequence as evidenced by the observation of a pattern common for the isolates from Thailand and Burma and another pattern common for several African isolates. The relative conservation and the wide geographical distribution indicates that this nucleic acid sequence is of importance for the parasite.

The nucleic acid sequence displays some of the characteristics of other malaria nucleic acid sequences. Tandemly repeated motifs, high AT content (Hyde, John E. and Sims, P. F. G., 1987, Gene (61), pp. 177-187) and a corresponding preference for codons containing these bases, and a high content of codons for glutamate.

The respective regions are indicated in the homology matrix, FIG. 9, as lines of dots appearing parallel to the diagonal representing the homology of the sequence with itself.

The figure illustrates the three major regions of repetitive sequence: one motif from bp 34 to bp 156 is repeated from bp 289 to bp 411; another motif from bp 477 to bp 521 is repeated tandemly twice from bp 522 to bp 566 and from bp 567 to bp 611; a third motif from bp 1174 to bp 1233 is repeated tandemly 11 times. This last repetitious region consists of 3 60 bp repeats and 8 57 bp repeats differing only in the 3 bases GAT coding for the amino acid aspartate. This region is flanked to the 5' terminal of a degenerated 60 bp repeat.

The GC content of the coding part of the insert (shown in FIG. 10) is on the average 30%, and of the non coding 3' terminal 11% in accordance with the above mentioned previous analyses of malaria DNA.

Hybridization is a useful method to compare the homology of GLURP to the sequence of a given DNA-molecule. Hybridization may be performed as follows: Pure DNA comprising the nucleic acid sequence encoding GLURP from the plasmid pRD15 in POP2136 is prepared using the large scale method described in Maniatis et al. op cit., page 86-96. More specifically, glurp is excised from the plasmid by digestion of the plasmid DNA with EcoRI. The insert is then separated from the plasmid DNA by use of agarose gel electrophoresis. The insert is labelled by any labelling principle, such as the ones disclosed herein. The foreign DNA to be examined is coupled to a matrix, e.g. a nitrocellulose filter. The filter is subjected to a suitable treatment suited to the kind of matrix employed so as to couple the DNA to the matrix, in the case of a nitrocellulose filter e.g. by baking the filter at a temperature of 80° C. for 2 hours. The membrane is exposed to a prehybridization solution of a composition, at a temperature and for a period of time recommended suited to the membrane in question. The membrane is then placed in the hybridization solution containing the labelled denatured DNA probe obtained from the pRD15 plasmid (glurp). Hybridization is preferably carried out over night at a suitable temperature. The membrane is then washed and incubated with a volume of 50 ml 2×SSC at 65° C. for 30 minutes.

The procedure is repeated one. The membrane is then incubated in 15 ml 2×SSC containing 0.1% SDS. Incubation is performed at 65° C. for 30 minutes. All incubations including prehybridization and washings are performed with gentle agitation. The filter is air-dried and wrapped in a suitable plastic wrap (e.g. Saran Wrap), the filter is then applied to an x-ray film so as to obtain an auto-radiographic image. Exposition is preferably carried out at −70° C. with intensifying screens for a period of time which is determined by the positive control used. Any hybridization of glurp to the DNA is an indication of similarity of the sequences of the two nucleic acid molecules, i.e. that the DNA is a nucleic acid molecule of the invention. Another approach of determining similarity between DNA molecules is by determining the nucleotide sequence of the DNA molecule to be compared with glurp or a subsequence of glurp by conventional DNA sequencing analysis, and comparing the degree of homology with the chosen subsequence of glurp. In the same way, the homology of a given DNA sequence to the complementary DNA-sequence of glurp can be determined. Preferably, a degree of homology of at least about 70%, e.g. at least about 80% such as at least about 95% is obtained.

The nucleic acid sequence of the invention may comprise a nucleic acid sequence fused to another nucleic acid sequence encoding a characteristic amino acid sequence with the purpose of producing a fused polypeptide, e.g. The fusion protein illustrated in the Examples, as explained above. When using recombinant DNA technology, the fused sequence may be inserted into an appropriate vector which is transformed into a suitable host microorganism. Alternatively, the nucleic acid molecule of the invention may be inserted in the vector in frame with a nucleic acid sequence carried by the vector, which nucleic acid sequence encodes a suitable polypeptide. The host microorganism is grown under conditions ensuring expression of the fused sequence after which the fused polypeptide may be recovered from the culture by physico-chemical procedures, and the fused polypeptide may be subjected to gel filtration and affinity chromatography using an antibody directed against the antigenic part(s) of the fused polypeptide to which it is fused may be separated, for instance by suitable proteolytic cleavage, and the polypeptide of the invention may be recovered, e.g. by affinity purification or another suitable method.

In another embodiment, a nucleic acid molecule of the invention is substantially complementary to at least a substantial portion of the nucleic acid molecule of FIG. 7.

The DNA-fragment may also comprise a suitable nucleotide sequence controlling the expression and replication of the nucleic acid molecule. The regulatory nucleotide sequence is conveniently a part of the expression vector used for the production of the polypeptides, when such a vector is employed.

Analogous to the explanation of the polypeptide of the invention given above, the nucleic acid molecule of the invention preferably contains a considerable number of codons corresponding to hydrophilic and/or acidic amino acids, e.g. codons corresponding to the amino acids glutamic acid and aspartic acid.

The nucleic acid molecule described above may be obtained from Plasmodium species parasites, e.g. from chromosomal or genomic DNA or by reverse transcriptase producing cDNA. When obtaining he nucleic acid molecule form chromosomal or genomic DNA, it is preferably derived directly from the parasite genome, e.g. by screening for genomic sequences, hybridizing to a DNA probe prepared on the basis of the full or partial nucleic acid sequence of glurp. When the DNA is of complementary DNA (cDNA) origin, it may be obtained by preparing a cDNA library on the basis of mRNA from cells producing GLURP or parts thereof. Hybridization experiments may then be carried out using synthetic oligonucleotides as probes to identify the cDNA sequence encoding GLURP or part thereof. cDNA differs from genomic DNA in, e.g. that it lacks certain transcriptional control elements and introns which are non-coding sequences within the coding DNA sequence. These elements and introns are normally contained in the genomic DNA. The nucleic acid molecule may also be of synthetic origin, i.e. prepared by conventional DNA synthesizing method, e.g. by using a nucleotide synthesizer. The nucleic acid molecule may also be produced using a combination of these methods.

In a further aspect, the invention relates to an expression vector which is capable of replicating in a host organism and which carries a nucleic acid molecule as described above and is capable of expressing the polypeptides described above. In this embodiment the expression vector is capable of replicating in a host organism and of expressing therein a polypeptide which comprises at least one epitope reactive with an antibody which recognizes the *P. falciparum* antigen GLURP, such as an expressed peptide which is substantially homologous with a substantial portion of the polypeptide, the amino acid sequence of which is shown in FIG. 8.

The vector may be any vector which may conveniently be subjected to recombinant DNA procedures, and the choice of vector will often depend on the host cell into which it is to be introduced. Thus, the vector may either be one which is capable of autonomous replication, i.e. a vector which exists as an extrachromosomal entity, the replication of which is independent of chromosomal replication, such as a plasmid, or one which is replicated with the host chromosome, such as a bacteriophage.

When a microorganism or a mammalian cell line is used as the host organism, examples of useful vectors are plasmids such as natural or synthetic plasmids, e.g., plasmids related to pBR322 such as pEX 1–3, the pRIT-family, the pUC-family and the like, and viruses such as adenovirus, vaccinia, retrovirus, Baculo virus, Epstein-Barrvirus, SV40-related virus and bovine papilloma virus. Examples of suitable bacteriophages include M13 and lambda.

The invention also relates to an organism which carries and is capable of expressing a nucleic acid molecule as defined above and which not in its native form expresses said nucleic acid molecule. The nucleic acid molecule may be carried on a vector as described above or may be integrated in the genome of the organism. Examples of suitable organisms include microorganisms such as bacteria, e.g. bacteria of the genus Bacillus, e.g. *B. subtilis*, Escherichia, e.g. *E. coli*, or Salmonella; yeasts, fungi, protozoa, insect cells and higher eucaryotic organisms or cells including plant and mammalian cells. However, also higher organisms such as animals, e.g., sheep, cattle, goats, pigs, etc. are contemplated to be useful as hot organisms for the production of the polypeptide of the invention.

The present invention also relates to a method of producing the polypeptides described above. Suitably, the polypeptides are prepared using recombinant DNA-technology e.g. the methods disclosed in Maniatis et al. op cit. More specificlaly, the polypeptides may be produced by a method which comprises cultivating or breeding an organism carrying a DNA-fragment encoding a characteristic amino acid sequence form GLURP, e.g. the above described nucleic acid molecule, under conditions leading to expression of said nucleic acid molecule, and subsequently recovering the polypeptide from the organism.

As described above, the organism which is used for the production of the polypeptide may be a higher organism, e.g. an animal, or a lower organism, e.g. a microorganism. Irrespective of the type of organism employed for the production of the polypeptide, the nucleic acid molecule encoding the characteristic amino acid sequence from GLURP should be introduced in the organism. Conveniently, the nucleic acid molecule is inserted in an expression vector, e.g. a vector as defined above, which is subsequently introduced into the host organism. The nucleic acid molecule may also be directly inserted in the genome of the host organism. The insertion of the nucleic acid molecule in the genome may be accomplished by use of a virus, such as a bacteriophage, carrying the nucleic acid molecule and being capable of mediating the insertion into the host organism genome. The insertion of the nucleic acid molecule into an expression vector or into the genome of the host organism may be accomplished as described e.g. by Colbere-Garapin F. et. al., J. Molec. Biol., 150; 1–14 (1981): A New Dominant Hybrid Selective Marker for Higher Eucaryotic Cells.

Similarly, when using an expression vector for the production of the polypeptide of the invention, the nucleic acid molecule may be inserted in frame with a second nucleic acid molecule encoding another polypeptide so as to obtain an expression of fusion protein.

When the polypeptide of the invention comprises one or more distinct parts, e.g. being a fusion protein comprising on the one hand characteristic amino acid sequence(s) from GLURP and on the other hand amino acid sequence(s) constituting a polypeptide which is not related to GLURP, the nucleic acid molecules encoding each of these polypeptides may be inserted in the genome or expression vector separately or may be coupled before insertion into the genome or expression vector by use of conventional DNA techniques such as described in Maniatis et al. op cit.

The conditions under which the organism producing the polypeptide of the invention is cultured or bred should of course be adapted to the organism employed. Conventional cultivation and breeding techniques may be employed. In the case of microorganism, cultivation is e.g. carried out in a culture medium conventionally used for fermentation purposes, e.g. Luria Broth medium, and under conditions with respect to pH, temperature, aeration, etc. suited to the type of microorganism in question, e.g. as disclosed in Maniatis et al. op. cit.

Subsequent to the expression of the polypeptide in the host organism, the polypeptide is recovered or isolated form the organism. The polypeptide may be isolated or recovered form the culture by a method comprising one or more affinity chromatography and/or size chromatography steps, and optionally employing a step using an antibody reactive with and/or being raised against said polypeptide. The procedure used for recovering of the polypeptide depends on the kind of host organism used as well as the polypeptide produced.

When the polypeptide of the invention is produced using microorganisms as a host organism, the recovery and isolation of the polypeptide will also of course depend on the kind of microorganism employed. Suitably, the recovering of the polypeptide from the microorganism comprises treatment of the microorganism so as to release the polypeptide, e.g. by rupturing the microorganism, i.e. partly or totally, and subsequently recovering the polypeptide by well-known methods such as precipitation, gel filtration, ion exchange chromatography, or HPLC reverse phase chromatography or immuno affinity chromatography or the like.

More specifically, the polypeptide of the invention may be isolated from a biological material containing the polypeptide, e.g. a suspension of cells producing the polypeptide, e.g. a suspension of cells producing the polypeptide, by use of a method comprising adsorbing the biological material to a matrix comprising an immobilized monoclonal or polyclonal antibody as described herein, eluting the polypeptide from the matrix, and recovering the polypeptide from the eluate. Examples of procedures for isolating the polypeptide are:

a) A procedure employing antibodies reactive with Plasmodium species molecules which is suited for the obtainment of a Plasmodium species containing fraction with high purity, especially a fraction which contains molecules of the species *P. falciparum*, especially in the schizont stage. The procedure may be performed by immobilizing the specific antibodies, preferably monoclonal antibodies, to a matrix, contacting said matrix with the preparation containing the released Plasmodium species molecules, washing, and finally treating the antigen-antibody complex fixed to the matrix so as to release the Plasmodium species molecules in a purified form. A preferred way is to isolate the Plasmodium species molecules by means of column affinity chromatography involving antibodies fixed to the column matrix.

b) Procedures involving various forms of affinity chromatography, gel filtration, ion exchange or high performance liquid chromatography (HPLC).

c) Preparative electrophoresis procedures; for instance the following procedure: A supernatant from a centrifuged enzyme treated cell or cell line preparation is subjected to a gel electrophoresis, such as a sodium dodecyl sulphate-polyacrylamidgel electrophoresis (SDS-PAGE) (cf. Laemmli, U. K. Nature, 227:680–685; 1970, supra) or an agarose gel electrophoresis. Subsequently, labelled antibodies, such as monoclonal antibodies, reactive with Plasmodium species, are sued to identify bands primarily constituted by the isolated Plasmodium species molecules. For instance, the antibodies may be used in any conventional immunoblotting technique. The markers may be isotopes or fluorescein labels detectable by means of relevant sensitive films. After identification, the Plasmodium species containing bands of the gel may be subjected to a treatment resulting in the release of the Plasmodium species molecules form the gels, such as procedures involving slicing up the gel and subsequent elution of Plasmodium species molecules. Optionally, the amino acid sequence of the Plasmodium species proteins obtained may be determined.

Prior to cultivation of the microorganism, the nucleic acid molecule encoding the polypeptide of the invention may be subjected to modification, before or after the nucleic acid molecule has been inserted in the vector. The polypeptide produced may also be subjected to modification. The modification may comprise substitution, addition, insertion, deletion or rearrangement of one or more nucleotides and amino acids in the nucleic acid molecule and the polypeptide, respectively, or a combination of these modifications. The term "substitution" is intended to mean the replacement of any one or more amino acids or nucleotides in the full amino acid or nucleotide sequence with one or more others, "addition" is understood to mean the addition of one or more amino acids or nucleotides at either end of the full amino acid or nucleotide sequence, "insertion" is intended to mean the introduction of one or more amino acids or nucleotides within the full amino acid or nucleotide sequence, and "deletion" is intended to indicate that one or more amino acids or nucleotides have been deleted form the full amino acid or nucleotide sequence whether at either end of the sequence or at any suitable point within it. "Rearrangement" is intended to indicate that one or more amino acids or nucleotides or the sequence has been exchanged with each other. The nucleic acid molecule may, however, also be modified by subjecting the organism carrying the nucleic acid molecule to mutagenization, preferably site directed mutagenization so as to mutagenize said fragment. When the organism is a microorganism, the mutagenization may be performed by using conventional mutagenization means such as ultraviolet radiation, ionizing radiation or a chemical mutagen such as mitomycin C, 5-bromouracil, methylmethane sulphonate, nitrogen mustard or a nitrofuran or mutagens known in the art, e.g., mutagens of the type disclosed in Miller, J. H., Molecular genetics, Unit III, Cold Spring Harbour Laboratory 1972.

Examples of suitable modifications of the DNA sequence are nucleotide substitutions which do not give rise to another amino acid sequence of the protein, but which, e.g., correspond to the codon usage of the specific organism in which the sequence is inserted; nucleotide substitutions which give rise to a different amino acid sequence and therefore, possibly, a different protein structure without, however, impairing the critical properties of the polypeptide encoded by the DNA sequence; a subsequence of the DNA sequence shown above encoding a polypeptide which has retained the immunogenic properties of the native GLURP; or a DNA molecule hybridizing to at least part of a DNA molecule prepared on the basis of the DNA sequence shown above, provided that it encodes a polypeptide which has the biological property of native GLURP.

The polypeptide produced as described above may be subjected to posttranslational modifications such as for instance thermal treatment, treatment with a chemical such as formaldehyde, glutar aldehyde or a sutialbe proteolytic enzyme, e.g. a peptidase or proteinase, such as trypsin, and substitution, addition, insertion, deletion, or rearrangement of one or more amino acids in the polypeptide.

The posttranslational modification of the polypeptide may serve the purpose of adapting the polypeptide to a specific use, e.g. as a component in the vaccine such as descried herein.

It is well-known that use of recombinant DNA-techniques may be associated with another kind of processing of the polypeptide than the processing of the polypeptide when produced in its natural environment. Thus, when a bacterium such as E. coli is used for the production of the polypeptide of the invention, the amino acid residues of the polypeptide are not glycosylated, whereas the polypeptide may be glycosylated when produced in another microorganism or organism. The lack of glycosylation of the polypeptide produced by the E. coli strain DSM 4815 has been found not to affect the immunogenic and antigenic properties β-gal::-GLURP (see Example 3, 4 and 12) in any substantial manner; the polypeptide shows the characteristic reaction, e.g. it precipitates with antibodies obtained from serum from malaria-immune patients. This is illustrated in the following examples. However, it may be advantageous to remove or alter the processing characteristics caused by the host organism in question, and posttranslational modification of the polypeptide as well as the DNA sequence may serve this purpose.

Also, the polypeptide of the invention may e prepared by the well-known methods of liquid or solid phase peptide synthesis utilizing the successive coupling of the individual amino acids of the polypeptide sequence or the coupling of individual amino acids forming fragments of the polypeptide sequence which fragments subsequently are coupled so as to result in the desired polypeptide. The solid phase peptide synthesis may e.g. be performed as described by R. B. Merrifield, *J. Am. Chem. Soc.* 85, 1963, p. 2149. In sold phase synthesis, the amino acid sequence is constructed by coupling an initial amino acid to a solid support and then sequentially adding the other amino acids in the sequence by peptide bonding until the desired length has been obtained. In this embodiment, the solid support may also serve as the carrier for the polypeptide of the invention in a vaccine preparation as described below. The preparation of synthetic peptides for use as vaccines or for diagnostic purposes may be carried out essentially as described in Shinnick, *Ann. Rev. Microbiol.* 37, 1983, pp. 425–446.

The present invention also relates to a vaccine for immunizing an animal, including a human being, against diseases caused by a plasmodial parasite, which vaccine comprises an immunologically effective and physiologically acceptable amount of the polypeptide of the type described above together with a physiologically compatible carrier.

The term "vaccine" is to be understood to comprise any preparation containing an immunologically effective part of Plasmodium species molecules suited for administration to living organisms for the prevention, amelioration or treatment of Plasmodium species infection. Preferably, the plasmodial parasite is a *P. falciparum*. The term "immunization" is understood to comprise the process of evoking a specific immunologic response with the expectation that this will result in humoral, and/or secretory, and/or cell-mediated immunity to infection with Plasmodium species, i.e. immunity is to be understood tom comprise the ability of the individual to resist or overcome infection or to overcome infection "more easily" compared to individuals who have not been immunized or to tolerate the infection without being clinically affected or to block transmission. Thus, the immunization according to the present invention is a process of increasing resistance to infection with Plasmodium species. An overall aspect in the preparation of the vaccines of the invention is the physiological acceptability of the components and of the total composition of the vaccine. The final formulation of the vaccine should be a mixture of substances supporting and enhancing the immune response induced by the specific immunogenic component.

The vaccines of the present invention may suitably be provided as a sporozoite vaccine, merozoite and/or gamete vaccine. The terms refer to the various stages of the life cycle of the malaria parasite described above. These stages may be targeted for immunological attack by a vaccine.

In a preferred embodiment of the invention a vaccine is developed which is strain-non-specific, i.e. it comprises an epitope which is a protective epitope common to substantially all strains of the Plasmodium species causing infections of considerable clinical importance. In this case, an epitope according to the present invention being conserved in different Plasmodium species is advantageous.

In another preferred embodiment of the invention, a multivalent vaccine is formulated, i.e. several immunologically effective components are incorporated into a single vaccine being effective in reducing infection, and/or transmission—all in all inducing an effective protective immunity. The vaccine may comprise one or more additional molecules which are not related to GLURP in order to provide the multivalent nature of the vaccine. Especially interesting additional molecules are immunologically active molecules obtained from pathogenic organisms other than Plasmodium species organisms which give rise to a vaccine being effective in reducing infection or providing immunity for one or more pathogenic organisms in addition to the plasmodial parasite.

In the production of the various vaccine types, the fact that cloned DNA sequences can be used for the synthesis of proteins and peptides is used. A major advantage of this strategy is the ability to produce an unlimited amount of a purified product and the avoidance of contamination by pathogens. Production can be carried out as described above, e.g. in a microorganism such as in bacteria or in yeast. Alternatively, liquid or solid phase synthesis can be used. Routine methods for vaccine production involve risks of obtaining unwanted side effects, e.g. due to the vaccine containing unwanted (or even unidentified) contaminants. The methods of preparation of vaccines according to the present invention are designed to ensure that the identity and immunological effectiveness of the specific molecules are maintained and that no unwanted microbial contaminants are introduced. The final products are distributed under aseptic conditions into preferably sterile containers which are then sealed to exclude extraneous microorganisms.

The vaccine may further comprise an adjuvant in order to increase the immunogenicity of the vaccine preparation. The adjuvant may serve the purpose of enhancing the stimulatory properties of the polypeptide by stimulating the production of cytokines or lymphokines from the cells of the immune system in a non-specific way. The adjuvant may be selected from the group consisting of Freund's incomplete adjuvant (see Examples 12A and 12C), aluminium hydroxide (see Examples 12B and 12C), a saponin, a muramyl dipeptide, a lipopolysaccharide, a T-cell immunogen, inerleukin-2, interferon-gamma, an oil, such as a vegetable oil, e.g. peanut oil, or a mineral oil, e.g. silicone oil, and B.C.G.

Another vaccine form is contemplated to be useful as it improves the transportation of the vaccine and the physical-chemical presentation, and prolongs the tie of presentation for the relevant parts of the immune system. Such vaccine comprises a vehicle which may be in various forms. The vaccine may comprise polypeptides incorporated into micelles, (using micelle-forming agents such as detergents, preferably non-ionic detergents or other non-denaturating micelle-forming agents such as amphiphilic peptides, glycosides), open spherical structures, consisting of circular subunits or parts of spherical structures, the formation of which utilizes the hydrophobic/hydrophilic properties of the polypeptides are incorporated into so-called iscoms (immune stimulating complexes, as disclosed, e.g., in EP 0 109 942).

The polypeptide of the invention may advantageously be coupled to a carrier, which may be any carrier usually employed in the preparation of vaccines. The carrier may be a macromolecular carrier, e.g. comprising polysaccharides or polypeptides to which the polypeptide is covalently or non-covalently bound. The carrier should preferably be non-toxic and non-allergenic. The polypeptide may be multivalently coupled to the macromolecular carrier as this provides an increased immunogenicity of the vaccine preparation. In this regard, it may prove advantageous to couple the polypeptide to the carrier together with one or more immunologically active molecules obtained from organisms other than plasmodium species so as to obtain a vaccine comprising a variety of different immunogenic determinants, i.e. a cocktail vaccine, which may be employed for the immunization of diseases caused by a variety of different organism. A vaccine, wherein the polypeptide is polymerized, i.e. so as to present the polypeptide in a multivalent form, may also provide advantageous.

Various immunization schedules may be employed when using the vaccine of the invention: In some instances it may be appropriate to provide active immunization early in life. Furthermore, it may be desirable to employ repeated administrations, e.g. at regular or prolonged intervals, optionally—as far as injections are concerned—at various body sites, e.g. at the same time. Any immunization schedule which may be contemplated or shown to produce an appropriate immune response can be employed in accordance with the principles of the present invention.

The vaccine should be administered in a way which ensures an efficient stimulation of the immune system. This means that the vaccine should be brought into contact with the cells of the immune system for a sufficient period of time and in a form capable of functioning as an immunogen. Several ways are possible. Of these, the most conventional are the parenteral ways, i.e., the subcutaneous, intradermal, intramuscular or the intravenous route.

Other more unusual ways of administering the vaccine are the nasal, the oral or the rectal routes. A combination of the two, first mentioned routes could be achieved by using an aerosol formulation of the vaccine to be administered via the respiratory tract. This formulation of a vaccine has been proposed for special purposes where a more conventional formulation would be insufficient due to: the need for vaccination in very remote areas, the logistic problems associated with transportation and storage of the vaccine, problems associated with infections being spread by multiple use of syringes, and the need to vaccinate large populations.

The aerosol vaccine is in most cases administered via the nasal route. It is known that peptides can be transported intactly through the nasal mucosa to reach the blood. When transported further down the respiratory tract, the antigen is taken up by the macrophages functioning as scavengers and is in this way potentially presented to the immune system. Some of the material administered as an aerosol may possibly reach the intestines and stimulate the immune system present in the intestines and this way stimulate the immune system of the body, or may be taken up by the intestinal mucosa in intact form and liberated to the blood stream where it will be presented for the immune system.

The vaccine may also be administered strictly via the nasal route. This way simplifies the administration and circumvents the problems associated with spreading of infectious diseases through multiple use of syringes.

The oral route of administrating the vaccine utilizes the finding, that certain proteins are taken up by the intestinal mucosa and are found in intact form in the bloodstream. This special way of administering the vaccine will take advantage of pharmaceutical formulations protecting the immunogenic components from degradation in the stomach or in the intestines. An effect of administrating the vaccine via the oral route may also come from the polypeptide stimulating that part of the immune system which is residing in the intestines and in the liver—and this way leading to a general immune stimulation.

The rectal route of administering the vaccine has the same advantages as the above-mentioned methods but might be more reliable, and thus, lead to greater patient compliance in special groups, i.e. children.

In a further interesting aspect, the present invention relates to a non-pathogenic microorganism which caries and is capable of expressing an inserted nucleotide sequence coding for a polypeptide of the invention for use as a live vaccine for the immunization of an animal, including a human being, against diseases caused by malaria parasites. The use of a live vaccine might be advantageous since there is some indication that vaccines based on living organisms shown excellent immunogenicity, often conferring a lifelong immunity against the disease in question. Live vaccines also tend to be less expensive to produce than those based on a purified protein, no purification step being required. The polypeptide of the invention may advantageously be expressed on the outer surface of the non-pathogenic organisms. This provides a favorable presentation of the polypeptide which will be recognized by the immune defense mechanisms of the animal to which the live vaccine is administered, thus, provoking an appropriate immune response.

Given the special formulation of the vaccine as a recombinant organism, i.e. a bacteria such as of the genus Escherichia or Salmonella, this route could allow the bacteria to become established in the intestines and/or in the liver—and, thus, provide the patient with a prolonged immune stimulation.

Alternatively, one or more DNA sequences encoding antigens could be inserted into a virus genome, e.g. into a retrovirus, vaccinia, Epstein-Barr virus genome, to produce a polyvalent vaccine. A DNA sequence encoding for a characteristic amino acid sequence related to Plasmodium species molecules and/or an immunologically equivalent or derivative thereof could be recombined with vaccinia to yield a vaccine to protect against infection with Plasmodium species.

In another aspect of the invention, passive immunization is employed, i.e. a preparation containing antibodies, e.g. of the type described below, especially a preparation with a high content of purified antibodies, is administered. In another preferred embodiment of the invention, a mixture of two or more single vaccines is employed.

Another aspect of the invention is a monoclonal or polyclonal antibody specific for a Plasmodium species molecule such as the *P. falciparum* antigen GLURP or a polypeptide as described above, and a method for the preparation thereof. The term "antibody" may refer to a substance which is formed by an animal or animal cell belonging to the immune system as a response to exposure to the polypeptides of the invention.

The variant domain of an antibody is composed of variable and constant sequences. The variant part of the domain is called the idiotype of the antibody. This part of the antibody is responsible for the interaction with the antigen, the antigen binding.

The idiotypic structure is antigenic and can thus give rise to specific antibodies directed against the idiotypic structure. This has been done in mice. The antibodies raised against the idiotype, the anti-idiotypic antibodies, may mimic the structure of the original antigen and therefore may function as the original antigen to raise antibodies reactive with the original antigen. This approach may be advantageous as it circumvents the problem associated with the characterization and synthesis of the important immunogenic parts of the protein in question. This is most important in the case of conformational epitopes, which might otherwise be difficult to identify. It has been shown for a number of organisms that protective immunity can be induced in this way (e..g *Trypanosoma druzei, Trypanosoma brucei,* Hepatitis B virus, and *Plasmodium knowlesii*).

The antibodies of the present invention may be produced by a method which comprises administering in an immunogenic form at least a part of the polypeptide of the invention to obtain cells producing antibodies reactive with said polypeptide and isolating the antibody containing material from the organism or the cells. The methods of producing antibodies of the invention will be explained further below.

The antibody is preferably a monospecific antibody. The monospecific antibody may be prepared by injecting a suitable animal with a substantially pure preparation of the polypeptide of the invention followed by one or more booster injections at suitable intervals (e.g. one or two weeks to a month) up to four or five months before the first bleeding. The established immunization schedule is continued, and the animals are bled about one week after each booster immunization, and antibody is isolated from the serum in a suitable manner (cf. e.g. Harboe and Ingild, Scand. *J. Immun.* 2 (Suppl. 1), 1973, pp. 161-164.).

For purposes not requiring a high assay specificity, the antibody may be a polyclonal antibody. Polyclonal antibodies may be obtained, e.g. as described in Harboe and Ingild, see above. More specifically, when polyclonal antibodies are to be obtained, the Plasmodium species molecule preparation is, preferably after addition of a suitable adjuvant, such as Freund's incomplete or complete adjuvant, injected into an animal. When the immunogens are human Plasmodium species molecules, the animals may be rabbits. The animals are bled regularly, for instance at weekly intervals, and the blood obtained is separated into an antibody containing serum fraction, and optionally said fraction is subjected to further conventional procedures for antibody purification, and/or procedures involving use of purified Plasmodium species molecules.

In another preferred embodiment, monoclonal antibodies are obtained. The monoclonal antibody may be raised against or directed substantially against an essential component of Plasmodium species molecules, i.e., an epitope. The monoclonal antibody may be produced by conventional techniques (e.g. as described by Köhler and Milstein, Nature 256, 1975, p. 495) e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells or a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium.

The immunized animal used for the preparation of antibodies of the invention is preferably selected from the group consisting of rabbit, monkey, sheep, goat, mouse, rat, pig, horse, and guinea pigs. The cells producing the antibodies of the invention may be spleen cells or lymph cells, e.g. peripheral lymphocytes.

When hybridoma cells are used in the production of antibodies of the invention, these may e grown in vitro or in a body cavity of an animal. The antibody-producing cell is infected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified form ascites by standard purification procedures such as centrifugation, filtration, precipitation, chromatography or a combination thereof.

An example of a suitable manner in which the monoclonal antibody may be produced is as a result of fusing spleen cell from immunized mice (such as Balb/c mice) with myeloma cells using conventional techniques (e.g. as described by R. Dalchau, J. Kirkley, J. W. Fabre, "Monoclonal antibody to a human leukocyte-specific membrane glycoprotein probably homologous to the leukocyte-common (L-C) antigen of the rat", *Eur. J. Immunol.* 10, 1980, pp. 737-744). The fusions obtained are screened by conventional techniques such as binding assays employing Plasmodium species molecules isolated by the above-described methods.

An especially interesting antibody is a monoclonal antibody which is reactive with at least a part of the polypeptide encoded by the nucleic acid molecule of the invention and expressed form the microorganism deposited under the accession No. DSM 4815.

In a further aspect, the invention relates to a diagnostic agent which comprises an antibody as defined above, preferably a monoclonal antibody. Alternatively, the diagnostic agent may be in the form of a test kit comprising in a container a polypeptide comprising a characteristic amino acid sequence of the sequence as shown in FIG. 8 (see Example 6). The diagnostic agent may be used in the diagnosis of plasmodial infection, especially by parasites of the species *P. falciparum*, e.g. in the schizont stage. The diagnostic agent may be used to detect the presence of the plasmodial parasite or of a molecule related thereto in a sample as defined herein.

The diagnostic agent may be one which is suited for use in an agglutination assay in which the solid particles to which the antibody is coupled agglutinate in the presence of a polypeptide of the invention in the sample subjected to testing (see Example 7). In this type of testing, no labelling of the antibody is necessary. For most uses it is, however, preferred that the antibody is provided with a label for the detection of bound antibody or, alternatively (such as in a double antibody assay), a combination of labelled and unlabelled antibody may be employed. The substance used as label may be selected form any substance which is in itself detectable or which may be reacted with another substance to produce a detectable product. Thus, the label may be selected from radioactive isotopes, enzymes, chromophores, fluorescent or chemiluminescent substances, and complexing agents.

Examples of enzymes useful as labels are $\beta$-galactosidase, urease, glucose oxidase, carbonic anhydrase, peroxidiases (e.g. horseradish peroxidase), phosphatases (e.g. alkaline or acid phosphatase), glucose-6-phosphate dehydrogenase and ribonuclease.

Enzymes are not in themselves detectable, but must be combined with a substance to catalyze a reaction the end product of which is detectable. Thus, a substrate may be added to the reaction mixture resulting in a coloured, fluorescent or chemiluminescent product or in a colour change or in a change in the intensity of the colour, fluorescence or chemiluminescence. Examples of substrates which are useful in the present method as substrates for the enzymes mentioned above are $H_2O_2$, p-nitrophenylphosphate, lactose, urea, $\beta$-D-glucose, $CO_2$, RNA, starch, or malate. The substrate may be combined with, e.g. a chromophore which is either a donor or acceptor.

Fluorescent substances which may be used as labels for the detection of the components as sued according to the of invention may be 4-methylumbelliferyl-phosphate, 4-methylumbelliferylD-galactopyranoside, and 3-(p-hydroxyphenyl) propionic acid. These substances may be detected by means of a fluorescence spectrophotometer. Chemiluminescent substances which may be peroxidase/eosin/EDTA, isoluminol/EDTA/$H_2O_2$ and a substrate therefor.

Chromophores may be o-phenylenediamine or similar compounds. These substances may be detected by means of a spectrophotometer. Radioactive isotopes may be any detectable and in a laboratory acceptable isotope, e.g. $^{125}I$, $^{131}I$, $^3H$, $^{35}P$, $^{35}S$ or $^{14}C$. The radioactivity may be measured in a $\gamma$-counter or a scintillation counter or by radioautography followed by densitometry.

Complexing agents may be Protein A, Protein G (which forms a complex with immunoglobulins), biotin (which forms a complex with avidin and streptavidin), and lectin (which forms a complex with carbohydrate determinants, e.g. receptors). In this case, the complex is not in itself directly detectable, necessitating labelling of the substance with which the complexing agent forms a complex. The marking may be performed with any of the labelling substances described above.

In an embodiment of the invention, an antibody or a polypeptide of the invention may be coupled to a bridging molecule coupled to a solid support. The bridging molecule, which is designed to link the solid support and the antibody may be hydrazide, Protein A., glutaraldehyde, carbodiimide, or lysine.

The solid support employed is e.g. a polymer or it may be a matrix coated with a polymer. The matrix may be of any suitable solid material, e.g. glass, paper or plastic. The polymer may be a plastic, cellulose such as specially treated paper, nitrocellulose paper or cyanogenbromide-activated paper. Examples of suitable plastics are latex, a polystyrene, polyvinylchloride, polyurethane, polyacrylamide, polyvinylacetate, and any suitable copolymer thereof. Examples of silicone polymers include siloxane.

The solid support may be in the form of a tray, a plate such as a microtiter plate, e.g. a thin layer or, preferably, strip, film, threads, solid particles such as beads, including Protein A-coated bacteria, or paper.

The polypeptide and antibody of the invention may be used in an assay for the identification and/or quantification of at least a form and/or a part of said polypeptide present in a sample. The identification and/or quantification performed by the use according to the present invention may be any identification and/or quantification involving Plasmodium species molecules or a form of Plasmodium species molecules. Thus, both a qualitative and a quantitative determination of Plasmodium species molecules may be obtained according to the use of the present invention. The identification and/or quantification may be performed for both a scientific, a clinical and an industrial purpose. As will be further described below, it is especially important in clinical routine to identify or quantify Plasmodium species molecules.

The sample may be a specimen obtained form a living organism such as a human or an animal, or an environmental specimen such as water. The specimen may be blood, e.g. an erythrocyte enriched fraction, or a tissue sample e.g. comprising liver cells. In a very interesting embodiment of the present invention, the specimen is urine.

The identification and/or quantification may serve the purpose of diagnosing an infection with a Plasmodium species in an organism, e.g. an animal or a human being. The diagnosis is preferably performed on a specimen or sample from the organism, e.g. a specimen or sample of the type mentioned above. The identification and/or quantification may be performed by use of an assay in which the polypeptide or the antibody of the invention is employed. The polypeptide or antibody may be part of an assay kit of a composition suitable for its intended used. Such assay kits may comprise one or several layers and contain Plasmodium species molecules prepared by any of the methods described herein. This will be explained in further details below.

A drawback of some of the known methods for diagnosing malaria using clinical samples has been that known tests, when performed on samples of body fluids, principally whole blood, have not shown the specificity and sensitivity required for accurate diagnosis, and the one specific test, namely detection of the parasites in smears of peripheral blood obtained form an infected individual, requires specially trained personnel, i.e. it cannot be performed as a routine analysis. Also, it is unsuited as a screening analysis for the screening of a large number of patients.

The identification and/or quantification of Plasmodium species molecules in accordance with the present invention may be advantageous in accurate detection of e.g. recently acquired infection with Plasmodium species as readily available samples, in particular whole blood, plasma, serum or urine, may be used.

The malaria infection may be diagnosed by examining a sample, e.g. a blood or urine sample, for the presence of antibodies against Plasmodium species molecules, the presence of Plasmodium species molecules, and/or the presence of a DNA or RNA fragment encoding the Plasmodium species molecules. Also, the presence and amount of Plasmodium species molecules in a vaccine, e.g. of the type disclosed herein, may be determined in this manner. As mentioned above, one aspect of the invention which is contemplated to be novel and very interesting is the diagnosis of malaria infection performed on an urine sample. The use of an urine sample in the diagnosis of malaria is an easy and convenient approach for the diagnosis as compared to the use of a blood or serum sample.

In one preferred embodiment of the invention it is preferred that the antibody used in the method of the invention is a monoclonal antibody as this generally provides a higher precision and accuracy of the assay, at the same time possible requiring less time to perform. Furthermore, a mixture of two or more different monoclonal antibodies may be employed as this may increase the detection limit and sensitivity of the test. The monoclonal antibody may be obtained by the method described below. Antibodies possessing high avidity may be selected for catching techniques.

The antibody used in the present method is preferably in substantially pure form (purified according to suitable techniques or by the methods of the invention, see below) in order to improve the precision and/or accuracy of the assays of the invention.

When the polypeptide or antibody of the invention is to be used for identification and/or quantification of Plasmodium species molecules it may be advantageous that the polypeptide or antibody is provided with a detectable marker or label. The detectable maker may be any marker which may easily be identified by means of conventional techniques and equipment, such as a radioactively labelled marker. e.g. an isotope such as $^{125}I$ (G. Doring, H. J. Obernesser & K. Botzenhart, "Extracellular toxins of *Pseudomonas aeruginosa*, Radioimmunoassay for detection of alkaline protease", *Zentralbl. Bakteriol. Parasitenkd. Infektionskr. Hyg. Abt.* 1 Orig. 252, 1982, pp. 231–147), or an enzyme-labelled marker (D. J. Fitzgeralt, T. A. Waltmann, M. C. Wilingham & I. Pastan, "Pseudomonas exotoxin-Anti-TaC cell-specific immunotoxin active against cells expressing the human T cell growth factor receptor", *J. Clin. Invest.* 74, 1984, pp. 966–971) or a marker labelled with fluorescein (J. A. Hoxic, J. D. Alpers, J. L. Rackowski, K. Huebner, B. S. Haggarty, A. J. Cedarbaum & J. C. Redd, "Alterations in T4 (Plasmodium species) protein and mRNA synthesis in cells infected with HIV", *Science* 234, pp. 1123–1127). Also a complexing agent such as biotin may be a useful marker.

The determination of antibodies reactive with the polypeptide of the invention and being present in a sample, e.g. as defined above, may be carried out by use of a method comprising contacting the sample with the polypeptide of the invention and detecting the presence of bound antibody resulting from said contacting and correlating the result with a reference value.

In one embodiment, the method of the invention employs some of the well known ELISA principles, e.g. direct (see Example 4), catching (see Example 5), competitive (see Example 6) and double enzyme linked immunosorbent. In e.g. an inhibition assay a purified polypeptide preparation of the invention is attached to a slid support (e.g. a polystyrene microtiter tray (Nunc); the test solution to be measured is mixed with specific reference antibodies, e.g. the antibodies of the present invention, and this mixture is incubated with the solid support provided with the polypeptide preparation as mentioned above. After sufficient washing, enzyme-labelled anti-IgG-antibodies are added, and finally enzyme substrate is applied, see Example 6. For further detailed information of the principles employed in ELISA techniques, cf. for instance Voller, A., Bidwell, D. E. and Bartlett, A. (1979): The Enzyme Linked Immunosorbent Assay (ELISA) Dynatech Europe, Borough House Guernsey.

The ELISA and RIA methods are well established and may be carried out with existing laboratory equipment and may also be subjected to automation. The methods of the inventions therefore has wide applicability in clinical laboratories for diagnostic purposes and for monitoring the results of vaccination procedures, and in the pharmaceutical industry as an assay for immunogens to be sued in the production of vaccines.

The presence of Plasmodium species molecules or Plasmodium species molecules-like material may be determined both negatively and positively. The method of the invention may be used for both qualitative (see Example 7) and quantitative determination of Plasmodium species molecules (see Examples 5 and 6). For quantitative measurement, the amount of antibody bound in the test may be determined by series dilutions of the samples in a manner well known in the art.

When the polypeptide of the invention is to be employed in an assay for determining the presence of Plasmodium species molecules in a sample, it may be in the form of a diagnostic reagent or a diagnostic agent. As will be apparent to a person skilled in the art several techniques may be applied in connection with such diagnostic reagents.

When, according to the invention, any part of said polypeptide is coupled to a solid support, an antibody against the component may then be added (see Examples 4 and 6). Alternatively, the antibody is coupled to a solid support (see Examples 5 and 6).

As a further alternative, any Plasmodium species molecules present in the sample is coupled to a solid support. It may then be incubated with the polypeptide component by addition of the component to the solid support followed by adding an antibody labelled with a detectable marker.

As stated above, infection by Plasmodium species molecules in an organism or the presence of such in a sample may be detected by determining the presence of a DNA sequence related to the Plasmodium species molecules using a DNA sequence of the invention. The detection is based on homology between DNA sequences in the sample and the DNA sequence of the invention and may be performed by use of a diagnostic agent comprising a labelled DNA sequence homologous with a DNA sequence encoding at least part of the polypeptide of the invention. The DNA sequence may be labelled with any suitable label, e.g. selected from radioactive isotopes, enzymes, chemical modifying agents such as sulphonyl-introducing compounds and complexing agents such as biotin.

The use of a nucleic acid molecule for the detection of the presence of DNA sequences related to Plasmodium species molecules in a sample may advantageously be carried out utilizing the principles of the polymerase chain reaction as described by Randall et al., Science 1985, 230: 1340-1354, Randall et al., Science, 1988, 239:487-491, and Stoflet et al., Science, 1988, 239:491-494. The polymerase chain reaction (PCR) is a procedure used for the amplification of DNA present n a sample (see Examples 7 and 9). The procedure involves the use of two oligonucleotide primers which flank the nucleic acid molecule to be amplified. The oligonucleotide primers may e.g. by 10- to 45-mers or more and comprise the flanking regions of glurp or be part of glurp. The oligonucleotide primers are constructed so as to enable hybridization of one primer to the plus strand 5' of the target DNA, and of another primer to the minus strand 5' of the target DNA. The preferred distance between the two primers is 100-2000 basepairs or more for diagnostic purposes, whereas longer distances could be accepted for preparative purposes. The primers are hybridized with the opposite DNA strands to be amplified and are extended by using DNA polymerase, e.g. the Klenow fragment of E. coli DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, from the "parent DNA strings", and the parent strings as well as the newly synthesized DNA strings are subjected to a new PCR amplification cycle. In this manner, it is possible to obtain a substantial amplification of specific DNA sequences which are present in a sample. By use of the PCR amplification method, it may be possible to amplify and thus detect the presence of originally very small and undetectable amounts of DNA sequences present in a sample, and thereby e.g. identifying a malaria infection.

The invention is further illustrated in the following with reference to the drawings and the examples.

Pr is the rightward promoter of the λ-phage, the arrow indicates the direction of transcription of this promoter.

Cro' is the 5'-part of the λ-phage cro-gene, lacZ' is the 5'-part of lacZ-gene encoding the N-terminal part of the β-galactosidase enzyme, Ori is the MB1-origin of replication, the arrow indicates the direction of replication, bla is the gene encoding the enzyme β-lactamase conferring ampicillin resistance to the host organism.

The wavy line symbolizes the Cro'-gene and the lacZ'-gene, the double line (=) symbolizes the malaria-derived DNA fragment encoding GLURP. The plasmid pRD15 encodes a fusion protein consisting of the N-terminal part of the Cro-protein, the N-terminal part of the β-galactosidase enzyme and GLURP. The size of the plasmid pRD15 is 8857 basepairs.

Figure 3:
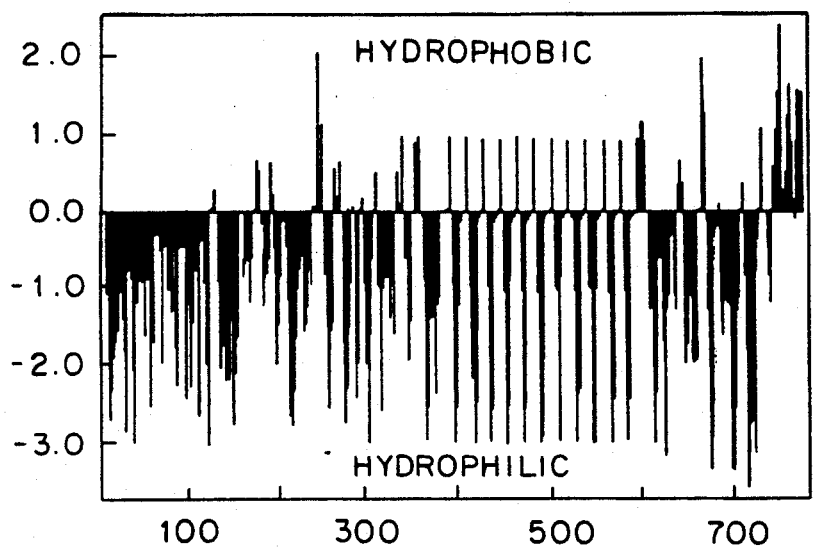

FIG. 3 illustrates the hydropathy of the GLURP protein as determined by use of the indexes of Kyte and Doolittle.

Figure 4:
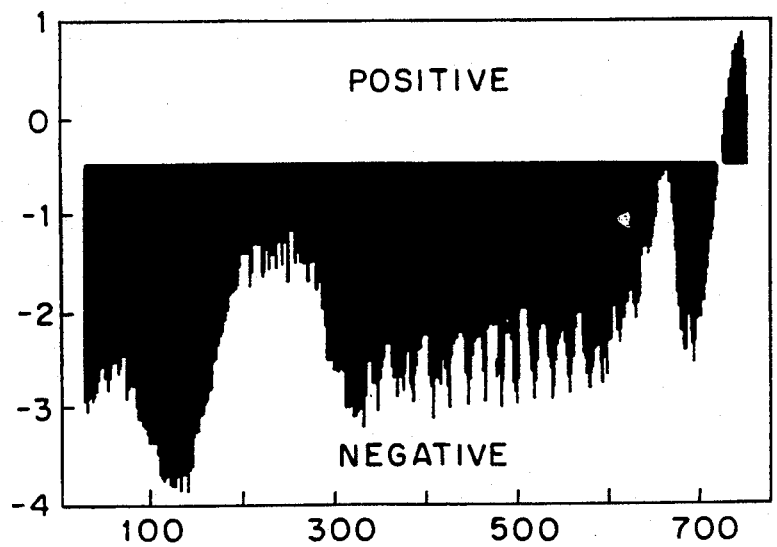

FIG. 4 shows net charge of the GLURP protein, estimated for segments of 50 amino acids.

Figure 5:
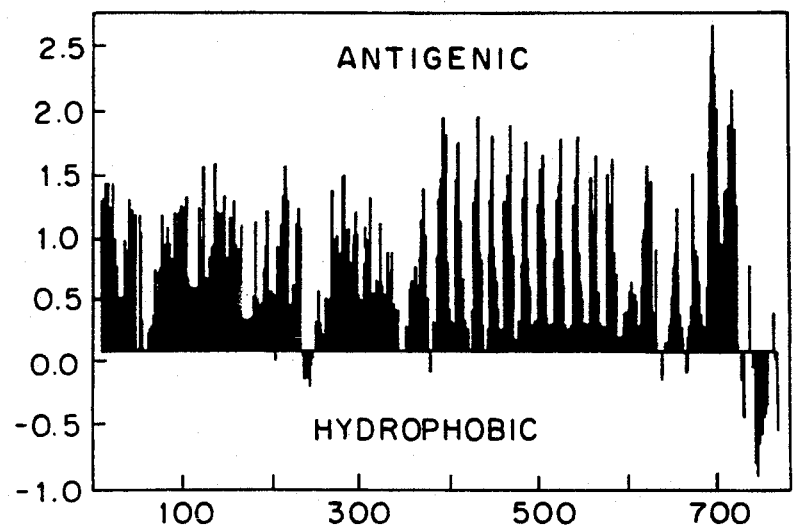

FIG. 5 shows the antigenicity according to Hopp and Woods of the GLURP protein.

FIG. 6 shows a dot diagram representing the optical densities measured by the antibody detecting ELISA for serum samples diluted 1:200 from malaria-immune patients as well as patients having diagnosed toxoplasmosis and schizostomiasis and serum from a control group, as described in Example 3.

FIG. 7 illustrates the nucleotide sequence of the DNA sequence glurp encoding GLURP. The nucleotide sequence has been determined as described in Example 1. The arrow indicates the stopcodon.

FIG. 8 illustrated the amino acid sequence deduced from the nucleotide sequence encoding the GLURP protein.

Figure 9:
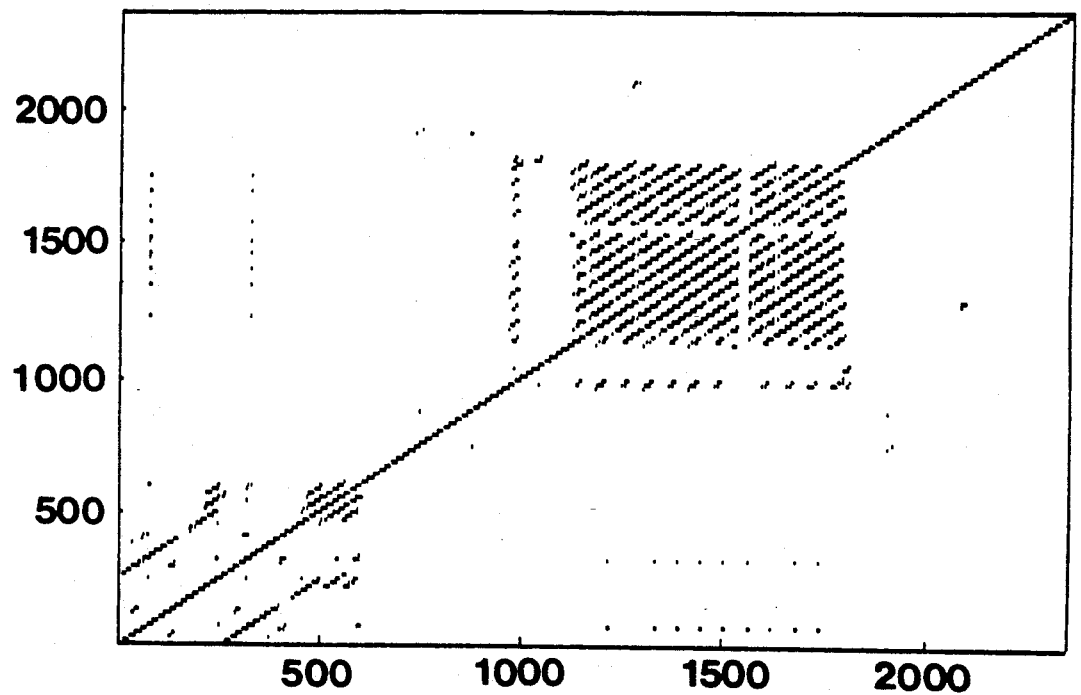

FIG. 9 shows a homology matrix with the sequence of the gene encoding GLURP represented along the X- and Y-axis. A block of the first 30 bases from the X-axis is compared to the first 30 bases on the Y-axis and a dot printed at positions where at least 24 of the bases are identical (80% homology). The block is then moved one base on the Y-axis to bases 1-31 and the comparison repeated and so forth to the end of the sequence. The procedure is repeated with bases 2-32 from the X-axis and so on until the whole sequence has been compared.

Figure 10:
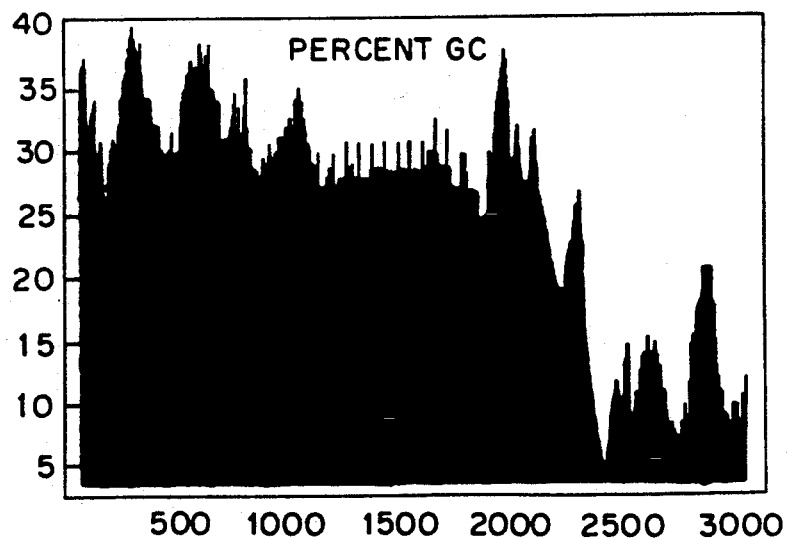

FIG. 10 illustrates the CG content of the DNA sequence of glurp.

Figure 11:
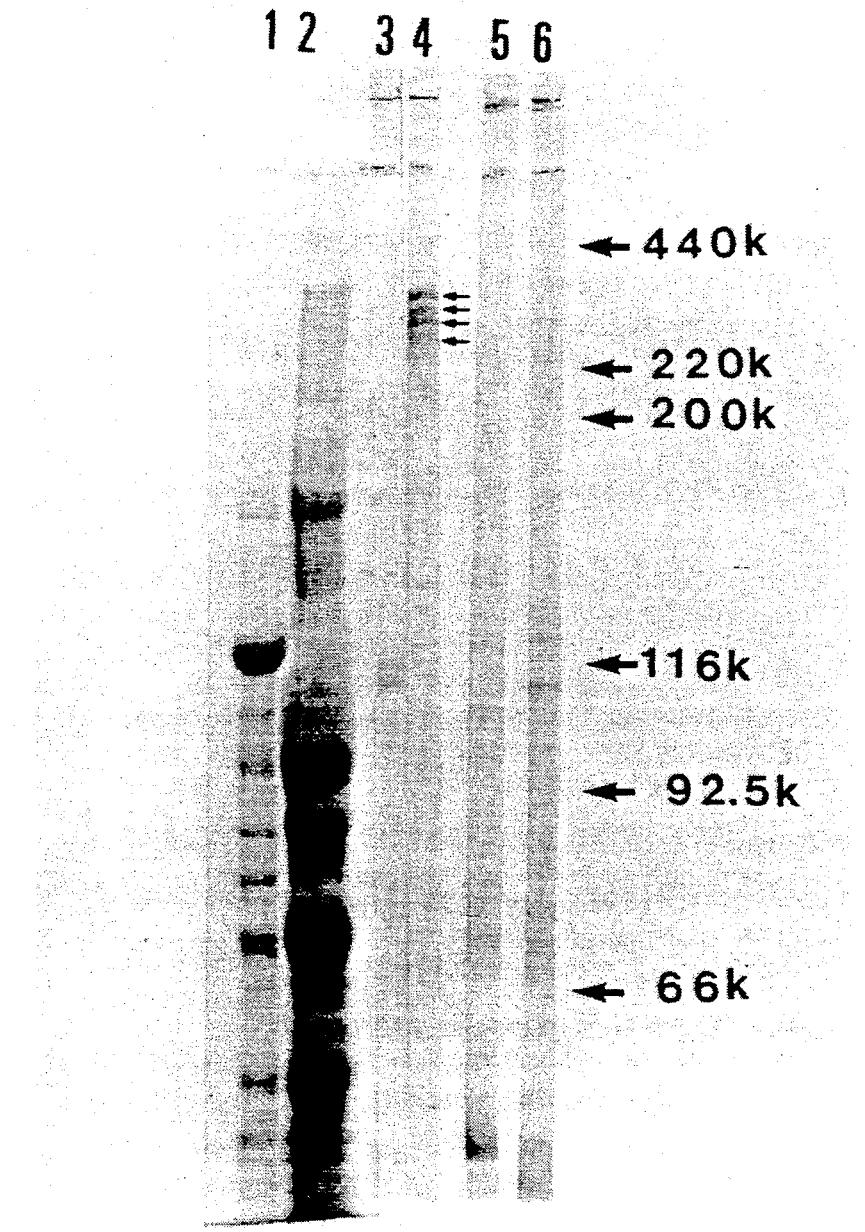

FIG. 11 shows the lysates of the λ-gt11 lysogen (lane 1) and the Φ15 lysogen (lane 2), separated on a 7.5% SDS-PAGE. The proteins were visualized by staining with Coomassie brilliant blue and the same proteins were blotted to nitrocellulose membranes (lanes 3 and %: λgt11 lysogen and lanes 4 and 6: Φ15 lysogen). Lanes 3 and 4 show the reaction of the antibodies affinity purified with antigen 1 as the ligand and lanes 5 and 6 show the reaction of a pool of sera from Danish donors. Molecular weight markers used were ferritin (not reduced, not boiled), 440k, 220k; myosin 200k, β-galactosidase 116k; phosphorylase B 92.5k; bovine serum albumin 66k. (All k indicate kD).

Figure 12:
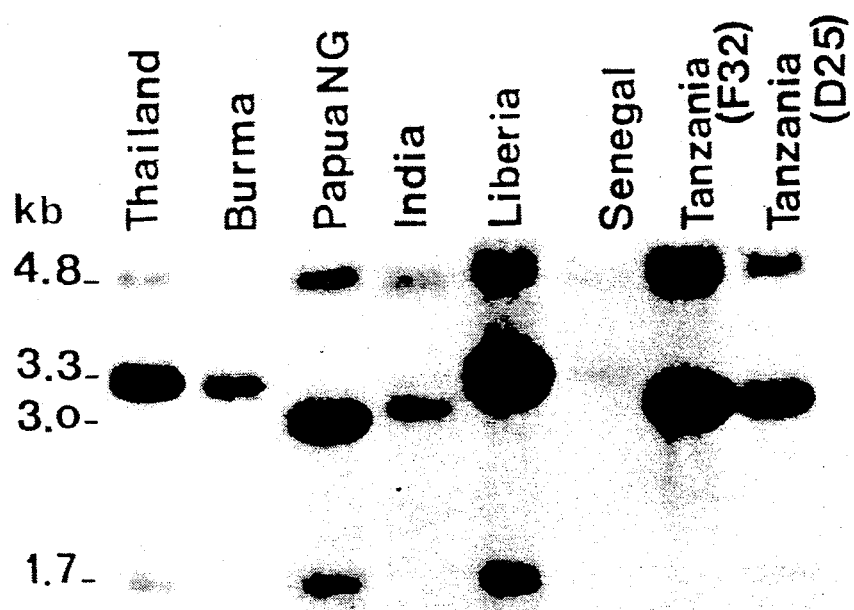
Figure 13A:
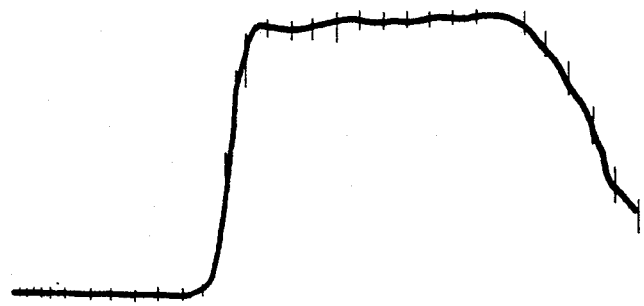
Figure 13B:
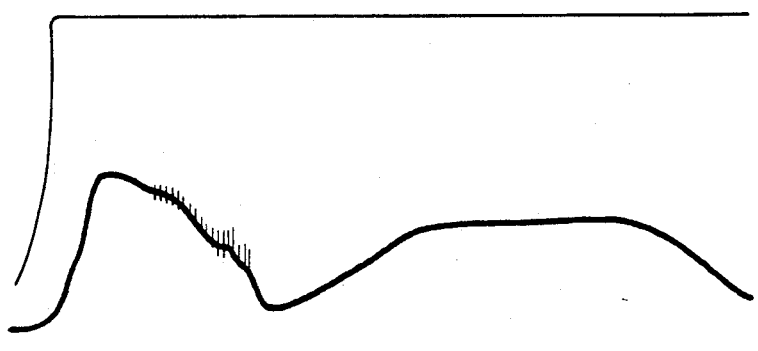
Figure 13C:
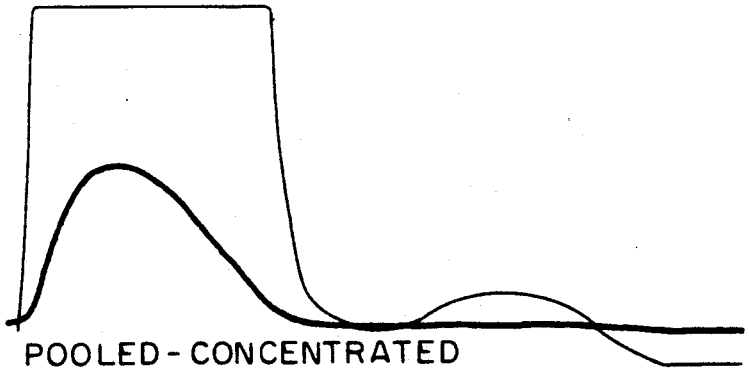
Figure 13D:
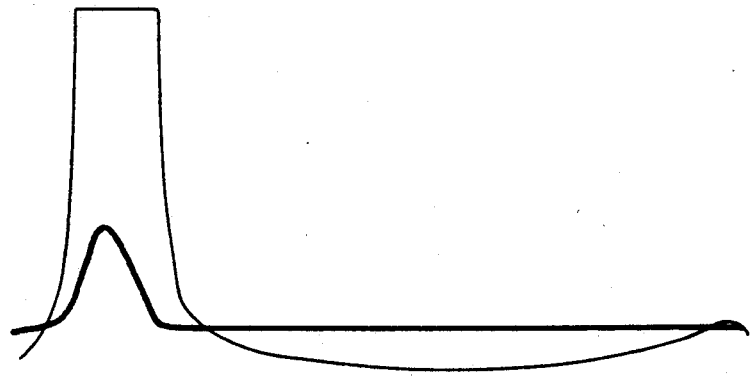

FIG. 12 shows a Southern Blot of geographically different isolates of P. falciparum digested with BclI as explained in Example 1. λ-DNA digested with HindIII was used as molecular size markers. Genomic DNA was digested with BclI, fragments separated by electrophoresis on a 1% agarose gel and blotted to nitrocellulose (Schleicher and Schuell) and probed with a nick-translated (nick-translation kit, Amersham) Φ15-insert, labelled with the α-32p-dATP. The last washing was performed at 0.1×SSC (Maniatis p. 447), 65° C., 10 minutes.

FIG. 13 A, B, C and D illustrate chromatograms obtained by continuous UV-monitoring of the eluate during gel filtration on a Sephacryl S400 High Resolution column (dimensions 900×26 mm).

A) Chromatogram resulting from a separation where the fraction soluble in guanidinium hydrochloride of an unprocessed lysate was applied to the column. This gives a broad plateau, representing a bad separation of the fusion protein eluted immediately after void volume.

B) Chromatogram resulting from a separation where the material applied to the column had been processed as inclusion bodies. The material eluted corresponding to the line on the figure was pooled and concentrated as explained in Example 2. Impurities in the fusion protein preparation were seen as irregularities in the first peak and in the existence of a second peak.

C) Chromatogram resulting from a separation where the pooled and concentrated material mentioned above was run for an additional column length. The curve was further smoothed but still a minor second peak was detected on the more sensitive second channel. The material eluted corresponding to the line on the figure was pooled and concentrated as explained in Example 2.

D) Chromatogram resulting from a separation where the pooled and concentrated material mentioned above was run for an additional column length. No peaks other than the one representing the fusion protein was observed. Material from this peak is shown in FIG. 14, lanes 6, 7, and 8.

Figure 14:
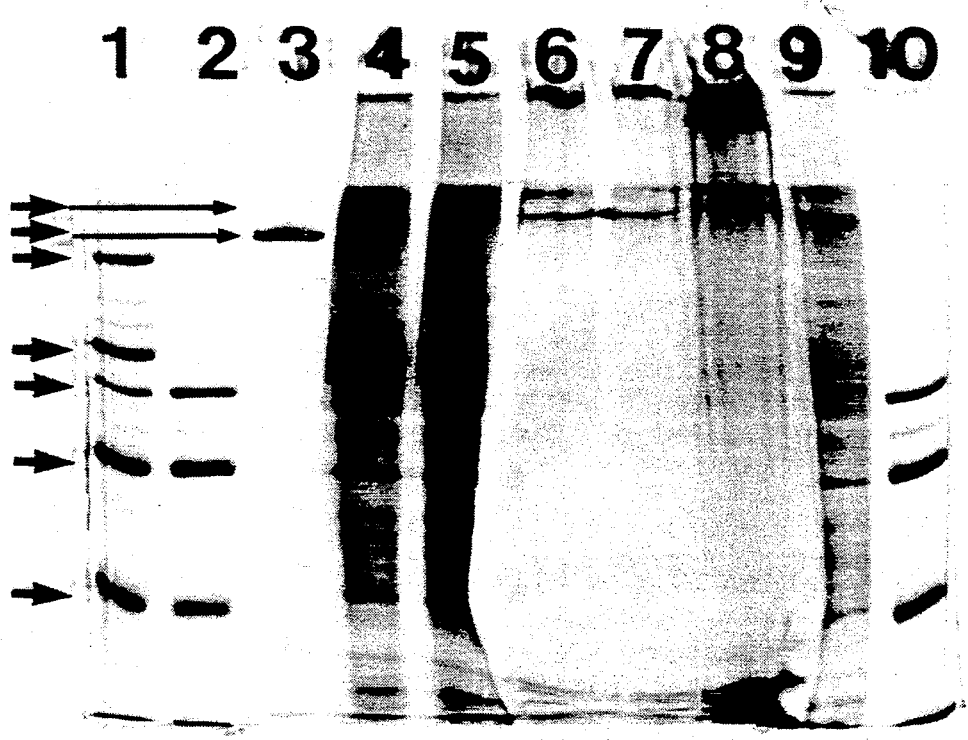

FIG. 14 illustrates a 7.5% SDS-PAGE run under reducing conditions:

Lanes 1, 2 and 10; BioRad High and Low molecular weight markers.

Lane 3: Pharmacia Ferritin molecular weight marker. Molecular weights in kD corresponding to the arrows (from top to bottom): 440, 220, 200, 116, 92, 66, 45.

Lane 4, 5, and 9: Partially purified inclusion bodies from pRD15 (20, 30, and 10 μl, respectively). An extreme load of proteins was observed in the range from the top of the separationgel to the 45 kD marker.

Lane 6, 7, and 8: Inclusion bodies after 2700 mm gel filtration over a S400HR-column, volume applied to gel 10, 5 and 20 μl, respectively. The effect of the gel filtration chromatography was obvious. One band of relative molecular weight 300 kD was seen. The application of 20 μl of fusion protein in lane 8 resulted in overloading and the production of a smear. This figure combined with FIG. 13B, C, and D demonstrates the substantial purity of the protein.

Figure 15:
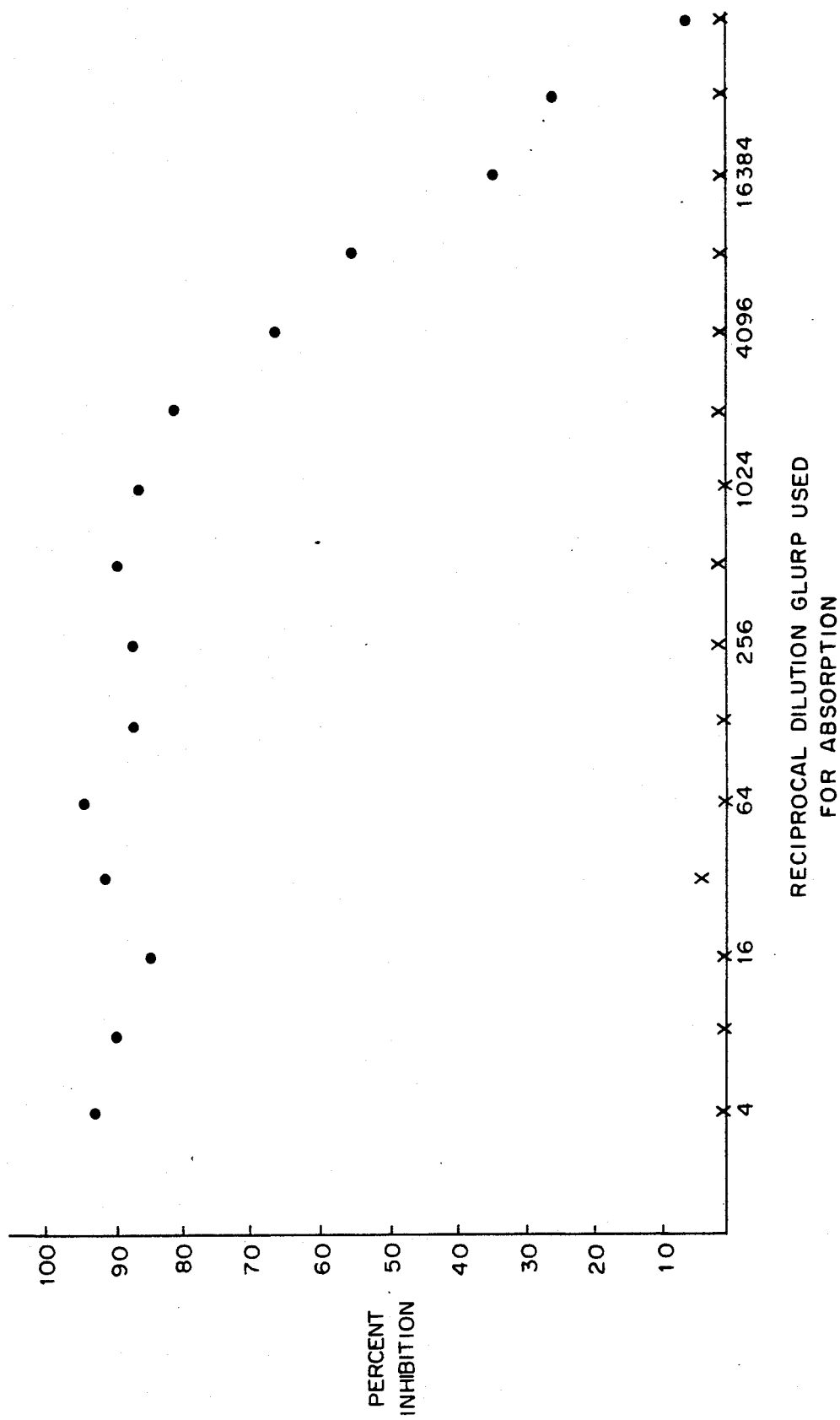

FIG. 15 is a semilogarithmic plot of inhibition of the reactivity of human immune serum with native GLURP as a function of the dilution of GLURP used for absorption ('), GLURP could inhibit 92% of the reactivity which indicates that the recombinant protein is almost identical to eh native protein. As a control, similar amount of β-galactosidase were sued instead of GLURP for the similar procedures (x). No inhibition was observed. Dilutions were made from a 1 mg GLURP/ml solution in PBS.

FIG. 16 is a semi-logarithmic plot showing the GLURP detecting ELISA employed on supernatant from in vitro P. falciparum culture (hematocrite 6%) with different parasitemias determined by microscopy. The dilution of the specimens was 1:100, capturing antibody was purified rabbit-anti-fusion protein antibodies diluted 1:320 from a 4 mg/ml stock. Detecting antibody was mouse-anti-fusion protein antibodies diluted 1:500 from serum. The conjugated rabbit-anti-mouse immunoglobulin (DAKOPATTS P260) was diluted 1:1000.

Figures 17A, 17B:
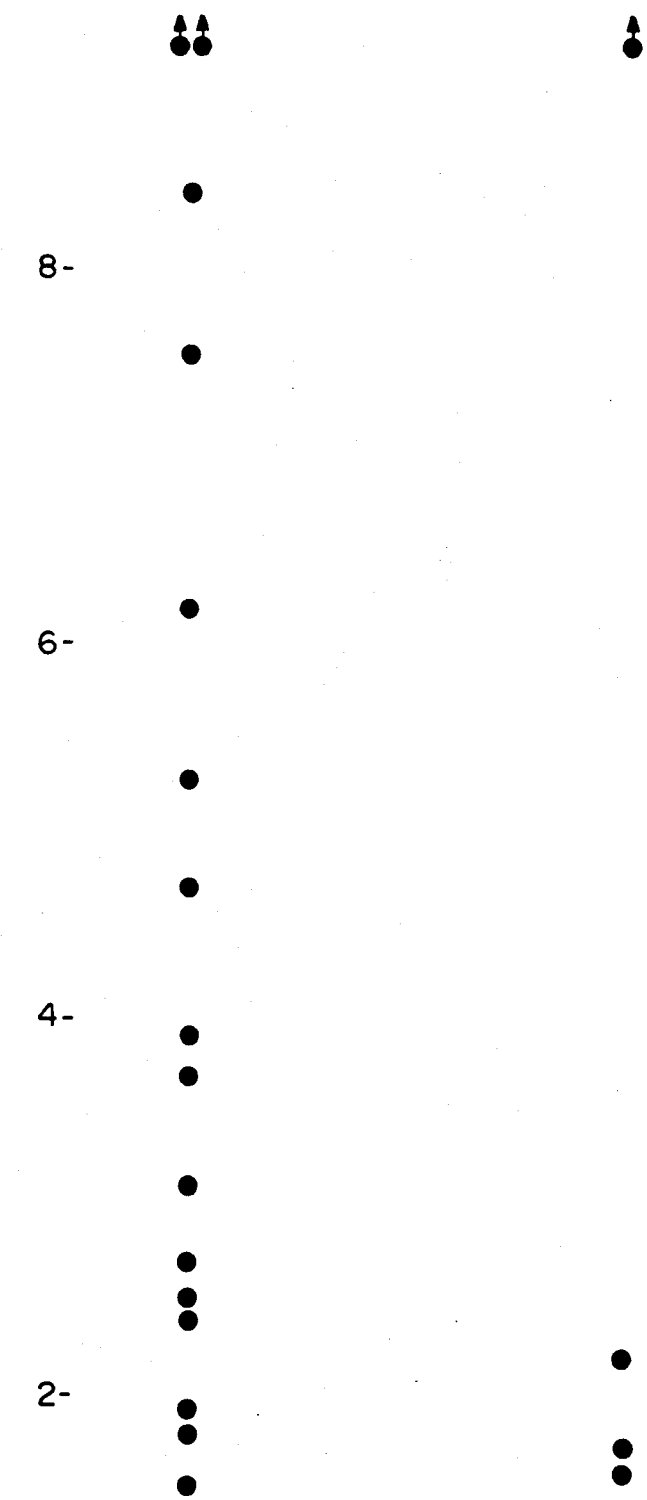

FIG. 17 Epitope mapping. Patly purified protein, containing the major repeat area of GLURP was tested for T-cell epitopes. The figure shows the proliferative response of T-cells from (A) 16 malaria-immune donors from the Gambia, and (B) 8 non-immune European donors. T-cells from 13 out of 16 malaria-immune donors responded with a proliferative index above 2.5, while only one of the non-immune donors, a malaria convalescent, responded significantly. The stimulation index was calculated by dividing the geometric means of a triplicate of measurements with the geometric mean of three control measurements.

FIG. 18 is a semi-logarithmic plot showing the results obtained in an antibody detected ELISA analysis of antibodies present in the sera of rabbits which had been immunized with the fusion protein as described in Example 12A.

Figure 19:
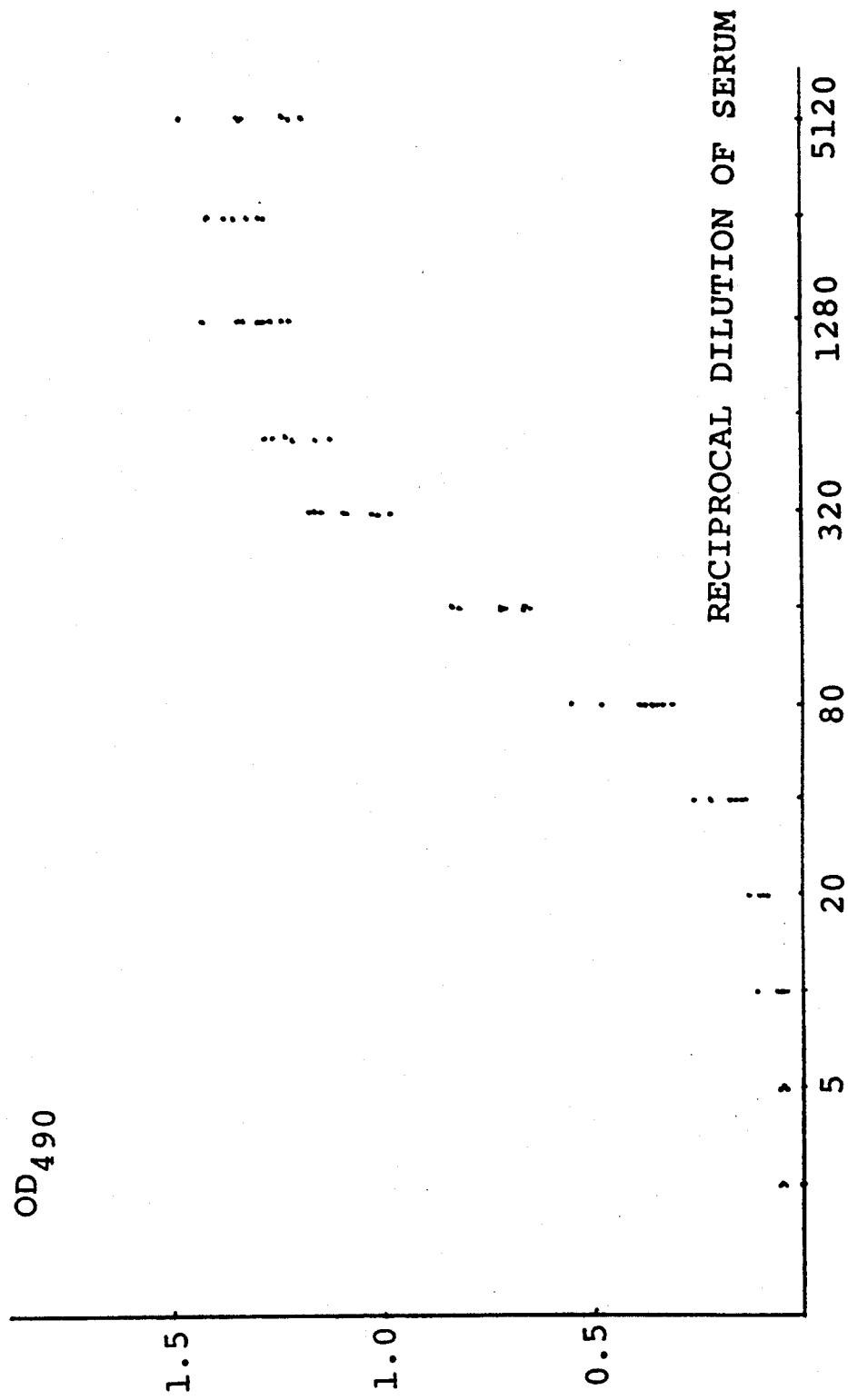
Figure 20A:
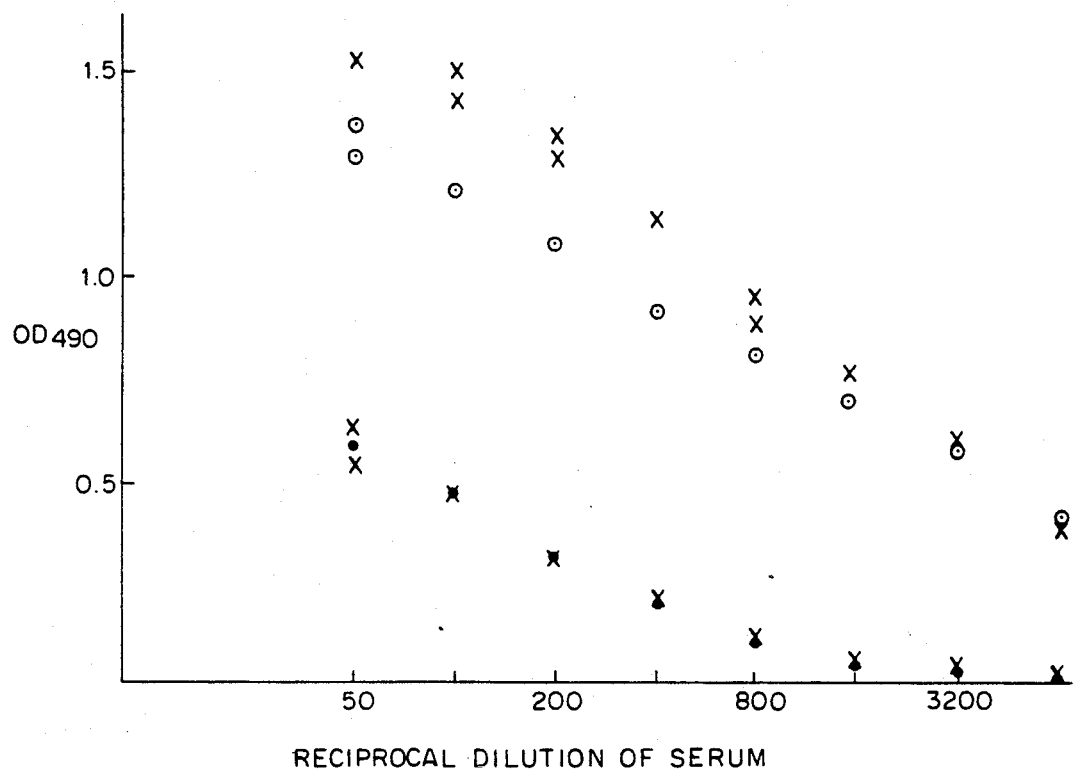
Figure 20B:
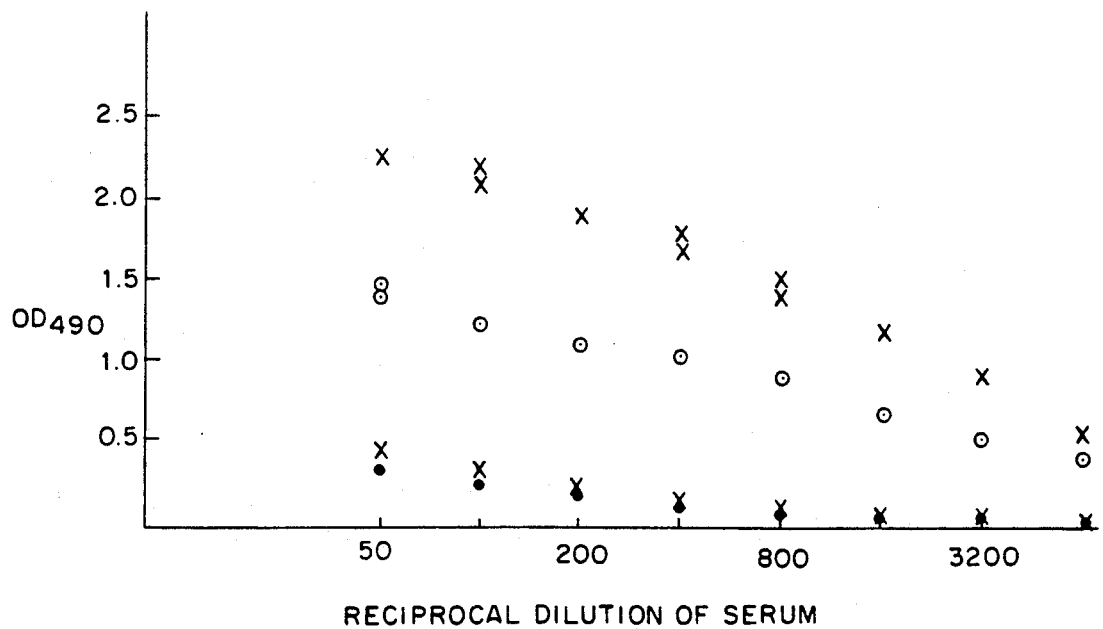
Figure 20C:
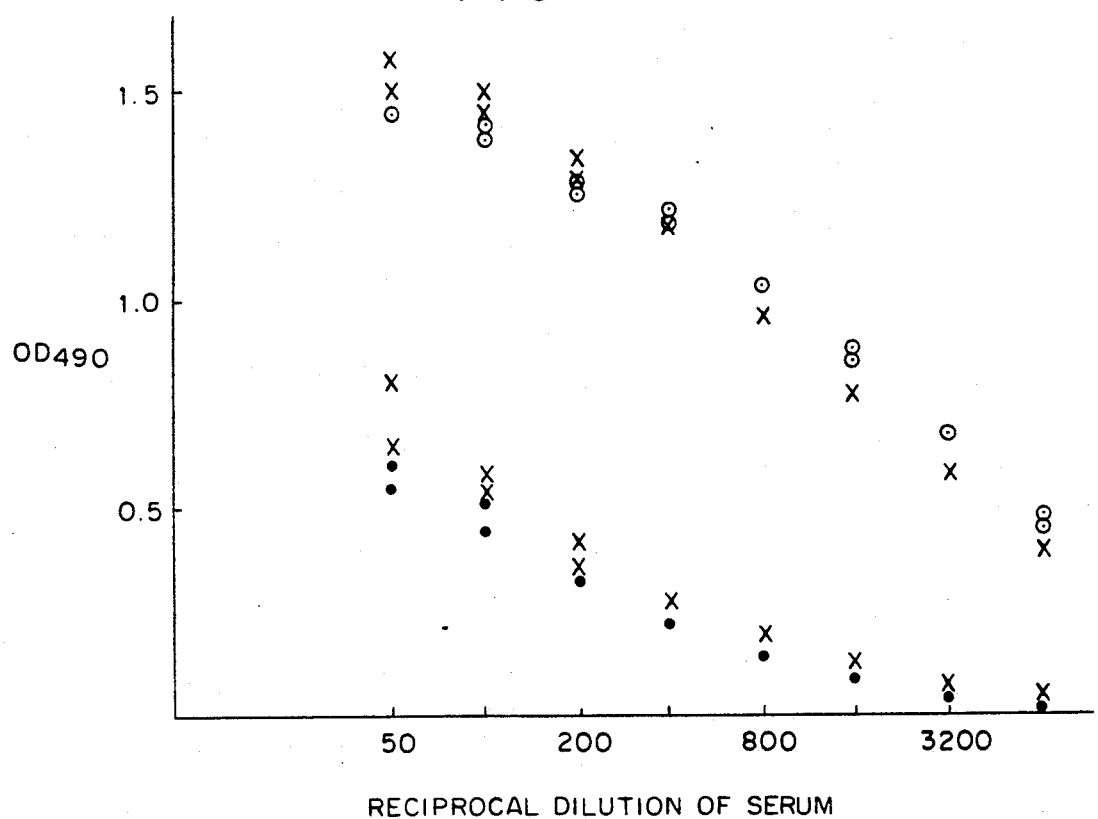
Figure 20D:
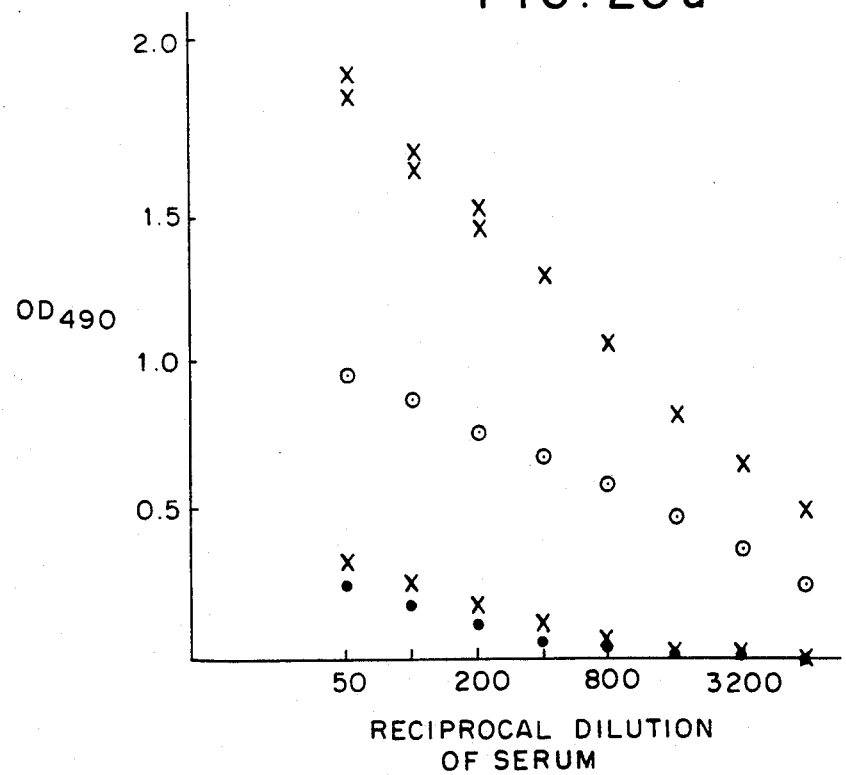

FIG. 19 is a semi-logarithmic plot showing a competition assay: Rabbit anti-fusion protein antibodies competed with human malaria-immune serum for the fusion protein coating. The rabbit antibodies were able to extinct the reactivity of the human antibodies as described in Example 12A.

FIG. 20 A, B, C, and D. Titrations of monkey serum obtained from the four monkeys immunized with the fusion protein. The sera were collected on day −132 (.), day 0 (x), day 14 (o), and day 28 (X), with respect to the day of immunization. Analyses were performed with the antibody detecting ELISA described in Example 3 coated with 0.125 μg of fusion protein/well. The binding of monkey anti-fusion protein antibodies was detected by rabbit-anti-monkey serum antibodies diluted 1:1000, the binding of rabbit antibodies was subsequently detected by porcine anti-rabbit antibodies diluted 1:1000.

A represents the titration curves for monkey number 864.

B represents the titration curves for monkey number 865.

C represents the titration curves for monkey number 866.

D represents the titration curves for monkey number 867.

All monkeys developed significant titers against the fusion protein, irrespective of adjuvant(s) sued.

MATERIALS AND METHODS

The malaria isolate used for constructing the genomic library was the Tanzanian isolate, F32. The isolated used for the Southern Blotting were from Tanzania (F32, D25), Burma (D51), Senegal (D28), India (D41), Liberia (L1), Kenya or Tanzania (D50), and Kenya (K1), All the isolates were from patients who had travelled in the country indicated as the origin. Isolate D50 are from a patient who had travelled in Kenya and in Tanzania. All malaria isolates are available at Statens Seruminstitut, Copenhagen, Denmark.

Human sera used for the screening of the genomic library and for the characterization of proteins were from Africa and Indonesia. Antibodies predominantly recognizing antigen 1 were purified from African malaria-immune sera using a chromatographic affinity purification with antigen 1 as the ligand. The following vectors were used: M13, pUC9, λgt11, pEX2. The following E. coli cell lines (deposited in the American Type Culture Collection under the accessions numbers indicated below) were used: Y 1090 (ATCC No. 37197), Y 1089 (ATCC No. 37196), Y 1088 (ATCC No. 37195), and POP 2136 (From Gensplejsningsgruppen, Lyngby, Denmark).

ELISA for the Detection of β-galactosidase

Antibodies:

Rabbit anti-mouse IgG conjugated to horseradish peroxidase obtained from Dakopatts, code P260; anti-human IgG conjugated to horseradish peroxidase, DAKOPATTS, code P214. Mouse monoclonal anti-β-galactosidase, (Mgal 8), obtained from the Hybridoma Laboratory, Statens Seruminstitut, Denmark.

Chemicals:

Hydrogen peroxide 30%, hydrogen peroxide, article No. 7210 Merck. 1.2 ortho-phenylenediamine-dihydrochloride (OPD) obtained from KemEnTec, Copenhagen, Denmark.

ELISA equipment:

Mitrotiter ELISA plates, no 4-39454 obtained form NUNC, ELISA reader (Immunoreader, NJ2000, TECHNUNC). Immunowasher 12 obtained from NUNC.

Buffers:

Carbonate buffer pH 9.6 (1.59 g $Na_2CO_3$, 2.93 g $NaHCO_3$ to 1000 ml with distilled water).

Washing buffer (29.2 g NaCl, 0.2 g KCl, 0.2 g $KH_2PO_4$, 1.15 g $Na_2HPO_4.2\ H_2O$, 10 ml Triton-X-100 to 1000 ml with distilled water).

Dilution buffer pH 7.2 (10 g Bovine albumin, 2 ml phenol red 0.5%, to 1000 ml with washing buffer, pH adjusted to 7.2 with sodium hydroxide).

Conservation buffer (29.2 g NaCl, 0.2 g KCl, 0.2 g $KH_2PO_4$, 1.15 g $Na_2HPO_4.2\ H_2O$, 1.7 g sodium azide, 5 g Bovine albumin, to 1000 ml with distilled water).

Colouring buffer pH 5.0 (7.3 g citric acid.$H_2O$, 11.896 g $Na_2HPO_4.2\ H_2O$, to 1000 ml with distilled water).

Colouring substrate solution (40 mg OPD was dissolved in 100 ml colouring buffer supplemented with 40 μl of hydrogen peroxide). The container for this solution was wrapped in tin foil to avoid exposure to light. The solution could be used for 1 to 2 days stored at 4° C,.

Equipment Used for Immunosorbent Techniques

Pump: Varioperpex 1, LKB, Stockholm Sweden.

Recorder: LKB, Stockholm, Sweden, model 2210.

UV-monitor: Pharmacia Fine Chemicals, Uppsala, Sweden, model UV-1, 280 nm.

Concentration cell: Amicon cell, model 202, ultrafilter PM 10 (Amicon Corp., Lexington, Mass., USA).

Filter: 0.22 μm from Schleicher und Schuell.

Fraction collector: Redirac, LKB, Stockholm, Sweden.

Production of Antibodies against Native Antigen 1

IgG was isolated from EDTA-plasma of a known malaria-immune African adult by salting out and ion exchange as described in details in the literature, e.g. Harboe, N. and Ingild, A.: Immunization, isolation of immunoglobulins and estimation of antibody titer, Scand. J. Immunol. 2, suppl. 1:161,1973. By crossed immunoelectrophoresis (CIE), the plasma was shown to contain antibodies against antigen 1 and Antigen 2 as described in (1). The crossed immunoelectrophoresis was carried out essentially as described by Jepsen, S. and Axelsen, N. H. in (1), 140 mg of the IgG antibodies was coupled to 15 g CNBr activated Sepharose 4B from Pharmacia Fine Chemicals. The procedures of the manufacturer were followed. Antigen from the supernatant of malaria culture (P. falciparum, F32) was purified as described by Jepsen, S. and Andersen, B. J. in (2).

A pool of antigen purified on the immune IgG column was coupled to CNBr activated Sepharose 4B according to the manufacturers instructions. It was observed fortuitously by analyzing the passage of this coupling by crossed immunoelectrophoresis as described above that it contained antigen 1 exclusively, being due, either to an excessive amount of antigen applied to the used mass of CNBr Sepharose, and/or being due to a lower efficient of the coupling of antigen 1 than of the other antigens in the pool to CNBr activated sepharose. The run-through was concentrated and coupled to 2.3 g (dry weight) of CNBr Sepharose 4B following the procedure of the manufacturer. Using the procedures and reagents mentioned under the heading: Use of Fusion protein for Affinity Purification of Human Antibodies Directed against GLURP, antibodies with specificity against GLURP was purified. The specificity of the antibodies was tested in the intermediate gel of a CIE.

Sodium Dodecyl Sulphate Polyacrylamide Gel Electrophoresis (SDS-PAGE)

Analysis of proteins by sodium sulphate polyacrylamide gel electrophoresis (SDS-PAGE) was performed with the BioRad Protean 2 or Mini-Protean 2 system using a discontinuous gel system with a 3% stacking gel and a 7.5% separating gel. All reagents for gel electrophoresis were obtained from BioRad. Typically, a volume of 50 µl of each sample to analyse was mixed with ¼ volume loading buffer (4% Sodium dodecyl sulfate (SDS), 0.4M dithotreitol, 0.08M Tris-HCl pH 7.8, 10% glycerol), boiled for 5 minutes, and separated by electrophoresis in the above mentioned gel system (reference: Laemmli U. K. Nature, 227:680–685;1970). The proteins were visualized with Coomassie brilliant blue.

Western Blot Analysis

For Western Blot analysis, the proteins were initially separated on SDS-PAGE as described above and then transferred electrophorectically from the gel to a 0.22 µm nitrocellulose filter (Schleicher und Schuell). Blotting was done at a field strength of 6 V/cm for 5 hours at 4° C. with the gel and membrane submerged in transfer buffer. After blotting, the nitrocellulose filter was blocked with a washing buffer containing 0.5% Tween-20 solution and Blots were incubated for one hours with sera or purified antibody against antigen 1 diluted appropriately in washing buffer. After extensive washing (3 incubations of 15 minutes with washing buffer on a rocking table), visualization was performed using porcine anti-human-IgG conjugated to horseradish peroxidase (obtained from DAKOPATTS P214) in dilution 1:1000 followed by washing as above and a peroxidase staining according to Heegaard, N. H. H. et al., Immunoblotting. General principles and procedures, Handbook of immunoblotting of proteins, CRC Press, Boca Raton, Fla., 1987.

Crossed Immunoelectrophoresis (CIE)

CIE was performed on glass plates 7×5 cm in 1% agarose gel (Litex, Glostrup, Denmark, type HSA) in Tris-barbitol buffer pH 8.6 ionic strength 0.02 by running 20 µl of the affinity purified soluble antigens in the first dimension gel at 10–15 Volt/cm until a parallel blue albumin marker had migrated 2,6 cm. The second dimension electrophoresis was run perpendicular to the first dimension el at 2 Volt/cm for 18 hours into a gel containing 12 µl/cm$^2$ human Liberian immune serum as defined above. The plates were washed and pressed three times and stained with Coomassie brilliant blue R250.

Saponin treated Parasite Antigens

Parasite cultures were centrifuges at 2400×g for 5 min. Cell pellets were washed in 5 volumes sterile 0.9% NaCl, centrifuged at 2400×g for 5 min and incubated in 5 volumes of a 0.01% saponin solution in sterile water for 10 min, at room temperature. After centrifugation at 4500×g for 10 min, the saponin treatment was repeated and the pellets were finally washed in 5 volumes of sterile isotonic NaCl and centrifuged at 800×g for 10 min. The cell pellet was discarded and the supernatant was used for SDS-PAGE.

Lymphocyte Proliferation Assay

Heparinised venous blood was collected from Gambian donors. Non-immune (control) samples were obtained from from Europeans expected not to be malaria-immune.

Lymphocyte proliferation assays were performed as described previously (Riley, E. M. et a., 1988). Briefly, mononuclear cells (MNC) were separated by density centrifugation and stimulated with Purified Protein Derivative of tuberculin (PPD) or with Phytohemagglutinin (PHA) or control buffer containing β-galactosidase. Assays were performed in triplicate in round-bottomed microtiter plates and cultures were incubated for either 3 days (PHA) or 7 days (PPD and antigens) at 37° C. in 5% $CO_2$. Proliferation was determined by $^3$H-thymidine incorporation. A stimulation index of >2,5 considered to be indicative of a positive response.

Materials for Cultivation of the Recombinant Bacteria Used

LB medium: 10 g NZ amin, 5 g yeast extract (Difco), 5 g sodium chloride, 2 g magnesium sulphate.$7H_2O$, adjusted to pH 7.5, distilled water to 1 liter. The components were autoclaved at 120° C. for ½ hour and then stored in sterile bottles at 4° c.

LB plates with agar: 10 g NZ amin, 5 g yeast extract (Difco), 5 g sodium chloride, 15 g agar (Difco), volume adjusted to 1000 ml with distilled $H_2O$ and the total composition autoclaved at 120° C. for ½ hour and distributed in Petri-dishes, the plates optionally being supplemented with 50 mg/l ampicillin (Ampicillin obtained from DAK).

LB top agarose sued for λgt11 in Y1090; 5 g NZ amin, 2.5 g yeast extract (Difco), 2.5 g sodium chloride adjusted with distilled water to 500 ml, 0.35 g agarose in each 100 ml bottle. 50 ml of the above solution was poured into each 100 ml bottle were and all bottles autoclaved at 120° C. for 20 minutes.

Buffers Used for SDS-PAGE

Electrode buffer: 0.025M Tris.glycine pH 8.3, 0.1% SDS.

Transfer buffer: 0.25M Tris.glycine pH 8.3, 20% methanol.

Western Blot washing buffer: 0.1M Tris-hydrogen chloride pH 7.4, 0.5% TWEEN 20, 0.5M sodium chloride.

Buffers Used for Immunosorbant Columns

Column buffer: 0.02M Tris-barbital pH 8.6, 0.5M sodium chloride, 15 mM NaN$_3$.

Elution buffer: 3M potassium thiocyanate (KSCN) and Tris-barbital 0.02M pH 8.6, 5.5. diethylbarbituric acid (merck, article 276) Tris-tris 7-9 (Sigma No. T1378), potassiumthiocyanate (Merck, article 5125), Trizma base (Sigma No. T1503), gel filtration buffer: PBS pH 7.4 with sodium azide=PBSA.

EXAMPLE 1

Cloning of the Gene Encoding GLURP

*P. falciparum* culturing was performed as described by Jepsen, S. and B. J. Andersen in (2) and by Trager W. and J. B. Jensen in: Human malaria parasites in continuous culture. Science, 193:673–675;1976. DNA was extracted from the parasites of the schizont stage present in the red blood cells according to the following procedure:

1. The red blood cells were sedimented by gravity.
2. ⅔ of the medium was removed carefully so as not to stir the red blood cells.
3. The suspension was centrifuged at 200 g$_{av}$ for 5 minutes and the supernatant was removed.
4. The cell pellet was washed in a volume of isotonic saline constituting approx. 5 times that of the pellet and centrifuged at 2000 g$_{av}$ for 5 minutes.
5. The pellet was resuspended in 0.01% saponin in isotonic saline and incubated for 10 minutes at room temperature.
6. Centrifugation at 3000 g$_{av}$ for 10 minutes.
7. The pellet was resuspended in a volume of 0.01% saponin in isotonic saline constituting aprox. 5 times the volume of the pellet and incubated at room temperature for 5 minutes followed by centrifugation at 3000 g$_{av}$ for 10 minutes.
8. The pellet was washed in a volume of isotonic saline constituting approx. 5 times the volume of the pellet and centrifuged at 3000 g$_{av}$ for 10 min.
9. The pellet was suspended in a volume of DNA buffer (100 mM Tris-HCl pH 8.0, 1% SDS, 50 mM EDTA, 0.2M NaCl) constituting approx. 5 times the volume of the pellet.
10. RNase A which had been boiled for 10 minutes was added to 50 microgram/ml and the suspension was incubated at 37° C. for 1 hour.
11. Proteinase K was added to 100 microgram/ml, and the suspension was incubated at 50° C. for 1 hour.
12. Phenol extraction and ethanol precipitation were performed according to Maniatis, T. Fritsch, E. F. and Sambrook J.: Molecular cloning—a laboratory manual, Cold Spring Harbour Laboratory, 1982 pp. 458–459 and 461–462.
13. The pellet was redissolved in a suitable volume of 10 mM Tris-HCl pH 7.5, 1 mM EDTA.
14. The concentration of DNA was estimated by measurement of OD$_{260}$ and OD$_{280}$ according to Maniatis et al., op cit., p. 468.

Five ml of a solution of 100 microgram DNA/ml was placed in a syringe with a 25 Gxl cannula, all was stored on ice for 1 hour. The DNA solution was pressed rapidly out of the syringe so as to shear the DNA. This resulted in the formation of the DNA molecules having an average size of 20 kbp as measured by gel electrophoresis. Phenol extraction was performed as described above and EDTA was added to a concentration of 25 mM. An isopropanol precipitation was performed as described in Maniatis, Fritz, Sambrook, Molecular Cloning, A Laboratory Manual, Cold Spring Harbour Laboratory, 1982, pp. 461–462. DNA fragments were made blunt ended by filing out with T4 DNA polymerase in the presence of the four types of deoxynucleotide, as described in Maniatis op. cit., p. 117–121. EcoR1 linkers from New England Biolabs were ligated to the DNA fragments as described in Maniatis op. cit., p. 243–246. The resulting DNA fragments with EcoR1 linkers were digested with EcoR1 (Boehringer-Mannheim) and ligated to lambda gt11 arms (Promega Biolabs). The ligations were performed with T4 DNA ligase (Amersham). The recombinant lambda genomes were packaged with a packaging mix (Promega biolabs) according to the instructions of the manufacturer. The library was then used to infect Y1090 and plated on LB medium with agar. Nitrocellulose Blots (BA85 membranes, Schleicher und Schuell) of 100,000 plaques were screened with malaria antibodies to detect clones expressing malaria proteins (Young R. A. and R. W. Davis: Yeast RNA Polymerase II genes; Isolation with /Antibody Probes. Science, 222:778–782;1983), the visualization was performed with a pig antihuman IgG antibody conjugated to horseradish peroxidase (DAKOPATTS P214) followed by a peroxidase staining (Heegaard, N. H. H. and O. J. Bjerrum: Immunoblotting. General principles and procedures. In: Handbook of immunoblotting of proteins, Eds. O. J. Bjerrum and N. H. H. Heegaard. CRC Press, Boca Raton, Fla., 1987).

Sequencing

Restriction fragment length mapping was performed, and fragments of convenient length and localization were subjected to the Sanger didecry termination sequencing technique using single (Sanger R. Determination of nucleotide sequences in DNA. Science, 214:1205–1210;1981) and double stranded (United States Biochemical, Editorial Comment, 14:5;1988)DNA from M13 (M13 cloning and sequencing handbook. Amersham Internal plc, 1984) pUC9 Viera J. and J. Messing. Gene 19:259-;1982) and lambda gt11 (Huynh T. V., R. A. Young and R. W. Davis; Constructing and Screening cNDA Libraries in lambda gt10 and lambda gt11. In: DNA cloning: A practical approach, Volume 1, ed. D. M. Glover, IRL Press, Oxford, 1985), respectively. Digestions of the insert was performed with exonuclease III (the Erase-a-base system from Promegå, USA) in order to produce fragments of a length suitable for the sequencing of the 3' region of the gene being a highly repetitive region. The procedure of the manufacturer was followed.

Lysogenization

The plaque estimated to be of value was picked with a Pasteur pipette, put into SM-medium (Maniatis et al., op cit., p 70) and shaken at room temperature for 2 hours after which the phages were liberated to the medium.

The phage clone (termed Φ15) selected for lysogenization was initially amplified as described by Huynh H. et al., Constructing and screening cDNA libraries in lambda gt10 and lambda gt11, in DNA cloning—a practical approach., IRL Press 1985. The amplified phagestock, having a titer of $>10^{10}$ plaque forming units/ml, was used for infection of *E. coli* Y1089 to establish the Φ15 as a lysogen in the bacteria. 100 μl of a suspension of Y1089, $10^8$ cells/ml, prepared as described in the reference above and mixed with 100 μl of the abovementioned phage stock was used, giving a multiplicity of $10^4$ which is $10^3$ more than usually recommended. The procedure in the above reference p. 76 was otherwise followed. 10 μl of this mixture was then diluted 1:10000 in LB medium and 1, 10 and 100 μl of this dilution were spread on LB medium with agar. The spreaded volume was always at least 100 μl. The plates were incubated over night at 30° C.

The colonies on the plates were tested for temperature sensitivity by spreading bacteria from each colony on identically marked places of the two LB plates, and subsequently placing the plates at 30° C. and 42° C., respectively. Colonies growing at 30° C. but not at 42° C. are assumed to be lysogens.

Production of Fusion Protein Using Φ15 Lysogens

A temperature sensitive colony was used for inoculation of an Erlenmeyer flask with LB medium supplemented with 50 mg/l ampicillin which was incubated overnight at 30° C. The resulting culture was used as the start culture for the production of proteins. The overnight culture was diluted 1/100 in fresh LB medium supplemented with 50 mg/l ampicillin. The culture was incubated at 30° C. in an orbital shaker until an $OD_{600}$ of 0.5 was reached and at that time the temperature was abruptly increased to 42° C., and maintained at that temperature for 20 min. Then IPTG (Isopropyl β-D-thiogalactopyranoside obtained from Sigma Biochemical Company) was added to the culture to a final concentration of 10 mM and the growth was continued to the moment before the cells lyse as determined by experience, which for Φ15 was about 1 hour.

The culture was centrifuged at 27° C. at 2000 $g_{av}$ for 10 minutes, the pellet resuspended in PBS (1/10 the volume of the culture), sonicated 3×20 seconds at maximum output (150 watt MSE Ultrasonic disintegrator), and frozen at −80° C.

Analysis of the lysates by sodium dodecyl sulphate polyacrylamide gel electrophoresis (SDS-PAGE) and Western blotting was performed with the BioRad Protean 2 system as described in MATERIALS AND METHODS, with sera from non-immune donors diluted 1:800 and affinity purified antibodies against antigen 1 diluted 1:200, cf. FIG. 11.

Comparison between DNA from Different Malaria Isolates

DNA obtained from malaria isolates from Burma, Thailand, Papua NG, India, Liberia, Senegal, and Tanzania in the above explained manner was digested with BclI and a Souther Blot performed. All isolates hybridized with the insert from Φ15. At least two bands were expected because the Φ15-insert contains an internal BclI cite. In four cases a third band at ≈1.7 kb was observed, which might be due to partial digestion. The Southern Blot is shown in FIG. 12.

EXAMPLE 2

Figure 2:
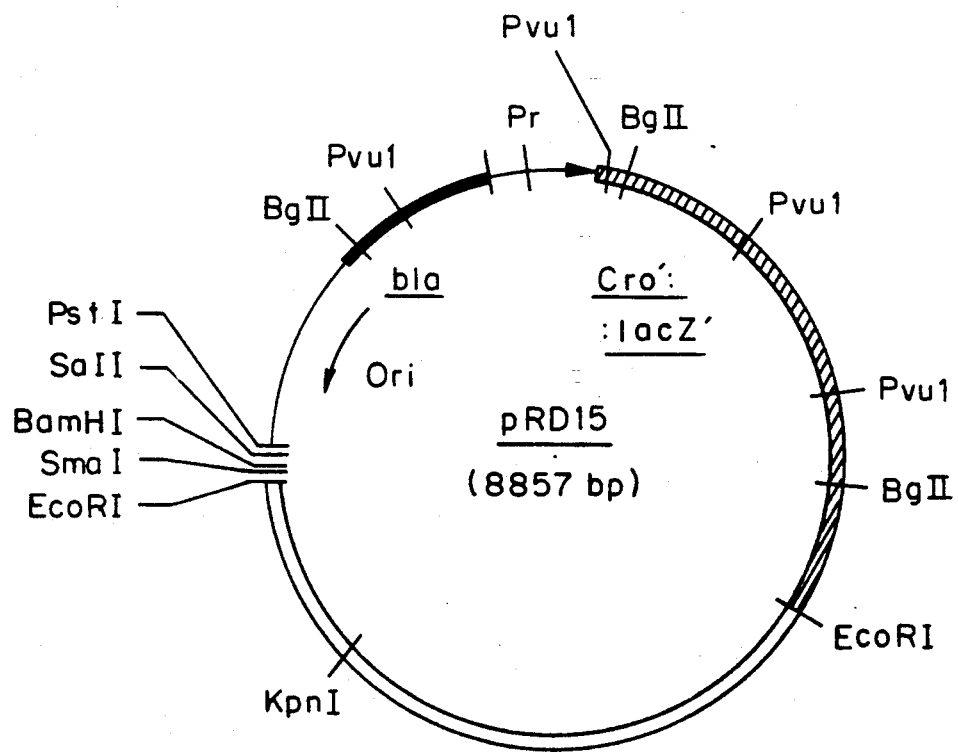
FIG. 2 is a map of the plasmid pRD15 constructed of the plasmid pEX2 containing the Φ15 insert in its EcoRI restriction enzyme cleavage site. Unique restriction enzyme cleavage sites and the most important non-unique restriction enzyme cleavage sites are indicated (BamHI, BgII, EcoRI, KpnI, PvuI, PstI, SalI, SmaI). The abbreviations indicate.

Production of β-galactosidase and Subcloning of the Φ15 Insert into the pEX2 Vector DNA from the Φ15 lysogen Y1090 *E. coli* was prepared according to standard procedures described in Maniatis et al., (pp. 76–94). To excise the Φ15 inset originating from *Plasmodium falciparum*, the DNA was digested with the restriction enzyme EcoR1 from Amersham using 10 units per μg DNA for one hour at 37° C. A buffer consisting of 100 mM Tris-HCl, ph 7.5, 50 mM sodium chloride and 10 mM magnesium chloride was used. The expression vector pEX2 described in EMBO. J. vol., 3, 1984, pp. 1429–1434, C. S. Stanley and J. P. Luzio and purchased from Boehringer-Mannheim, was digested with EcoR1 as above. The digested pEX2 was dephosphorylated with bacterial alkaline phosphatase in a buffer consisting of 15 mM Tris-HCl pH 7.5, 10 mM 2-mercaptoethanol and 0.05% bovine serum albumin and incubated at 25° C. Excised Φ15 inserts and dephosphorylated linearised pEX2 vectors were mixed and ligated at 4° C. overnight with T-4 DNA ligase from Amersham. Essential features of this construction is illustrated in FIG. 2.

Transformation of the Recombinant pEX2 into *E. coli* POP 2136

The recombinant pEX2 was transformed to *E. coli* POP 2136. POP 2136 is a λphage derivative which has been constructed in the following way: first the 2.3 kb BGlII fragment of λ phage, carrying the CI8957 allele and the $P_R$ promoter, was cloned into the BamHI site of a polylinker as shown below:

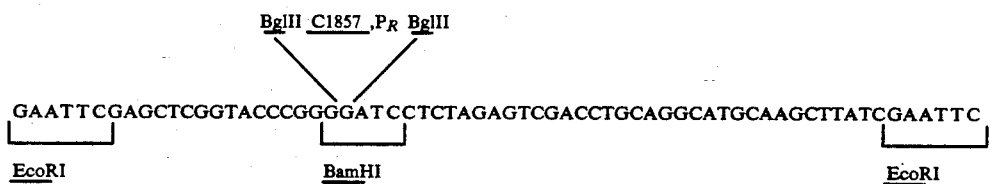

The EcoR1 fragment thus obtained was then cloned into the EcoR1 site of pOM41 and transferred onto the chromosome of an *E. coli* C600 strain (Mal⁻ Tet$^R$ selection at 30° C.; Gene, 29, pp. 231–241). Finally, by P1 cotransduction with the proximal marker aroB, this structure was introduced into the MM294 background (F⁻endA thi hsdR).

POP2136: orientation malT, $P_R$, CI857, malPQ

The resulting POP2136 is Mal⁻ at both temperatures, 30° C. and 40° C., and is λimmune.

To prepare competent *E. coli* cells, the Hannahan Method was used (D. Hannahan, Technics for Transformation of *E. coli* in DNA cloning, Vol. 1, A Practical Approach, chapter 6, edt. by D. M. Glover, IRL Press 1985). Transformed cells were selected on LB-plates with ampicillin and transformants were screened using small-scale isolation of plasmid DNA as described in Maniatis et al., chapter 11. The isolated plasmids were digested with Sca1 (from Amersham) and BamH1 (Boehringer-Mannheim) for 1 hour. Buffer used for Sca1: 6 mM Tris-HCl, 150 mM sodium chloride, 6 mM magnesium chloride, 6 mM 2-mercaptoethanol bovine serum albumin, 100 μg/ml, pH 7.5, at 37° C. Buffer used for BamH1; 10 mM Tris-HCl, pH 8.0, 7 mM magnesium chloride, 100 mM sodium chloride, 2 mM 2-mercaptoethanol, 0.01% bovine serum albumin at 37° C. The digests were analysed on a 1% agarose gel, separation time 4 hours, 100 Volts. Clones that gave rise to an essentially linearised recombinant pEX2 (the distance between the Sca1 and BamH1 sites are a few hundreds of bases) were chosen for further characterization. The clone which gave the highest level of protein with a molecular weight of 300 kD and which in a Western Blot showed reaction with malaria-immune serum was chosen for further expression of the fusion proteins.

This clone has been deposited with Deutsche Sammlung von Mikroorganismen, DSM, on 15 Sep. 1988 under Accession No. 4815.

Expression of β-galactosidase::GLURP in *E. coli*

The clone selected for further expression (DSM 4815) was maintained on LB plates supplemented with ampicillin and stored at 4° C. Longer term storage was secured by −80° C. storage of an overnight culture supplemented with glycerol to 20%. An overnight culture grown at 28° C. and supplemented with ampicillin to 50 mg/l. Recombinant bacteria were grown in Preg1 flasks on an orbital shaker at 28° C. until the $OD_{600}$ reached 1.0 The temperature was increased to 42° C. for 1 hour and cultivation continued until the $OD_{600}$ reached approximately 5.0, and not for more than 4 hours.

Purification of Inclusion Bodies

The *E. coli* cells were then harvested by centrifugation in a Sorval superspeed centrifuge using the GS-3 head at 5000 r.p.m. (2000 $g_{av}$) for 10 minutes at room temperature. The pellet was then resuspended in TEN (50 mM Tris-HCl pH 7.5, 0.5 mM EDTA, 150 mM sodium chloride). The pellet was resuspended in 1/100 the volume of the original culture of TEN, and the cells were disintegrated in a French press from American Instruments Company, Maryland, USA, at a pressure of 18000 psi. The material was centrifuged at 4000 $g_{av}$ at 4° C. for 10 minutes and the supernatant discarded. The pellet was washed in a volume of TEN equivalent to 1/100 of the original culture volume. The suspension was again centrifuged for 1000 $g_{av}$ for 10 minutes at 4° C. This procedure was performed two more times. The resulting pellet consisting of inclusion bodies was resuspended in 1/100 the volume of the original culture of denaturing buffer consisting of 5M guanidinium-HCl, 50 mM Tris-HCl, pH 8.0, 1 mM dithiothreitol, 1 mM EDTA. The material was left overnight to be gently shaken at 4° C. Soluble material was separated from insoluble material by centrifugation: 36000×G for 1 hour. The supernatant was then passed over a Sephacryl S300 (900 mm×26 mm column) obtained from Pharmacia. The gel filtration was performed at 4° C. The Sephacryl S300 column was equilibrated with one bed volume of the denaturing buffer mentioned above. Flow rate was 40 ml per hour of a PBS-buffer, pH 7.4. Fractions were collected and dialyzed against 50 times the volume of PBS overnight at 4° C. for analysis. For production, the following refolding procedure was used: the fractions containing substantial amounts of fusion protein were pooled and dialysed against 5M urea, 20 mM Tris HCl pH 7.5 and 1 mM DTT at room temperature for 3 hours. The urea concentration was then lowered gradually to zero over a period of approx. 10 hours, maintaining the DTT concentration at 1 mM. At zero molar urea, the DTT concentration was lowered to zero, the dialysis being against, e.g., 20 mM Tris HCl pH 7.5 at room temperature for approx. 2 hours. The purpose of this procedure was to keep the fusion protein solubilized. The procedure allowed 1) the protein to fold to its normal structure and 2) to regain its internal disulphide bridges. In case a too high rate of precipitation is observed, the procedure is repeated with the protein dissolved in 5M urea, 20 mM Tris HCl pH 7.5 and 1 mM DTT.

Analysis of the fractions on sodium dodecyl sulphate polyacrylamide gel electrophoresis (SDS-PAGE) was performed with the BioRad Mini-protean 2 system as described in MATERIALS AND METHODS. Fractions shown to contain reasonable amounts of fusion protein were pooled. Western Blot analysis was performed with the pool as described in MATERIALS AND METHODS. Blots were incubated with immune sera from Liberia in a dilution 1:800.

Further purification of the GLURP::β-galactosidase fusion protein was obtained by the following procedure:

Parts of the fractions obtained from fraction collector were analysed for their composition regarding the fusion protein and the *E. coli* proteins. Fractions predominantly containing fusion protein were pooled and concentrated. The concentration procedure was performed by establishing an osmotic gradiant between the fusion protein containing solution inside a bag of dialyses membrane and PEG20000 flakes deposited on the outside of the bag. Using this method, the fusion protein remained in a buffer consisting of guanidinium hydrochloride, DTT and pH maintaining buffer of the required concentrations. The volume of the pool fraction was thus reduced to a volume optimal for application on the gel filtration column, e.g. 10–15 ml. This procedure was repeated one more time resulting in a total separation of the fusion protein and the *E. coli* proteins corresponding to 2700 mm gel filtration. This extension of the gel filtration purification was performed on a S400HR gel filtration matrix obtained from Pharmacia-LKB. This type of matrix gave better separation characteristics and had better flow properties than the previously mentioned S300 (See FIG. 13 and 14).

For quantifitation of the content of fusion protein in various fractions, an ELISA (Enzyme-linked Immunosorbant Assay) based on the principle of capturing the fusion protein with rabbit anti-fusion protein antibodies has been used, and detection with mouse anti-fusion protein or monoclonal mouse-anti-β-galactosidase antibodies or human serum has been used.

Further purification of the fusion protein (refolded as outlined above) may be performed as follows: A column with mouse monoclonal anti-β-galactosidase antibodies coupled to CNBr sepharose 4B, obtained from Pharmacia is used. The antibodies used are purified from hybridoma supernatants using a protein A and/or a fusion protein column and are coupled to the cyanogen bromide activated Sepharose according to the procedures of the manufacturer. Pooled fractions from gel filtration shown to contain the major part of the fusion protein are applied to the column; the amount of fusion protein not exceeding the total binding capacity of the column. This is monitored by examining the passage with the ELISA utilizing the anti-$\beta$-galactosidase antibodies.

The column is then washed with 3 bed volumes of column buffer and eluted using 3M potassium thiocyanate (KSCN) in column buffer without NaCl. The collected fractions are dialyzed against PBS and analyzed using the ELISA for detection of $\beta$-galactosidase. Concentration to approx. 2 mg/ml is performed in an Amicon diaflow concentrator cell. To remove any lipopolysaccharide from E. coli the material is passed through a polymyxin B column and checked for endotoxin activity by use of the limulus amoebocyt lysate assay.

Methods Used for Estimation of Purity of Fusion Protein Preparations

During the purification, the following techniques were used for monitoring the purity of fusion protein preparations: continuous UV-monitoring of chromatographical procedures, SDS-PAGE of selected fractions of eluates, and immunoblotting of separated proteins reacted with antibodies appropriate for the aim of the examination, e.g. anti-E. coli antibodies for the estimation of the purity regarding E. coli-proteins.

During the development of the purification procedures described above, considerable experience was obtained regarding the UV-absorption profile produced by the eluates from different preparations of harvested cells. The application of the soluble fraction of whole cells being processed in the French Press to the gel filtration column resulted in a rather broad extended absorption, see FIG. 13A. A clear difference was observed when applying a preparation of processed cells being processed according to the principles of inclusion bodies as described above. When inclusion bodies were sued, a peak appeared immediately after void volume, FIG. 13B. When this peak was collected, concentrated and recycled, further sharpening of the UV-absorption profile was noted, FIG. 13C. This was even more marked after a second recycling (a total of 2700 mm of gel filtration), FIG. 13D. The purity of peaks was continuously monitored by SDS-PAGE. This was subsequently stained by Coomassie blue. This staining method provided a quantitative colouring of proteins present in the gel, FIG. 14. An unbiased way to read gels stained by Coomassie blue could be densitometric scanning of gels and then relating the staining of bands representing fusion protein to total staining of the gel. For a qualitative evaluation of the gel, a silver staining could be applied.

It is important to bear in mind that even if a gel shows proteins of molecular weights differing from that of the intact fusion protein, this might not invalidate the purity of the preparation as these bands might represent degradation products originating from the intact protein. This can be analysed in immunoblotting reacted with e.g. immune serum or rabbit anti-fusion protein antibodies. Degradation is observed during storage of fusion protein preparations for more than six months, especially for diluted preparations.

By the above-mentioned methods, the substantial purity of the fusion protein was demonstrated.

EXAMPLE 3

Analysis of the Similarity of the Fusion Protein and the Native Protein from the Malaria Parasite In order to estimate the similarity of the fusion protein, GLURP, produced in E. coli with native GLURP from P. falciparum, a competition assay was performed. The assay was performed in two phases:
1) an absorption phase were antibodies from human malaria-immune serum reacted in an ELISA well with a coating of the fusion protein,
2) the liquid phase from the first phase, depleted of anti-fusion protein antibodies, was transferred to an ELISA well where the native protein from culture supernatant was presented to the residual antibodies on a rabbit anti-fusion protein antibody.

Two controls were included in this study:

The first was the transfer of the liquid phase to a well where the coating of rabbit anti-fusion protein antibodies had not been exposed to the supernatant from a P. falciparum in vitro culture, but had been exposed to the medium which is used for the in vitro culture. That is a material with a composition identical to the supernatant except for the fact that it contains no P. falciparum antigens. This control establishes the background which is quite high due to the content of anti-rabbit IgG antibodies in almost all human serum samples.

The other control was coating of the first phase absorption ELISA wells with $\beta$-galactosidase obtained from Boehringer-Mannheim. $\beta$-galactosidase is the non-malarial part of the fusion protein. This control was included to rule out the possibility of unspecific interaction of antibodies and the non-malaria part of the fusion protein or the possibility that the absorption was due to a non-specific interaction of any protein in an ELISA well and the antibodies in the serum.

For coating the ELISA plate used for absorption of anti-fusion protein antibodies a preparation of fusion protein with a concentration of protein of 1 mg per ml was used. The amounts of fusion protein applied to the wells ranged from 6.25 $\mu$g to 770 pg. All experiments were performed in duplicate. A well not coated with fusion protein, but blocked with blocking buffer was used as an example of an unlimited dilution of the fusion protein. Dilutions were performed in carbonate buffer pH 9.6 and coating and blocking were performed according to standard procedures. The absorption of human malaria-immune serum (IS149) diluted 1:2000 in dilution buffer was performed for two hours at room temperature on a shaking table. A volume of 110 $\mu$l of immune serum was applied to each well. After absorption, a volume of 100 $\mu$l was pipetted into the wells containing native malaria antigen presented on rabbit anti-fusion protein antibodies. These wells were prepared exactly as described in the paragraph describing the antigen detecting ELISA. The absorbed human serum reacted with native protein for one hour. The presence of human antibodies was detected with rabbit anti-human IgG (DAKOPATTS P214) diluted 1:1000. Visualization was performed according to standard procedures with colouring substrate. Optical densities were measured at 490 nm. Percent inhibition exerted by a given amount of fusion protein was calculated by subtracting the OD obtained on a coating of culture medium presented on rabbit-anti-GLURP antibodies form the OD obtained on a coating of culture supernatant presented on the same antibodies and dividing by the difference between the maximum OD value obtained with an unabsorbed human-immune serum of the above mentioned dilution reacting with a coating of culture supernatant presented on the above mentioned antibodies and the OD value obtained by the reacting of the unabsorbed human-immune serum with a coating of culture medium presented on rabbit-anti-GLURP antibodies. That is, percent inhibition (P) by given absorption, (Z) is calculated as shown below.

$$P = \frac{OD(Z, \text{culture supernatant}) - OD(Z, \text{culture medium})}{OD(\text{unabsorbed, culture supernatant}) - OD(\text{unabsorbed, culture medium})}$$

This experiment showed that even at the high dilutions of fusion protein used for coating of the absorption wells, a clear inhibition effect was noted on the reaction of the human malaria-immune serum with the native protein. Absorption wells coated with amounts of $\beta$-galactosidase corresponding to the amounts of fusion protein used did in no way affect the binding of human antibodies to the native protein. The maximum inhibition of binding of human antibodies to the native antigen was approximately 92%. This result shows that the protein produced in *E. coli* and renatured as described contains 92% of the epitopes possessed by the native protein produced by *P. falciparum*. FIG. 15.

EXAMPLE 4

Use of Fusion Protein as the Antigen in an ELISA Aimed at the Detection of Antibodies Directed against *Plasmodium falciparum*.

Fusion protein from a solution containing 2 mg/ml in PBS, pH 7.4, was used for the coating of an ELISA plate in amounts of 0.16 $\mu$g per well in a volume of 100 $\mu$l of a carbonate buffer, pH 9.6. The plates were left overnight at 4° C. in a humid chamber. (Coating of the ELISA plates can alternatively be performed by incubation for 2 hours in the humid chamber at room temperature on an orbital shaker.) Washing was performed with a Technunc Immunowasher 12 using the washing buffer. Each well was flooded with buffer 4 times. After washing, the plate was emptied and 100 $\mu$l of a conservation buffer applied to each well. The ELISA plate can not be stored for at least two months at 4° C. Serum from 1) a control group of Danish donors (presumably never exposed to malaria), 2) Liberian donors (probably exposed to malaria), 3) Danish patients having diagnosed toxoplasmosis, and 4) Danish patients having diagnosed schizostomiasis (=bilharziosis) to be tested was diluted in a dilution buffer 1:200 and 100 $\mu$l was applied to each well. Each sample was tested in two wells. The plate was then placed at room temperature on an orbital shaker for one hour. The washing was performed as described above and all fluids in the ELISA plate removed. A rabbit anti-human-IgG conjugated to horseradish peroxidase (Dakopatts P214 dilution 1:10,000) was then applied to the well in a volume of 100 $\mu$l. (For detection of antibodies in species other than the human, the horseradish peroxidase conjugated antibody is directed against the IgG of the species in question.) The plate was incubated at room temperature for one hour on an orbital share, then washed and emptied as described above. 100 $\mu$l of colouring buffer was applied to each well and the plate incubated for 1 minute. The colouring buffer was removed from the wells and 100 $\mu$l of colouring substrate applied to each well followed by incubation for 20–30 minutes. The colouring process was stopped by applying 150 $\mu$l 1M sulfuric acid to each well. The optical density at 490 nanometers was measured on a Titertek ELISA reader and the results are illustrated in FIG. 6. The ratio between positive and negative readings was about 15, which is very satisfactory. The average of the 93 Danish donors was approx. 0.067 absorbance units with a standard deviation of 0.057. A typical value for a malaria-immune patient was above 1.5 The negative results obtained from the African donors were verified by analysis of the sera by use of crossed immune-electrophoresis. Thus, the group of Liberian donors giving values below the 95% did not have any precipitates interpreted as GLURP in CIE. These patients probably have not had malaria due to pharmaceutical prophylaxis or a place of living with no malaria transmission, i.e. in the capital of Liberia.

The detection of antibodies against the fusion protein sometimes has to be carried out in species against the antibodies of which one does not possess antibodies. This, for example, was the case in the immunization experiment carried out in the monkeys mentioned in Example 12C. This obstacle was initially circumvented using a competitive ELISA principle. Later on, rabbit-anti-monkey serum antibodies were available. In this assay, ELISA plates coated with fusion protein in usual amounts were used. The monkey antibodies in varying dilutions from 1:5–1:640 were put into the wells of the above mentioned ELISA plates in a volume of 50 $\mu$l per well. The monkey antibodies were incubated alone in the wells for 15–30 minutes after which period of time 50 $\mu$l of a human immune serum was applied. The dilution of human immune serum was chosen so as to put the human antibody on the linear part of the titration curve in order to obtain the maximum variation in the amount of antibody bound to the fusion protein coating. Incubation was prolonged 1 hour after the addition of the human serum. Binding of human immunoglobulins was detected by rabbit anti-human immunoglobulin antibodies (P214) diluted 1:10000. Visualization was performed as above.

QUANTIFICATION OF GLURP

Measurements of GLURP in serum or secretions from human or animal bodies, especially in urine, can be performed using the ELISA technique or using the principle of competitive ELISA. A diagnostic tool based upon the principle of competitive ELISA, possibly performed on serum or urine in a one-step procedure are valuable embodiments of the invention. The quantification of GLURP is illustrated in Examples 5–7.

EXAMPLE 5

GLURP Detecting ELISA

Malaria antigen was detected in culture supernatant from *P. falciparum* in vitro culture using the following construction of an ELISA. Rabbit anti-fusion protein antibodies were purified form rabbits immunized as described in Example 12A. The purification of the antibodies was according to the procedure of Harboe, N. and Ingild A.: Immunization, isolation of immunoglobulins and estimation of antibody titer. Scand. J. Immunol. 2, suppl. 1:161, 1973. The concentration of the stock of purified IgG was 4 mg per ml. As a reasonable compromise between sensitivity and consumption of antibody, we used a dilution of the antibody stock of 1:320 corresponding to an application of 1.2 μg of IgG to each well. The antibodies were applied to the well diluted in carbonate buffer pH 9.6. Coating was performed for two hours at room temperature or alternatively over night at 4° C. The plate was washed four times, emptied and 100 μl of blocking buffer were added and incubated for at least one hour at room temperature. The specimen to be analysed for the presence of GLURP was diluted in dilution buffer and applied in a volume of 100 μl to the well. All measurements were made in duplicate. As the test material we have used supernatant from in vitro malaria culture diluted 1:5 to 1:2816. Medium for *Pl falciparum* in vitro culture served as negative control. The antigen was incubated in the well for at least two hours, preferably over night. The detection of binding of GLURP to the rabbit antibodies coated to the bottom of the well was performed either by the use of human anti-*P. falciparum* antibodies or by the use of mouse anti-fusion protein antibodies (see Example 12B). Human antibodies were used in dilutions of 1:200 to 1:2000. Antibodies applied for this purpose were incubated for one hour at room temperature on a shaking table. The dilution of the mouse anti-fusion protein was 1:500 to 1:1000. The binding of human antibodies to GLURP was detected with rabbit anti-human IgG (DAKOPATTS P214) diluted 1:1000. The binding of mouse antibodies was detected using a rabbit anti-mouse IgG conjugated to peroxidase (DAKOPATTS P260) diluted 1:1000.

To test the sensitivity of the GLURP ELISA and to estimate its ability to quantitate GLURP, culture supernatants from in vitro *P. falciparum* (F32) cultures with known parasitemias were used as the specimens. The parasitemias ranged from 4% to 20%. The hematocrite was constantly 6%, see FIG. 16.

The conclusions of the above mentioned experiments were that the detection of the binding of GLURP with human antibodies was satisfactory when the content of human IgG in the specimen was low or zero, but the background rose to higher levels when the specimen tested was, for example, human immune serum. The mouse anti-fusion protein antibodies functioned satisfactorily even if the specimen tested was human serum. This has been tested with Danish donor sera presumed not to contain malaria antigens. These specimens had optical density readings of 0.1 to 0.2. Experiments performed with culture supernatant from the F32 Tanzania isolate showed that there was a signal to noise ratio of approximately 4, even at a dilution of 1:2816. This detection method is usable for isolates of *P. falciparum* from Brazil and Honduras, and antibodies recognize proteins from isolates from Indochina, India and Liberia. Therefore, this method for diagnosing the presence of antigen is supposed to be without geographical limitations.

The above described ELISA was used for comparison of the contents of protein in various batches of the fusion protein with the contents of a β-galactosidase standard. This was done in order to estimate the contents of different batches. For this purpose, the detecting antibody was mouse monoclonal anti-β-galactosidase antibodies (from the Hybridoma Laboratory SSI, Mgal 8).

The sensitivity of the GLURP detecting ELISA used for detection of GLURP in blood, serum or urine may be further increased by the use of affinity purified antibodies both in the capturing and in the detection layers. One or both of these layers may consist of monoclonal antibodies. Furthermore, these layers may be composed of antibodies, enzymatically processed to Fab fragments. Further, the detecting antibody may be directly labelled to the detecting principle, i.e. biotinylated, conjugated to peroxidase, conjugated to alkaline phosphatase, conjugated to Europium or the like.

EXAMPLE 6

Antigen Measurement Using Competitive ELISA

The wells of an ELISA plate No. 4-39454 from Technunc were each coated with 100 μl of fusion protein in a dilution of 1 μg to 1 ng per ml diluted with carbonate buffer, pH 9.6. The plate was left overnight at 4° C. in a humid chamber. Coating of the ELISA plates can alternatively be performed by 2 hours of incubation in a humid chamber at room temperature on an orbital shaker.

50 μl of the supernatant from in vitro *P. falciparum* culture was mixed with an equal volume of dilution buffer containing rabbit-anti-fusion antibodies in a dilution of 1:1600–1:12800. The mixture was put into the wells and incubated for 1 hour at room temperature on an orbital shaker. As the negative test specimen, the medium used for in vitro *P. falciparum* culture was used in dilutions corresponding to the dilutions of the culture supernatant. Alternatively, the mixture of antibodies and specimen is incubated for 15–60 minutes before application to the wells. This usually increases the sensitivity by a factor 10. Washing was performed as above. Porcine anti-rabbit antibodies conjugated to peroxidase (DAKOPATTS P217) was used in a dilution 1:1000, incubated for 1 hour on a rocking platform at room temperature. The plate was washed as described above. 100 μl of colouring buffer was applied to each well for 1 minute, then removed and 100 μl of colouring substrate was applied to the well. The colouring reaction was allowed to continue for 20–30 minutes, and then stopped with 150 μl, 1M sulfuric acid. The optical density at 490 nanometers was measured on an ELISA reader.

The main advantage of the competitive principle is the speed with which it can be performed. Generally it med that the detection limit for the presence of GLURP in culture supernatant was dilutions of 1:10–1:100. Generally it med that low concentrations of rabbit antibody to a certain extent increased the sensitivity as did low amounts of fusion protein in the solid phase.

An alternative design of the competitive ELISA is to coat the wells of the ELISA plate, as described above, with antibodies (obtained from any species or cell system by immunization with the fusion protein). A concentration of antibodies of 0.004 μg/ml to 400 μg/ml is carbonate buffer is used. 50 μl of the sample is mixed with 50 μl of a dilution of the fusion protein in dilution buffer. A series of consecutive dilutions is used, the dilutions ranging from 1 mg/ml to 1 pg/ml in dilution buffer or another range of dilutions which is found appropriate considering the type of sample.

The visualization of fusion protein bound to the antibodies in the well may be performed using a fusion protein labelled as described herein with a fluorescent molecule or an enzyme capable of hydrolyzing a substrate and thereby changing the absorbance of the substrate at a given wavelength or any other principle. Alternatively, an antibody directed against the β-galactosidase part of the fusion protein may be used to detect the presence of the fusion protein, either by using an anti-β-galactosidase antibody labelled itself or using another antibody with specificity against the anti-β-galactosidase antibody conjugated to any labelling principle in the next layer.

EXAMPLE 6

Detection of the Presence of *P. falciparum* in the Body by Examination of Urine Clinical observations indicate that an increased excretion of proteins and other substances from the blood stream to the urine is a very common phenomenon in patients suffering form malaria. This makes the urine a useful source of components derived from and being specific for the malaria parasite, i.e. proteins, DNA, RNA, lipids or the like.

The detection of proteins specific for *P. falciparum* can be performed as described in Examples 5 and 6. Preferably, the detection can be simplified passing the urine sample through a membrane coated with antibodies against GLURP thereby capturing GLURP and subsequently detecting the presence of GLURP by an antibody conjugated to an agent for visualization, i.e. alkaline phosphatase using the appropriate substrate.

The detection of DNA specific for *P. falciparum* can be performed as described in Example 9.

An evaluation of the diagnostic capabilities of these methods is currently carried out in collaboration with the MRC Research Station in the Gambia. Urine form individuals suffering from acute malaria has been collected, preserved with Sodium azide and frozen at $-20°$ C. before shipment to our laboratory.

An alternative design of an assay for the presence of GLURP in urine is to coat particles, e.g. latex particles, with antibodies against GLURP (obtained from any species or cell system by immunization with fusion protein). These particles are then suspended in a volume of the urine sample, if necessary in a buffer. The presence of GLURP in the urine will be detected as the occurrence of agglutination and precipitation of the particles.

EXAMPLE 8

Determination of the Optimal Amount of Antigen Used for Coating of ELISA-plate.

A study was performed with the aim of determining the optimum amount of antigen used for coating the ELISA plate. An ELISA plate was coated with decreasing amounts of protein starting with 100 ng/well (corresponding to 0.5 µl/well) of an aqueous solution of the fusion protein with a concentration of 2 mg/ml. The antigen was diluted in carbonate buffer, pH 9.6. Consecutive two-fold dilutions were applied to the ELISA plates. Five sera were used for this experiment. An immune serum from Liberia, a pool of immune sera previously giving a high OD, three sera from donors of which one was known to give a very low OD and two to give a medium OD reaction, although they had no known exposition for malaria antigens. These two sera represented the sera which are known to occur in all serological tests, the false positives. The experiment showed that the OD for the true positive sera increased to a maximum with an antigen amount 12.5 ng (0.0625 µl) per well, whereas the negative controls and the false positive donors with no known exposition decreased in the OD measurement with every dilution of the antigen amount used. The conclusion of the experiment was that the unspecific background can be reduced at least two-fold without change of the positive reactions.

EXAMPLE 9

Diagnosis of *Plasmodium falciparum* Infection using DNA Hybridization Techniques 1-5 ml of a blood sample was obtained from the individual or animal to be examine. The blood cells were sediments and the cells were lysed.

To perform the polymerase chain reaction (PCR) amplification as described by Saiki et al. in *Science*, 230, pp. 1350-1354, 1985 or in U.S. Pat. No. 4,683,202, the following material was used: 1 nucleotide probe (e.g. a 20-45 mer) complementary to the 5-prime region of the DNA sequence encoding GLURP and another nucleotide probe (e.g. a 20-45 mer) complementary to a region approx. 1500 bases 3-prime to the first-mentioned probe on the other DNA strand. Amplification was performed with the Taq polymerase for 20-60 cycles.

In a first experiment, the primer sets AC, AD and BD were tested, where:
A=5'-AAACCATTTGAAGAAATTGAAAAA-3'
B=5'-ATATCTTGTTTCTTTAAATTTTTTGT-3'
C=5'-TGATGGTACTTCTTCAATTT-CAACAATTTCTGGAAGAAT-3'
D=5'-CCTTTGCTATTCCTTTAATTGTACT-TACAC-3'.

Amplification with these primer sets using $5 \times 10^{-17}$ moles of purified chromosomal F32-DNA produced fragments of approximately the expected size: AC=1172 bp, AD=1656 bp, BD=108 bp. The amplification cycle used was 94° C. for 1 minute to denature the DNA, 65° C. for 2 minutes to anneal the primers and 72° C. for 8 minutes to run the polymerase reaction, repeated 35 times. The product of the amplification was checked by calculating the size of the DNA after agarose gel electrophoresis, the AD-product by calculating the size of fragments after restriction enzyme digestion of the amplification with KpnI.

The amplificate can be further analysed by transferring the DNA to a nitrocellulose membrane as dot Blot or Souther Blot, and hybridization performed using a suitable probe derived from glurp. To detect the occurrence of hybridization visually, either a radioactively labelled probe can be used, a probe labelled with a fluorescent molecule or a probe coupled to an enzyme which is able to hydrolyse a substrate, the hydrolysis of which is revealed by an absorbance variation for a given wavelength of radiation, e.g. to horseradish peroxidase. The visualization could be amplified using intermediate steps, e.g. involving a biotinylated probe reacting with avidin or streptavidin conjugated with an enzyme or a fluorescent molecule; alternatively a chemically modified probe reacting with an antibody directed against the chemical modification conjugated to an enzyme or fluorescent molecule. The visualization is then performed with the appropriate system, i.e. peroxidase staining and absorbance measurement, measurement of light emission or the like.

THERAPEUTICAL APPLICATIONS

EXAMPLE 10

Determination of Epitopes of GLURP

It is contemplated that peptides or proteins derived form the amino acid sequence of GLURP, as described herein, may be used for immunization purposes. These peptides or proteins could be fragments or rearrangements of the amino acid sequence produced in *P. falciparum*, alternatively produced in yeast, mammalian cell cultures or in any other organism, e.g. in *E. coli* as a fusion protein, in *E. coli* or in any other organism as the gene product itself, e.g. using the vector described by Nagai and Thogersen in Methods of Enzymology, vol 153, chapter 29, Academic Press inc., 1987, or alternatively, using the gene or components of the gene in any arrangement inserted in a vector, e.g. vaccinia, useful for gene transfer to the animal to be immunized and after transfer being able to express the gene product in a way that confers immunity to the animal against the malaria parasite. More specifically, it is contemplated to use the most immunogenic regions of the molecule, alternatively well characterized epitopes connected to each other or as separate components of a vaccine ensuring reactivity with both B- and T-lymphocytes and thereby immunizing the animal and securing an anamnestic response of the immune system against the malaria parasite.

a) B-lymphocyte epitopes

To localize the B-lymphocyte epitopes in the molecule of GLURP, it is contemplated to follow four approaches:
(1) to evaluate the antigenicity of the sequence of the GLURP using computer programmes as the Hopp and Woods analyses, the Lewitt analysis or the Surfaceplot (Synthetic Peptides Incorporated)
(2) to produce deletion mutants using the Erase-a-base system
(3) to produce a library of the gene by shearing it randomly and cloning the fragments in an expression vector
(4) to produce synthetic peptides of predicted epitopes, e.g. as described herein.

Approaches (2) and (3) should allow some of the conformational epitopes to be conserved although some will unavoidably be destroyed. The gene products from these clones are tested in an ELISA against immune sera to determined which areas of GLURP are the most important for the antigen-antibody recognition.

Gene fragments encoding immunologically important regions are sequenced to relate them to the nucleotide sequence and thereby to the amino acids sequence.

b) T-lymphocyte epitopes
1. Predictions by Computer Algorithms

To determine T-lymphocyte epitopes, the gene encoding GLURP was analyzed with the AMPHI program (Margalit et al. in *J Immunol*, 138, pp. 2213-2239, 1987). According to this analysis, potential helper T cell epitopes were the following sequences (which were also shown above), amino acid residues in parentheses:

(179-186) Val—Ser—Glu—Pro—Ala—Glu—His—Val;

(162-171) Lys—Ser—Val—Ser—Glu—Pro—Ala—Glu—His—Val;

(194-210) Thr—Ser—Glu—Pro—Ala—Glu—His—Val—Glu—Ser—Val—Ser—Glu—Gln—Ser—Asn—Asn;

(223-230) Lys—Pro—Phe—Glu—Glu—Ile—Glu—Lys;

(333-343) Glu—Val—Glu—Glu—Ile—Pro—Ser—Glu—Leu—His—Glu;

(600-613) Glu—Ile—Leu—Pro—Glu—Ile—Val—Glu—Ile—Glu—Glu—Val—Pro—Ser;

(690-696) Gly—Pro—Lys—His—Val—Glu—Gln;

(739-774) ISTKKFKKVSQTIVSVMINAYDGVIQVVSTIKGIAK.

These sequences all have a potential for having the secondary structure of an amphipatic alpha helix.

2. Lymphocyte Proliferation Studies

A total of 202 individuals living in a malaria endemic area in the Gambia were tested for induction of lymphocyte proliferation by the fusion protein.

So far, only the ages of the individuals tested and the logarithms of the stimulation indexes have been available. Other variables concerning the individuals of the study relevant for the evaluation of the proliferation assays have been collected, but the analyses are not yet finally analysed. A preliminary conclusion is that the fusion protein does stimulate some individuals in a malaria endemic area. A more detailed interpretation of the study will be possible later.

To analyse the protein in more detail we have performed the following experiments:

Epitopes were searched for in the major repeat area using cloning and expression of a subfragment of glurp. A sau3AI-KpnI fragment comprising base 981-1935 was cloned in the pUC 19-vector. The resulting plasmid was designated pMBB98. The translation product hereof contained the full length of the major repeat area plus another 45 amino acids, in fusion with a part of β-galactosidase. The fusion protein was enzymatically active when expressed in the JM109-*E. coli* strain which carries the gene encoding the ω-complementing part of β-galactosidase on the F'-plasmid.

The bacteria carrying pMBB98 was grown to an $OD_{600}$ of 0.5 in LB-medium, the expression induced by adding IPTG to a total concentration of 1 mM and grown over night. The cells were then harvested by centrifugation and resuspended in 20 ml 10 mM Bis-Tris pH 6 and crushed by passing through a French press. Cell debris were removed by centrifugation 20.000 G for 1 hour and 8 ml of the supernatant was applied on a 100 ml DEAE fast flow sepharose matrix (Pharmacia-LKB, Sweden). The column was subjected to increasing concentrations of NaCl in Bis-Tris pH 6 on an FPLC, and 5 ml fractions collected.

The β-galactosidase activity was used to select fractions to recognize the fractions containing the fusion protein, which was eluted at an NaCl concentration of approximately 0.6M. The selected fractions were pooled, dialysed against PBSA and concentrated to 10 ml by dialysing against solid PEG 20 000.

The ability to induce a proliferative response in T-cells from malaria-immune donors was tested. T-cells from 13 out of 16 donors responded, whereas only T-cells from one out of 8 non-immune donors responded (FIG. 17). The responding non-immune donor was convalescent from a malaria attack 4 weeks earlier.

These results indicate that one or more T-cell epitopes are located within or flanking the repeat area. Two domains within the sequence were found by the AMPHI program to contain potential T-cell epitopes (aa 333-343, and aa 600-613, above). Further investigations of these epitopes using synthetic peptides are under preparation.

The fact that T-cells from the non-immune convalescent reacted, indicates that a single malaria attack could be sufficient for boosting a response, and we propose the usage of such highly potent T-cell epitopes from GLURP as components of a subunit vaccine against malaria.

3. Conservation of epitopes

Among the epitopes, predicted by computer and found by laboratory analysis, the ones which are the most preserved amongst geographically different isolates are the most interesting. These are determined as follows:

Alternatively, parts of the GLURP gene from different isolates are amplified using PCR, cloned into the pUC-vector and sequenced.

The most conserved epitopes are produced as synthetic peptides and tested for T-lymphocyte proliferation stimulatory properties and/or lymfokine secretion.

The thus characterized most efficient B- and T-cell epitopes are then put together, either on the nucleotide level to be produced in an organism or put together as amino acids in synthetic peptides. The combination of the epitopes should be tested for the preservation of the properties of the separate epitopes. That is, the immune stimulating properties of the separate epitopes could be abolished by putting them close together due to interaction between the amino acids.

A possibility is to use tandemly connected units of combined epitopes. One way to achieve this is to connect subunits of epitopes by means of SS-bridges between peptides as described by (Patarroyo M. E. et al: A synthetic vaccine protects humans against challenge with asexual blood stages of Plasmodium falciparum. Nature, 332:158-161;1988). Other way of doing this is to couple the subunits at the nucleotide level and express a novel protein or peptide containing multiple repetitions of the epitopes.

EXAMPLE 11

Figure 1:
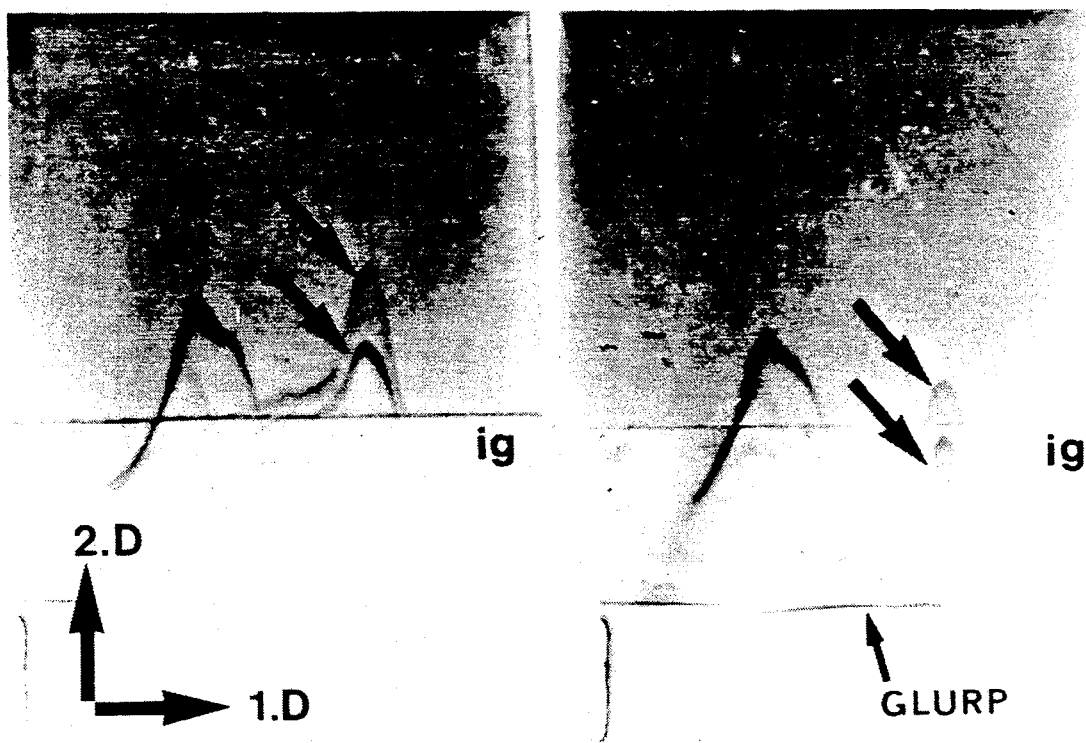
FIG. 1 Crossed immunoelectrophoresis analyses of the specificity of the anti-fusion protein antibodies. A volume of 20 μl of affinity purified antigen from in vitro P. falciparum culture supernatant was separated in the first dimension and run against 400 μl of immune serum in the second dimension. A is the electrophoresis with affinity purified non-immune serum in the intermediate gel (ig), B is with affinity purified immune serum in the intermediate gel. The precipitate representing GLURP is indicated by an arrow and the name; the double arrows indicate antigen 1. GLURP is not precipitated on plate A, probably due to a low content of anti-GLURP antibodies in the serum used in the second dimension. The localization of the precipitate representing GLURP on plate B indicates that the titer of anti-GLURP antibodies in the eluate is very high. The two dimension of the crossed immunoelectrophoresis is shown by the arrows 1.D and 2.D.

Use of Fusion Protein for Affinity Purification of Human Antibodies Directed against GLURP The protein content of pooled fractions was determined according to the Bio-Rad method (Bradford, M. M.:A rapid and sensitive method for the quantitation of microgram quantities of protein utilizing the principle of protein-dye binding. Anal. Biochem. 72:248-254,1976) showing a concentration of 2 mg/ml. Approximately 75 mg of fusion protein was coupled to 15 g (dry weight) of CNBr activated sepharose 4B obtained from Pharmacia Fine Chemicals, Uppsala, Sweden. All procedures for coupling given by the manufacturer were followed. 3 ml of human malaria-immune serum from Liberia was diluted 1:10 in column buffer. The material was filtered and then applied to the column using a pump, flow rate 20 ml/hour. Washing was performed with 3 bed volumes of the column buffer. Elution was done with 3M potassium thiocyanate in column buffer without NaCl. Fractions eluted form the column showing UV absorption above that of the elution buffer were pooled and dialyzed against the column buffer without NaCl. Concentrated on an Amicon diaflow concentration cell to ⅓ the original volume of the serum. The specificity of the eluted antibodies was demonstrated by incorporating the eluted material in an intermediate gel in a crossed immunoelectrophoresis (CIE) (reference: Axelsen, N. H.: Intermediate gel in crossed and in fused rocket immunoelectrophoresis. Scand. J. Immunol. 2, suppl. 1:71-77,1973), FIG. 1.

Native GLURP precipitated immediately after entering the intermediate gel indicating a very high content of anti-native GLURP antibodies in the eluate. Furthermore, antibodies against antigen 1 were present in more limited amounts in the eluate as indicated by the lowering of these precipitates.

To optimize the exploitation of the binding capacity of the column, an ELISA coated with the fusion protein for the monitoring of the run-through may be used. The run-through should not contain major amounts of antibodies against the fusion protein.

EXAMPLE 12A

Three rabbits were immunized with a vaccine composed of 1 volume of 2 mg/ml fusion protein in PBS produced as described in Example 2 and 1 volume of Freunds incomplete adjuvant in a volume ratio of 1:1. Each rabbit received 0.1 ml subcutaneously three times with an interval of one week. One week after the third does, the rabbits were bled. Two weeks after the bleeding they received a new does and were bled one week later and so forth. All analyzes described in the following were performed with bleeding No. 7.

The immunizations were analyzed in immunoblottings, ELISA with fusion protein as the antigen and in competition ELISA with fusion protein coated microtiter plates.

Immunoblotting

Parasites from in vitro P. falciparum culture were harvested, disintegrated by sonic treatment and separated in an SDS-PAGE using the Protean 2 apparatus and electrotransferred onto a nitrocellulose membrane as described in MATERIALS AND METHODS. The rabbit sera was used in dilution 1:100. Rabbit serum obtained before immunization served as control. Preliminary analyses showed that the sera reacted with parasite proteins of molecular weights in the interval of approximately 110-130 kD and bands in the interval of 55-65 kD.

Immunofluorescence

Parasitized red blood cells were coated as a monolayer onto a slide with 12 wells. This was done by precoating the slide with the carbonate buffer pH 9.6 as mentioned for ELISA coating. Precoating was performed for 30 minutes. A drop of a suspension of parasites was placed over each well of the slide for 30 minutes. The slide was washed. Parasites were fixed by covering the wells with acetone and then airdried. Dilutions of the rabbit-anti-fusion protein antibodies were placed on the wells for 30 min. The wells were washed 4 times and fluorescence conjugated, porcine-anti-fusion antibodies (DAKOPATTS F205) diluted 1:40 were applied to each well and incubated for 30 minutes, after which period of time the slide was washed 4 times. The slide was then stained with 10 μg/ml ethidiumbromide and a cover was mounted. The slide was examined in an Olympus BH2 fluorescence microscope.

A preliminary examination of the slide showed that the fluorescence was located to the merozoits of the late schizonts, suggesting that native GLURP was related to this stage of the parasite cycle. A similar study was performed with parasites fixed with 1% glutaraldehyde. This fixation made the red blood cell membrane impermeable to antibodies in contrast to the fixation with acetone. No fluorescence was seen on glutaraldehyde fixed monolayers.

ELISA

Two types of ELISAs were used:

a) coating of each well with 0.125 μg of fusion protein and direct reaction of rabbit serum with the fusion protein and subsequent demonstration of the binding of rabbit antibodies with porcine anti-rabbit immunoglobulin antibodies conjugated to peroxidase (DAKO-PATTS P217) as described in Example 5.

This was used for titration of the sera. The titer which is defined as the dilution of sera at which an OD-value constituting 50% of the maximum OD-vale is obtained was measured to 1/6000, 1/8500 and 1/8500, respectively. The results are shown in FIG. 18.

b) Competition ELISA: A volume of 50 μl of rabbit anti-fusion protein antibodies (purified form a 4 mg/ml pool of rabbit antiserum originating from all three rabbits) diluted 1:2.5 to 1:5120 was added to the wells of an ELISA plate coated with 0.125 μg of fusion protein/well. 15 minutes later, a volume of 50 μl of human-immune serum (IS 141/87, diluted 1:400) was added and the plate was incubated for 1 hour at room temperature on a rocking platform. The binding of human immunoglobulin was detected by rabbit-anti-human IgG conjugated to peroxidase (DAKOPATTS P214) diluted 1:10000, as described in Example 6. This pool of rabbit antiserum was able to occupy epitopes on the fusion protein resulting in a 97% reduction of the binding of human immunoglobulins as compared with the addition of diluted rabbit serum (diluted 1:5120) The plot is shown in FIG. 19.

EXAMPLE 12 B

Immunizations of Mice

With the purpose of producing monoclonal antibodies against the fusion protein, two groups of each four BALB/C mice were immunized with a vaccine containing fusion protein and aluminum hydroxide gel and isotonic saline (for 10 ml of vaccine were used: 200 μg of fusion protein, 2.84 ml aluminum hydroxide gel of a 6.9 mg/ml solution and isotonic saline to 10 ml). A fusion protein preparation purified using 900 mm of gel filtration was used for one group of animals, and for the second group 2700 mm gel filtration was used. The animals were given 1 ml of vaccine intraperitoneally every two weeks. The mice were tested two weeks after the third dose. The mean titer of group 1 immunized with fusion protein purified on 900 ml gel filtration was 1:6000, the mean titer of group 2 immunized with a fusion protein purified on 2700 mm gel filtration was 1:16825, corresponding to an increase in mean titer of 2.8 obtained by using the highly purified fusion protein. The mice were boosted 5 days before fusions. Culture supernatant from hybridomas were screened in the ELISA for detection of antibodies against the fusion protein. Three fusions were performed resulting in detection of only a few clones with very low titers against the fusion protein. Therefore, a fourth fusion was carried out. Culture supernatant will be tested on native GLURP presented on rabbit anti-fusion protein antibodies. Medium for in vitro P. falciparum culture presented on the same antibodies will serve as negative control. Dilutions of hybridoma culture supernatant will be 1:4, detecting antibody conjugated to horseradish peroxidase (DAKOPATTS P260) 1:1000.

Antibodies from mice were tested in immunoblotting showing reactivity with bands of molecular weights similar to the bands recognized by rabbit anti-fusion protein antibodies. Furthermore, antibodies from mice were used as detecting antibodies in the antigen detecting ELISA, being able to recognize the varying amounts of culture supernatant being added as the specimen.

EXAMPLE 12C

Immunization of Saimiri sciureus

The purpose of this study was to show that the fusion protein is efficient as an immunogen in a primate using aluminum hydroxide gel as adjuvant. Four monkeys, Saimiri sciureus from Guyana were used. Every two weeks, two of the four monkeys (monkey No. 864 and monkey No. 865) were immunized with 1 ml of the vaccine containing 60 μg fusion protein, 2.0 mg aluminum hydroxide gel, 0.47 ml isotonic saline, 1% thiomersalatsodium. The other two monkeys (monkey No. 866 and monkey No. 867) were immunized with 1 ml every two weeks of a vaccine consisting of 60 μg fusion protein, 2.0 mg aluminum hydroxide gel, 0.53 ml of Freunds incomplete adjuvant, 1% thiomersalatsodium. The purpose of immunizing two of the monkeys with a vaccine supplemented with Freunds incomplete adjuvant was to expose these two monkeys to the optimal stimulation of the immune systems, thereby serving as positive controls.

The vaccine was given subcutaneously in the posterior axillary line corresponding to the middle of the thorax. The vaccine was given on day 0 of the immunization experiment, day 14 and day 28. Bleedings were performed 132 days before the start of the immunization experiment, on day 0 in the immunization experiment, on day 14, on day 28 and will be performed on day 42.

Blood samples were analysed using ELISA with a coating consisting of 0.125 μg per well. The first four bleedings from each monkey were analysed in dilutions from 1:50 to 1:6400. The presence of monkey antibodies on the coating were detected by rabbit anti monkey serum antibodies diluted 1:1000 which subsequently were visualized using porcine anti-rabbit immunoglobulin antibodies conjugated with horse radish peroxidase (DAKOPATTS P217) diluted 1:1000. Colour developemnt was performed using OPD as the substrate.

The optical density readings of the specimens in the above descried ELISA are shown in FIG. 20.

Serum from monkeys Nos. 867 and 865 diluted 1:200 was tested in immunoblotting. They possess antibodies against the same parasite protein bands as the rabbits.

The conclusion of this experiment is that antibodies against the fusion proteins are effectively induced using aluminum hydroxide gel as the adjuvant. A significant level of antibodies are even induced by a single dose of vaccine.

LIST OF REFERENCES (1) S. Jepsen and N. H. Axelsen, 1980, "Antigens and Antibodies in *Plasmodium falciparum* Malaria Studied by Immunoelectrophorectic Methods", *Acta. Path. Microbiol. Scand. Sect. C*, 88, p. 263-270.

(2) S. Jepsen and B. Jyding Andersen, 1981, "Immunoadsorbent Isolation of Antigens From the Culture Medium of In Vitro cultivated *Plasmodium falciparum*", *Acta. Path. Microbiol. Scand. Sect. C*, 89, p. 99-103.

(3) P. H. Jakobsen, L. Baek & S. Jepsen, 1988, "**Demonstration of soluble *Plasmodium falciparum* antigens reactive with Limulus amoebocyte lysate and polymyxin B**", *Parasite Immunology*, 10, p. 593-606.

(4) I. C. Bygbjerg, S. Jepsen, T. G. Theander & N. Odum, 1985, "Specific proliferative response of human lymphocytes to purified soluble antigens from *Plasmodium falciparum* in vitro cultures and to antigens from malaria patients' sera", *Clin. exp. Immunol.*, 59, p. 421-426.

(5) S. Jepsen, 1983, "Inhibition of in Vitro growth of *Plasmodium falciparum* by Purified Antimalarial Human IgG Antibodies, Isolation of Target Antigens from Culture Supernatants", *Scand. J. Immunol*, 18, p. 567-571.

(6) P. H. Jakobsen, S. Jepsen & R. Agger, 1987, "Inhibitory monoclonal antibodies to soluble *Plasmodium falciparum* antigens", *Parasitol Res.*, 73, p. 518-523.

(7) P. H. Jakobsen, T. G. Theander, J. B. Jensen, K. Molbak & S. Jepsen, 1987, "Soluble *Plasmodium falciparum* Antigens Contain Carbohydrate Moieties Important for Immune Reactivity", *Journal of Clinical Microbiology*, Vol. 25, No. 11, p. 2075-2079.

(8) A. Scherf, C. Hilbich, K. Sieg, D. Mattei, O. Mercereau-Puijalon & B. Müller-Hill, 1988, "The 11-1 gene of *Plasmodium falciparum* codes for distinct fast evolving repeats", *The EMBO Journal*, Vol. 7, No. 4, p. 1129-1137.

(9) T. Triglia, H. Stahl, P. E. Crewther, A. Silva, R. F. Anders & D. J. Kemp, 1988, "Structure of a *Plasmodium falciparum* gene that encodes a glutamic acid-rich protein (GARP)", *Molecular and Biochemical Parasitology*, 31, p. 199-202.

(10) F. B. Perler, A. M. Moon, B. Qin Qiang, M. Meda, M. Dalton, C. Card, R. Schmidt-Ullrich, D. Wallach, J. Lynch & J. E. Donelson, 1987, "Cloning and characterization of an abundant *Plasmodium knowlesi* antigen which cross reacts with Gambian sera", *Molecular and Biochemical Parasitology*, 25, p. 185-193.

We claim:

1. A substantially pure polypeptide comprising the amino acid sequence of a glutamate-rich polypeptide (GLURP) derived from a *Plasmodium falciparum* antigen ("native GLURP"), said GLURP having the amino acid sequence set forth in FIG. 8.

2. A substantially pure polypeptide which comprises at least one epitope reactive with an antibody which recognized the GLURP.

3. A polypeptide according to claim 1 which comprises at least one subsequence which is homologous with a unique repeat selected from the group consisting of the α, β and Γ repeats of GLURP.

4. A polypeptide according to claim 3, in which the amino acid proline does not occupy position 3 of the repeated sequence when read from the N-terminal end of the polypeptide.

5. A polypeptide according to claim 1, further characterized as including at least one of the following amino acid sequences:

Val—Ser—Glu—Pro—Ala—Glu—His—Val;

Lys—Ser—Val—Ser—Glu—Pro—Ala—Glu—His—Val;

Thr—Ser—Glu—Pro—Ala—Glu—His—Val—Glu—Ser—Val—Ser—Glu—Gln—Ser—Asn—Asn;

Lys—Pro—Phe—Glu—Glu—Ile—Glu—Lys;

Glu—Val—Glu—Glu—Ile—Pro—Ser—Glu—Leu—His—Glu;

Glu—Ile—Leu—Pro—Glu—Ile—Val—Glu—Ile—Glu—Glu—Val—Pro—Ser;

Gly—Pro—Lys—His—Val—Glu—Gln;

ISTKKFKKVSQTIVSVMINAYDGVIQVVSTIKGIAK

6. A fusion protein comprising the GLURP amino acid sequence set forth in FIG. 8, fused to β-galactosidase.

7. A polypeptide according to claim 1 coupled to a carbohydrate or a lipid moiety.

* * * * *